United States Patent
Gangjee

(10) Patent No.: US 9,624,178 B2
(45) Date of Patent: *Apr. 18, 2017

(54) SUBSTITUTED CYCLOPENTA PYRIMIDINE BICYCLIC COMPOUNDS HAVING ANTITMITOTIC AND/OR ANTITUMOR ACTIVITY METHODS OF USE THEREOF

(71) Applicant: Duquesne Univversity of the Holy Spirit, Pittsburgh, PA (US)

(72) Inventor: Aleem Gangjee, Allison Park, PA (US)

(73) Assignee: Duquesne University of the Holy Spirit, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/244,445

(22) Filed: Apr. 3, 2014

(65) Prior Publication Data

US 2014/0303188 A1 Oct. 9, 2014

Related U.S. Application Data

(63) Continuation-in-part of application No. 12/170,571, filed on Jul. 10, 2008, now Pat. No. 8,946,239.

(51) Int. Cl.
| | |
|---|---|
| *C07D 239/94* | (2006.01) |
| *A61K 31/517* | (2006.01) |
| *C07D 487/04* | (2006.01) |
| *C07D 491/048* | (2006.01) |
| *C07D 239/70* | (2006.01) |
| *A61K 31/519* | (2006.01) |
| *A61P 35/00* | (2006.01) |

(52) U.S. Cl.
CPC ......... *C07D 239/70* (2013.01); *C07D 487/04* (2013.01); *C07D 491/048* (2013.01)

(58) Field of Classification Search
CPC . C07D 239/70; C07D 2394/94; A61K 31/517
See application file for complete search history.

(56) References Cited

U.S. PATENT DOCUMENTS

| | | | | |
|---|---|---|---|---|
| 5,554,615 | A * | 9/1996 | Nomura | C07D 487/04 514/265.1 |
| 6,660,744 | B1 * | 12/2003 | Hirst | C07F 9/6561 514/210.21 |
| 8,030,319 | B2 | 10/2011 | Gangjee | |
| 2005/0153989 | A1 | 7/2005 | Grotzfeld et al. | |
| 2010/0010016 | A1 | 1/2010 | Gangjee | |
| 2011/0160203 | A1 | 6/2011 | Liu et al. | |
| 2013/0029942 | A1 | 1/2013 | Anderson et al. | |
| 2014/0303188 | A1 | 10/2014 | Gangjee | |

FOREIGN PATENT DOCUMENTS

| | | |
|---|---|---|
| EP | 1661896 | 5/2006 |
| EP | 1661897 | 5/2006 |
| WO | 03/080064 | 10/2003 |
| WO | 2004/087056 | 10/2004 |
| WO | 2006/017443 | 2/2006 |
| WO | 2007/042298 | 4/2007 |
| WO | 2007/115620 | 10/2007 |
| WO | 2008/006547 | 1/2008 |

OTHER PUBLICATIONS

Supplementary European Search Report for EP App. No. 09795102 dated Sep. 13, 2011.
International Search Report and Written Opinion of the International Searching Authority for PCT/US2009/049901 dated Sep. 8, 2009.
STN printout, downloaded Sep. 29, 2013, pp. 417, 469, 470, 471 and 548.
International Search Report of the International Searching Authority for PCT/US2015/022871 dated Dec. 22, 2015.
Written Opinion of the International Searching Authority for PCT/US2015/022871 dated Dec. 22, 2015.

* cited by examiner

Primary Examiner — Susanna Moore
(74) Attorney, Agent, or Firm — Buchanan Ingersoll and Rooney PC

(57) ABSTRACT

The present invention provides substituted cyclopenta and cyclopentyl pyrimidine bicyclic compounds of Formula III,

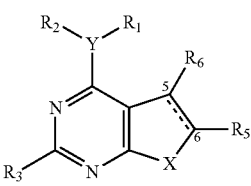

III and 5,6-saturated and unsaturated
and pharmaceutically acceptable salts, prodrugs, solvates, and hydrates thereof, having antimitotic activity, anti-multidrug resistance activity, such as for example P-glycoprotein inhibition, and antitumor activity, and which inhibit paclitaxel sensitive and resistant tumor cells. Also provided are methods of utilizing these compounds for treating tumor cells and inhibiting mitosis of cancerous cells.

5 Claims, 18 Drawing Sheets

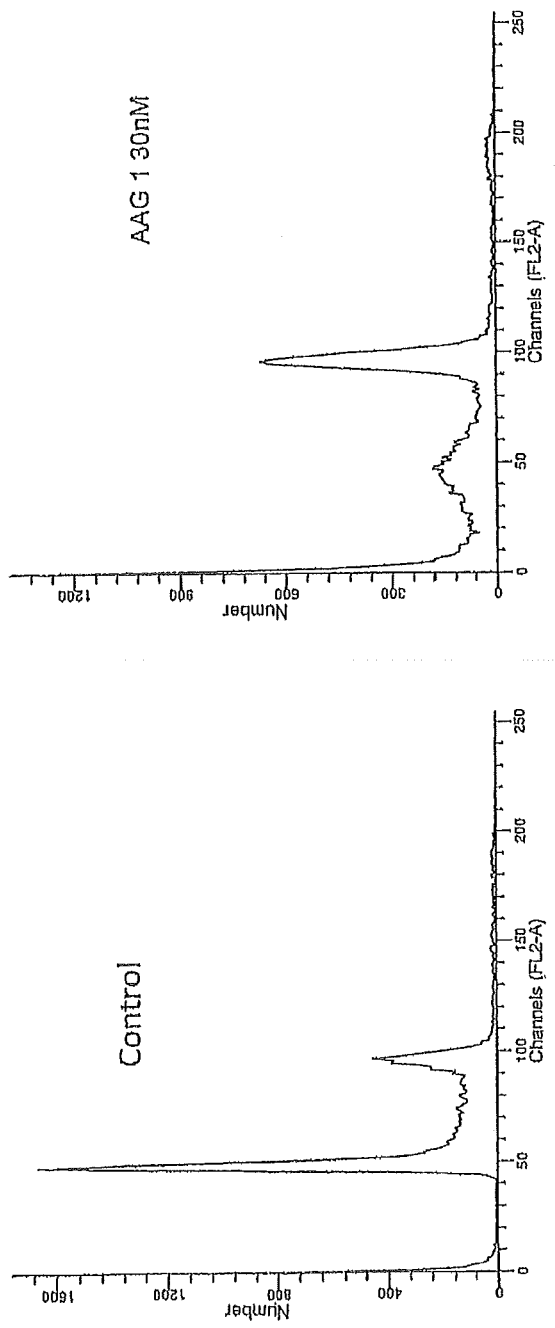
Figure 1a  Effects of AAG Compounds on MDA MB 435 Cell Cycle Distribution

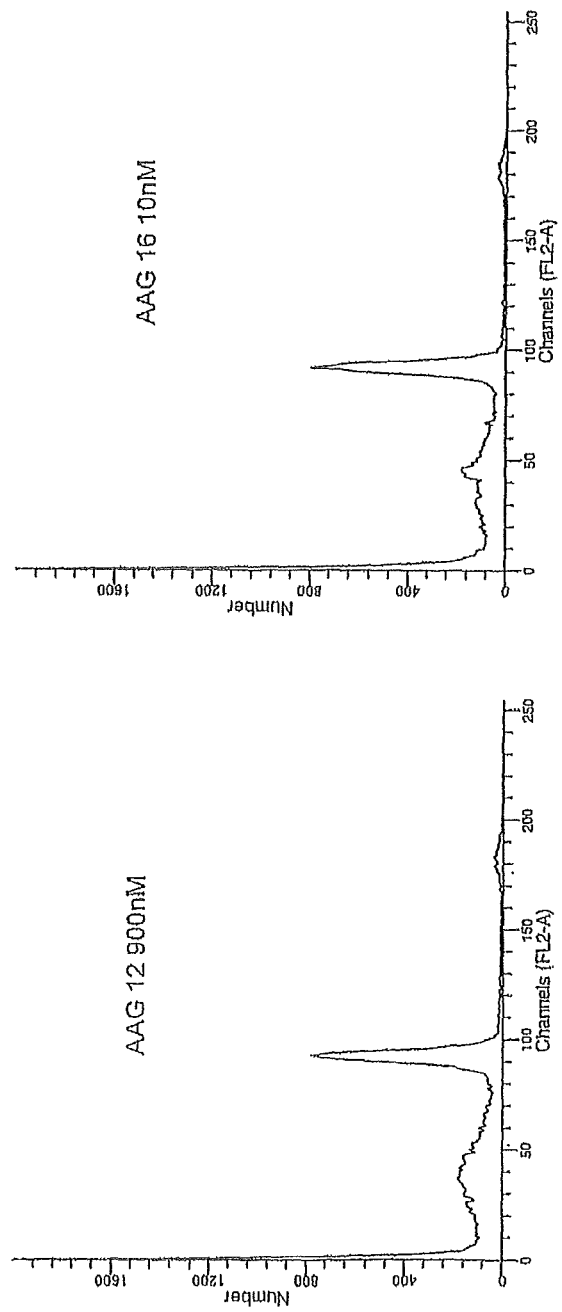
Figure 1b  Effects of AAG Compounds on MDA MB 435 Cell Cycle Distribution

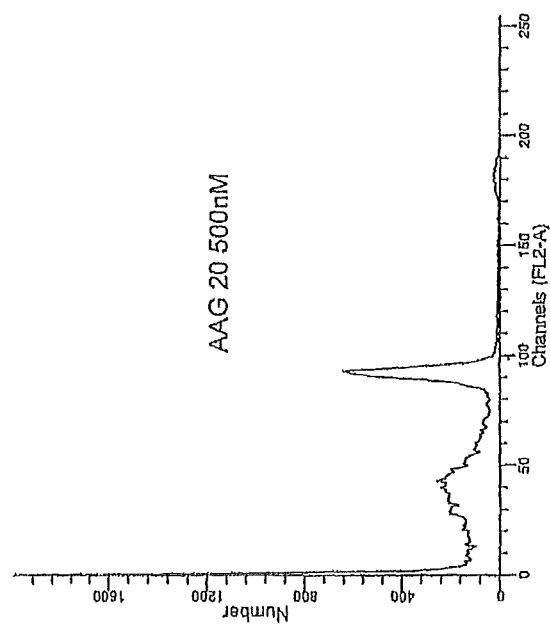
Figure 1c  Effects of AAG Compounds on MDA MB 435 Cell Cycle Distribution Figure 2. Microtubule Depolymerization Immunofluorescence Assay in A-10 Cells
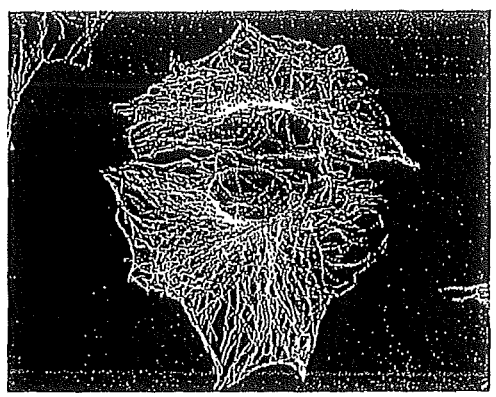
Control
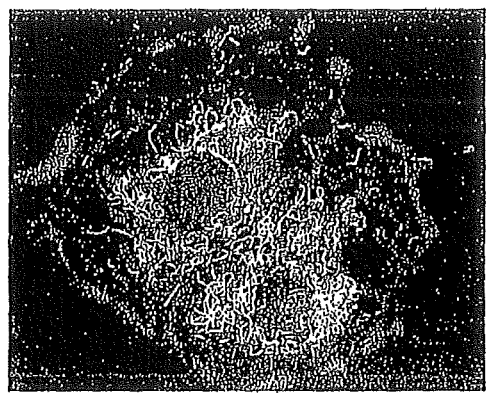
AAG 1 250nM
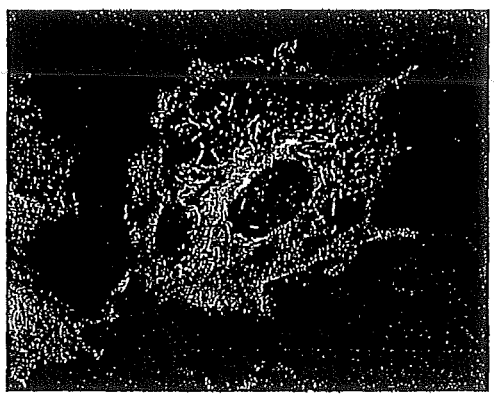
AAG 7 500nM
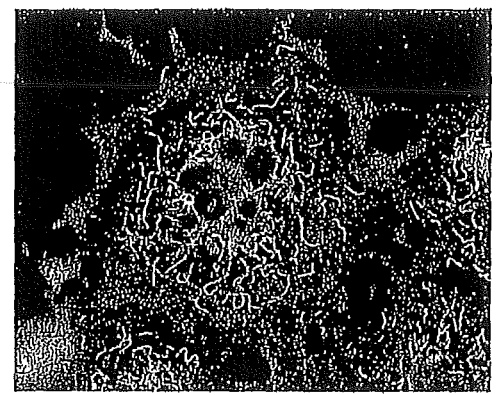
AAG 16 40nM

| Sample ID | Structure |
|---|---|
| AAG1 | 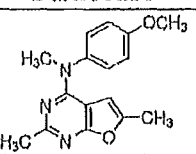 |
| AAG7 | 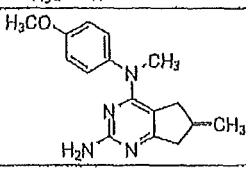 |
| AAG12 | 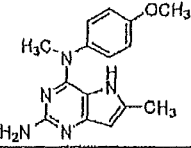 |
| AAG16 | 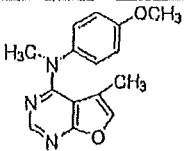 |
| AAG20 | 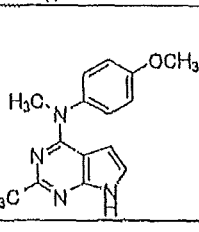 |
| AAG 26 HCl | 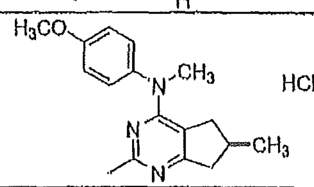 |
Figure 3

Figure 4. Biological Effects of AG Series of Compounds

| Sample ID | IC50 (MDA MB 435) ± SD | IC50 (SKOV3) ± SD (Sensitive) | IC50 (SKOV3M6/6) ± SD (Resistant) | Relative Resistance Value | EC50 for Microtubule Depolymerization |
|---|---|---|---|---|---|
| AAG 1 | 17.1 nM ± 1.5 | 36.7 nM ± 1.5 | 171 nM ± 15.2 | 4.7 | 103.2 nM |
| AAG 7 | 25.7 nM ± 1.3 | 35.9 nM ± 3.0 | 51.8 nM ± 4.8 | 1.4 | 282 nM |
| AAG 12 | 298 nM ± 19.7 | 355 nM ± 15.8 | 731 nM ± 55.6 | 2.1 | 8.4 µM |
| AAG 16 | 4.3 nM ± 0.3 | 7.7 nM ± 0.8 | 8.4 nM ± 0.4 | 1.1 | 23.9 nM |
| AAG 20 | 183 nM ± 3.4 | 278 nM ± 19.0 | 435 nM ± 33.4 | 1.6 | 5.8 µM |
| AAG 26 | 29.9 nM ± 1.9 | 39.5 nM ± 7.7 | 44.4 nM ± 3.2 | 1.1 | 52.1 nM |
| Combrestatin A4 | 2.8 nM ± 0.2 | 4.5 nM ± 0.2 | 6.6 nM ± 1.3 | 1.5 | |
| Taxol | 2.1 nM ± 0.7 | 2.2 nM ± 0.9 | 4.4 µM ± 0.9 | 2013 | |

National Cancer Institute Developmental Therapeutics Program In-Vitro Testing Results

| Panel/Cell Line | Time Zero | CUI | \multicolumn{5}{c}{Mean Optical Densities Log10 Concentration} | | | | |
|---|---|---|---|---|---|---|---|
| | | | -8.0 | -7.0 | -6.0 | -5.0 | -4.0 |
| Leukemia | | | | | | | |
| CCRF-CEM | 0.186 | 0.845 | 0.805 | 0.156 | 0.152 | 0.155 | 0.151 |
| HL-60(TB) | 0.468 | 1.847 | 1.509 | 0.203 | 0.160 | 0.136 | 0.122 |
| K-562 | 0.175 | 1.053 | 0.704 | 0.132 | 0.106 | 0.112 | 0.134 |
| MOLT-4 | 0.336 | 1.023 | 1.055 | 0.265 | 0.218 | 0.186 | 0.237 |
| RPMI-8226 | 0.246 | 0.495 | 0.429 | 0.140 | 0.101 | 0.094 | 0.091 |
| SR | 0.359 | 0.804 | 0.540 | 0.217 | 0.213 | 0.207 | 0.181 |
| Non-Small Cell Lung Cancer | | | | | | | |
| A549/ATCC | 0.193 | 1.193 | 1.142 | 0.361 | 0.294 | 0.305 | 0.204 |
| EKVX | 0.463 | 1.349 | 1.328 | 0.821 | 0.812 | 0.798 | 0.573 |
| HOP-62 | 0.651 | 1.458 | 1.279 | 0.837 | 0.716 | 0.691 | 0.549 |
| NCI-H226 | 0.718 | 1.270 | 1.183 | 0.979 | 0.779 | 0.654 | 0.632 |
| NCI-H23 | 0.453 | 1.325 | 1.204 | 0.687 | 0.546 | 0.499 | 0.414 |
| NCI-H322M | 0.651 | 1.517 | 1.382 | 0.980 | 0.931 | 1.029 | 1.151 |
| NCI-H460 | 0.315 | 2.428 | 2.434 | 0.393 | 0.282 | 0.306 | 0.252 |
| NCI-H522 | 0.356 | 1.128 | 0.553 | 0.262 | 0.236 | 0.229 | 0.198 |
| Colon Cancer | | | | | | | |
| COLO 205 | 0.288 | 0.773 | 0.775 | 0.054 | 0.040 | 0.012 | 0.032 |
| HCC-2998 | 0.522 | 2.033 | 1.831 | 0.726 | 0.689 | 0.593 | 0.462 |
| HCT-116 | 0.152 | 1.264 | 1.221 | 0.256 | 0.136 | 0.102 | 0.095 |
| HCT-15 | 0.165 | 0.925 | 0.794 | 0.200 | 0.106 | 0.085 | 0.143 |
| HT29 | 0.127 | 1.147 | 1.043 | 0.251 | 0.268 | 0.196 | 0.199 |
| KM12 | 0.239 | 0.890 | 0.719 | 0.243 | 0.167 | 0.144 | 0.153 |
| SW-620 | 0.194 | 1.107 | 0.971 | 0.295 | 0.265 | 0.283 | 0.320 |
| CNS Cancer | | | | | | | |
| SF-268 | 0.355 | 0.991 | 0.908 | 0.482 | 0.317 | 0.303 | 0.248 |
| SF-295 | 0.543 | 1.841 | 1.178 | 0.560 | 0.496 | 0.493 | 0.643 |
| SF-539 | 0.667 | 1.885 | 1.717 | 0.442 | 0.406 | 0.504 | 0.699 |
| SNB-19 | 0.536 | 1.306 | 1.207 | 0.669 | 0.579 | 0.646 | 0.624 |
| SNB-75 | 0.450 | 0.970 | 0.866 | 0.652 | 0.606 | 0.654 | 0.648 |
| U251 | 0.270 | 1.180 | 1.130 | 0.293 | 0.216 | 0.199 | 0.108 |
| Melanoma | | | | | | | |
| LOX IMVI | 0.281 | 1.472 | 1.388 | 0.695 | 0.346 | 0.336 | 0.395 |
| MALME-3M | 0.505 | 1.006 | 0.818 | 0.719 | 0.659 | 0.721 | 0.636 |
| M14 | 0.301 | 1.236 | 1.014 | 0.333 | 0.311 | 0.331 | 0.446 |
| SK-MEL-28 | 0.303 | 0.736 | 0.619 | 0.432 | 0.461 | 0.420 | 0.341 |
| SK-MEL-5 | 0.411 | 2.110 | 2.027 | 0.699 | 0.158 | 0.122 | 0.137 |
| UACC-257 | 0.946 | 2.012 | 1.830 | 1.545 | 1.488 | 1.505 | 1.203 |
| UACC-62 | 0.644 | 1.784 | 1.230 | 0.828 | 0.880 | 0.821 | 0.779 |
| Ovarian Cancer | | | | | | | |
| OVCAR-3 | 0.191 | 0.625 | 0.521 | 0.178 | 0.173 | 0.180 | 0.195 |
| OVCAR-4 | 0.352 | 1.202 | 1.114 | 0.583 | 0.650 | 0.604 | 0.596 |
| OVCAR-5 | 0.616 | 1.226 | 1.181 | 0.766 | 0.680 | 0.601 | 0.524 |
| OVCAR-8 | 0.330 | 1.721 | 1.609 | 0.574 | 0.452 | 0.498 | 0.498 |
| SK-OV-3 | 0.430 | 0.954 | 0.893 | 0.399 | 0.352 | 0.346 | 0.303 |
| Renal Cancer | | | | | | | |
| 786-0 | 0.660 | 2.115 | 1.992 | 1.047 | 0.704 | 0.781 | 0.696 |
| A498 | 0.751 | 1.356 | 1.202 | 0.678 | 0.584 | 0.612 | 0.667 |
| ACHN | 0.304 | 1.183 | 1.140 | 0.609 | 0.454 | 0.432 | 0.311 |
| CAKI-1 | 0.424 | 0.561 | 0.519 | 0.364 | 0.366 | 0.375 | 0.317 |
| SN12C | 0.337 | 1.285 | 1.193 | 0.673 | 0.570 | 0.551 | 0.428 |
| TK-10 | 0.478 | 1.204 | 1.186 | 0.911 | 0.827 | 0.866 | 0.669 |
| UO-31 | 0.374 | 1.205 | 1.140 | 0.792 | 0.666 | 0.620 | 0.456 |
| Prostate Cancer | | | | | | | |
| DU-145 | 0.274 | 0.935 | 0.812 | 0.237 | 0.167 | 0.153 | 0.215 |
| Breast Cancer | | | | | | | |
| MCF7 | 0.286 | 1.445 | 1.179 | 0.362 | 0.313 | 0.304 | 0.341 |
| NCI/ADR-RES | 0.388 | 1.481 | 1.102 | 0.276 | 0.220 | 0.247 | 0.293 |
| MDA-MB-231/ATCC | 0.454 | 1.151 | 1.173 | 0.505 | 0.446 | 0.400 | 0.514 |
| HS 578T | 0.439 | 0.844 | 0.705 | 0.344 | 0.378 | 0.341 | 0.358 |
| MDA-MB-435 | 0.361 | 1.349 | 0.573 | 0.140 | 0.176 | 0.201 | 0.433 |
| BT-549 | 0.859 | 1.461 | 1.384 | 1.053 | 0.903 | 0.889 | 0.771 |
| T-47D | 0.324 | 0.632 | 0.631 | 0.428 | 0.504 | 0.519 | 0.408 |
| MDA-MB-468 | 0.995 | 2.482 | 2.137 | 1.403 | 1.144 | 1.023 | 1.171 |

Figure 5a

National Cancer Institute Developmental Therapeutics Program In-Vitro Testing Results

|  |  | Percent Growth | | | | Log 10 Concentration | | |
|---|---|---|---|---|---|---|---|---|
| Panel Cell Line | -8.0 | -7.0 | -6.0 | -5.0 | -4.0 | GI50 | TGI | LC50 |
| Leukemia | | | | | | | | |
| CCRF-CEM | 94 | -15 | -16 | -16 | -18 | 2.63E-8 | 7.30E-8 | > 1.00E-4 |
| HL-60(TB) | 83 | -66 | -67 | -70 | -73 | 1.73E-8 | 3.05E-8 | 9.10E-8 |
| K-562 | 60 | -25 | -40 | -36 | -23 | 1.32E-8 | 6.13E-8 | > 1.00E-4 |
| MOLT-4 | 105 | -21 | -35 | -42 | -29 | 2.72E-8 | 6.70E-8 | > 1.00E-4 |
| RPMI-8226 | 74 | -43 | -59 | -62 | -63 | 1.00E-8 | 4.20E-8 | 2.76E-7 |
| SR | 41 | -40 | -41 | -42 | -50 | < 1.00E-8 | 3.20E-8 | > 1.00E-4 |
| Non-Small Cell Lung Cancer | | | | | | | | |
| A549/ATCC | 95 | 17 | 10 | 11 | 1 | 3.70E-8 | > 1.00E-4 | > 1.00E-4 |
| EKVX | 98 | 39 | 38 | 36 | 10 | 6.48E-8 | > 1.00E-4 | > 1.00E-4 |
| HOP-62 | 78 | 23 | 0 | 5 | -10 | 3.22E-8 | 1.73E-5 | > 1.00E-4 |
| NCI-H226 | 84 | 47 | 11 | -9 | -12 | 8.41E-8 | 3.69E-6 | > 1.00E-4 |
| NCI-H23 | 66 | 27 | 11 | 5 | -9 | 4.07E-6 | 2.40E-5 | > 1.00E-4 |
| NCI-H322M | 84 | 38 | 32 | 44 | 58 | | > 1.00E-4 | > 1.00E-4 |
| NCI-H460 | 100 | 4 | -11 | -3 | -20 | 3.31E-8 | 1.80E-7 | > 1.00E-4 |
| NCI-H522 | 26 | -29 | -33 | -35 | -44 | < 1.00E-8 | 3.12E-8 | > 1.00E-4 |
| Colon Cancer | | | | | | | | |
| COLO 205 | 100 | -67 | -83 | -96 | -89 | 2.00E-8 | 3.97E-8 | 7.88E-8 |
| HCC-2998 | 96 | 7 | 5 | -5 | -26 | 2.85E-8 | 3.20E-6 | > 1.00E-4 |
| HCT-116 | 96 | 0 | -9 | -33 | -36 | 3.40E-8 | 3.10E-7 | > 1.00E-4 |
| HCT-15 | 82 | 2 | -43 | -54 | -23 | 2.63E-8 | 1.11E-7 | |
| HT29 | 90 | 12 | 14 | 7 | 7 | 3.25E-8 | > 1.00E-4 | > 1.00E-4 |
| KM12 | 74 | 1 | -30 | -40 | -39 | 2.11E-8 | 1.04E-7 | > 1.00E-4 |
| SW-620 | 85 | 11 | 10 | 10 | 14 | 2.98E-8 | > 1.00E-4 | > 1.00E-4 |
| CNS Cancer | | | | | | | | |
| SF-268 | 87 | 17 | -11 | -16 | -19 | 3.36E-8 | 4.05E-7 | > 1.00E-4 |
| SF-295 | 68 | 2 | -9 | -9 | 0 | 1.36E-8 | | > 1.00E-4 |
| SF-539 | 86 | -34 | -35 | -25 | 3 | 2.00E-8 | | > 1.00E-4 |
| SNB-19 | 87 | 16 | 6 | 14 | 37 | 3.33E-8 | > 1.00E-4 | > 1.00E-4 |
| SNB-75 | 80 | 39 | 30 | 39 | 38 | 5.32E-8 | > 1.00E-4 | > 1.00E-4 |
| U251 | 95 | 2 | -20 | -26 | -36 | 3.08E-8 | 1.29E-7 | > 1.00E-4 |
| Melanoma | | | | | | | | |
| LOX IMVI | 93 | 36 | 5 | 5 | 6 | 5.49E-8 | > 1.00E-4 | > 1.00E-4 |
| MALME-3M | 62 | 43 | 39 | 43 | 20 | 4.23E-8 | > 1.00E-4 | > 1.00E-4 |
| M14 | 77 | 3 | 1 | 3 | 16 | 2.33E-8 | > 1.00E-4 | > 1.00E-4 |
| SK-MEL-28 | 73 | 30 | 36 | 27 | 9 | 3.39E-8 | > 1.00E-4 | > 1.00E-4 |
| SK-MEL-5 | 95 | 17 | -62 | -70 | -67 | 3.77E-8 | 1.04E-7 | 7.10E-7 |
| UACC-257 | 83 | 59 | 51 | 61 | 30 | 2.29E-5 | > 1.00E-4 | > 1.00E-4 |
| UACC-62 | 55 | 23 | 27 | 22 | 19 | 1.46E-8 | > 1.00E-4 | > 1.00E-4 |
| Ovarian Cancer | | | | | | | | |
| OVCAR-3 | 89 | -7 | -10 | -6 | 1 | 2.01E-8 | | > 1.00E-4 |
| OVCAR-4 | 90 | 39 | 35 | 30 | 26 | 6.04E-8 | > 1.00E-4 | > 1.00E-4 |
| OVCAR-5 | 94 | 35 | 23 | 12 | 1 | 5.68E-8 | > 1.00E-4 | > 1.00E-4 |
| OVCAR-8 | 92 | 18 | 9 | 11 | 12 | 3.66E-8 | > 1.00E-4 | > 1.00E-4 |
| SK-OV-3 | 66 | -7 | -16 | -20 | -30 | 2.62E-8 | 8.39E-6 | > 1.00E-4 |
| Renal Cancer | | | | | | | | |
| 786-0 | 92 | 27 | 3 | 8 | 2 | 4.36E-8 | > 1.00E-4 | > 1.00E-4 |
| A498 | 75 | -10 | -22 | -19 | -11 | 1.95E-8 | 7.05E-8 | > 1.00E-4 |
| ACHN | 95 | 35 | 16 | 15 | 1 | 5.09E-8 | > 1.00E-4 | > 1.00E-4 |
| CAKI-1 | 87 | -14 | -14 | -12 | -25 | 1.03E-8 | 6.70E-8 | > 1.00E-4 |
| SN12C | 92 | 36 | 25 | 23 | 10 | 5.07E-8 | > 1.00E-4 | > 1.00E-4 |
| TK-10 | 97 | 60 | 48 | 53 | 26 | | > 1.00E-4 | > 1.00E-4 |
| UO-31 | 83 | 45 | 32 | 27 | 9 | 7.52E-8 | > 1.00E-4 | > 1.00E-4 |
| Prostate Cancer | | | | | | | | |
| DU-145 | 96 | -14 | -39 | -44 | -22 | 2.02E-8 | 7.50E-8 | > 1.00E-4 |
| Breast Cancer | | | | | | | | |
| MCF7 | 77 | 7 | 2 | 2 | 5 | 2.42E-8 | > 1.00E-4 | > 1.00E-4 |
| NCI/ADR-RES | 95 | -29 | -43 | -36 | -24 | 1.45E-8 | 4.94E-8 | > 1.00E-4 |
| MDA-MB 231/ATCC | 103 | 21 | -1 | -1 | 7 | 4.43E-8 | | > 1.00E-4 |
| HS 578T | 99 | -22 | -14 | -22 | -19 | 1.53E-8 | 5.08E-8 | > 1.00E-4 |
| MDA-MB-435 | 21 | -61 | -51 | -44 | 7 | < 1.00E-8 | | |
| BT-549 | 87 | 33 | 8 | 3 | -11 | 4.88E-8 | 1.08E-5 | > 1.00E-4 |
| T-47D | 93 | 32 | 55 | 69 | 26 | | > 1.00E-4 | > 1.00E-4 |
| MDA-MB-468 | 77 | 27 | 10 | 2 | 12 | 3.49E-8 | > 1.00E-4 | > 1.00E-4 |

Figure 5b

Figure 9 Structures of microtubule targeting agents.

SUBSTITUTED CYCLOPENTA PYRIMIDINE BICYCLIC COMPOUNDS HAVING ANTITMITOTIC AND/OR ANTITUMOR ACTIVITY METHODS OF USE THEREOF

CROSS-REFERENCE TO RELATED APPLICATIONS

This continuation-in-part patent application claims the benefit of pending U.S. patent application Ser. No. 12/170,571, filed on Jul. 10, 2008. The entire contents of U.S. patent application Ser. No. 12/170,571 is incorporated by reference into this continuation-in-part utility patent application as if fully written herein.

STATEMENT REGARDING FEDERALLY SPONSORED RESEARCH OR DEVELOPMENT

This invention was made with government support under Grant No. R01 CA142868 awarded by the National Institute of Health, National Cancer Institute. The government has certain rights in the invention.

FIELD OF THE INVENTION

The present invention relates to bicyclic heteroaromatic compounds and their methods of use and, more particularly, to bicyclic heteroaromatic compounds that are antitumor agents that inhibit the function of microtubules (antimitotic agents or mitotic inhibitors) and that have antitumor activity. These bicyclic heteroaromatic compounds inhibit P-glycoprotein (Pgp) infected tumor cells, and inhibit paclitaxel sensitive and resistant tumor cells. The compounds may be made into acid salts that are water soluble for providing orally active antitumor agents.

BACKGROUND OF THE INVENTION

Mitosis is the process of nuclear division in eukaryotic cells that produces two daughter cells from one parent cell. The daughter cells and the original parent cell have identical chromosomes and DNA. Generally, cancer is a disease of mitosis. It is believed that cancer begins when a single cell is converted from a normal cell to a cancer cell. this is often due to a change in function of one or more genes that normally function to control cell growth. The cancer cells proliferate by repeated, and uncontrolled mitosis, in contrast to normal cells which undergo only about 20 to 50 generations of replication and then cease. A tumor may be thought of as a mass of unhealthy cells that are dividing and growing in an uncontrolled way.

Microtubules are long, protein polymers that are hollow, tube-like filaments found in certain cell components such as the mitotic spindle. Each microtubule is composed of repeating subunits of the protein tubulin. Microtubules aggregate to form spindle fibers. During mitosis, cells use their spindle fibers to line up chromosomes, make copies of them, and divide into new cells with each new daughter cells having a single set of chromosomes. The polymerization dynamics of microtubules play a pivotal role in this process as part of cell replication. The crucial involvement of microtubules in mitosis makes them a target for antitumor agents. Antitumor agents that inhibit the function of microtubules are known as antimitotic agents.

Many classes of antimitotic agents are known. One such class is the vinca alkaloids exemplified by vincristine, vinblastine, vindesine, and vinorelbine. The vinca alkaloids are used in the treatment of leukemias, lymphomas, and small cell lung cancer. Another class of antimitotic agents are the taxanes, exemplified by paclitaxel (commercially available from Bristol-Myers Squibb Company under the tradename TAXOL®) and docetaxel. The taxanes are useful in the treatment of breast, lung, ovarian, head and neck, and bladder carcinomas. Colchicine typifies another class of antimitotic agents. Colchicine, while not used as an antitumor agent, is a microtubule polymerization inhibitor. Lastly, the combrestatins are another class of antitumor agents. Antimitotic agents such as the vinca alakaloids, colchicine, colcemid, and nocadazol block mitosis by keeping the mitotic spindle from being formed. These agents bind to the tubulin and inhibit polymerization, preventing cells from making the spindles they need to move chromosomes around as they divide. In contrast, paclitaxel binds to the tubulin protein of microtubules, locking the microtubules in place and inhibiting their depolymerization. With the mitotic spindle still in place, a cell may not divide into daughter cells.

Multidrug or multiple drug resistance (MDR) is a major drawback of cancer chemotherapy. Ultimate failure of chemotherapy often times occurs with the use of antimitotic agents due to MDR. MDR may be inherently expressed by some tumor types while others acquire MDR after exposure to chemotherapy. P-glycoprotein (Pgp) is a 170 kilodalton (kDa) protein that belongs to the ATP-binding cassette superfamily of transporters. Pgp has been implicated as a primary cause of MDR in tumors. Pgps are efflux transporters found in the gut, gonads, kidneys, biliary system, brain, and other organs. A series of homologous proteins termed multidrug-resistance proteins (MRPs) are also known. MRPs are associated with MDR in tumors. The first MRP termed MRP1 was identified in a drug resistant lung cancer cell line that expressed Pgp. All of these transporters bind drugs within cells and release them to the extracellular space using ATP. Tumor cells pre-exposed to cytotoxic compounds often allow the cells to manifest resistance in the presence of the cytotoxic drug. Overexpression of Pgp has been reported in a number of tumor types, particularly after the patient has received chemotherapy, indicating the clinical importance of Pgp in MDR. The clinical significance of Pgp along with its limited expression in normal tissues makes Pgp a viable target for inhibition to reverse MDR.

While antimitotic agents have shown to be some of the most successful agents against malignancies, resistance, both intrinsic and acquired, often results in treatment failures. Thus, there exists a need to develop new compounds that possess antimitotic activity, anti-multidrug resistance activity, and antitumor activity, that may be used alone as a single agent in the treatment of cancer, or in combination with chemotherapeutic agents, including antimitotic agents, that shall inhibit mitosis in a wide variety of cells, including cells that are subject to MDR. There is a need, therefore, for single compounds which provide the desired antimitotic, anti-multidrug resistance and antitumor activities with a high degree of selectivity and low toxicity, and that are effective inhibitors of paclitaxel sensitive and resistant tumor cells.

SUMMARY OF THE INVENTION

The present invention meets the above need by providing bicyclic compounds having antimitotic activity, anti-multidrug resistance activity (for example, Pgp inhibition), and antitumor activity in a single molecule so that significant drawbacks of different aspects of drug transport of two or more drugs to their targets, additive or synergistic toxicities of two or more different drugs, resistance of cancer cells to a particular drug, as well as the cost associated with two or more drugs, is circumvented.

The present invention provides single compounds that exhibit antimitotic activity, anti-multidrug resistance activity (for example, Pgp inhibition), and antitumor activity in tumor cells, such as, without limitation, leukemia, non-small cell lung cancer, colon cancer, central nervous system cancer, melanoma, ovarian cancer, renal cancer, prostate cancer and breast cancer; and other proliferative diseases and disorders.

The present provides single compounds having a combinatorial chemotherapeutic potential of both antimitotic activity, anti-multidrug resistance activity, and antitumor activity, and which inhibit paclitaxel sensitive and resistant tumor cells.

In an aspect of the present invention, there is provided a compound of Formula III:

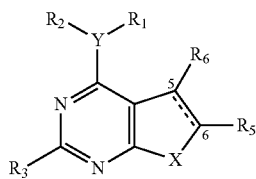

III and 5,6-saturated and unsaturated wherein the five membered ring may be saturated or unsaturated with respect to bond 5-6;

$R_1$ and $R_2$ may be the same or different and comprises one of (a) a hydrogen (H), (b) an alkyl having from one to ten carbon atoms and having a straight or branched configuration, and wherein the alkyl is partially or completely saturated, or a substituted alkyl having from one to ten carbon atoms, (c) a cycloalkyl having from three to ten carbon atoms, or a substituted cycloalkyl having from three to ten carbon atoms, (d) an alkylcycloalkyl, or a substituted alkylcycloalkyl, (e) an aryl, or a substituted aryl, (f) an alkylaryl, or a substituted alkylaryl (g) a heteroaryl, or a substituted heteroaryl, (h) an alkylheteroaryl, or a substituted alkylheteroaryl, (i) an aromatic, or a substituted aromatic, and (j) a heteroaromatic, or a substituted heteroaromatic, and wherein each substituent of any said substituted group is the same or different and is selected from the group consisting of a straight or branched alkyl, alkenyl, or alkynyl, a cyclic or alicyclic group having from one to six carbon atoms, a heterocyclic group having from one to six carbon atoms, an alkoxy group, an aryloxy group, an alkyloxyaryloxy group, an aryl group, an amine, a halogen, a phenol, a naphthalene, a piperidine, a pyrrole, a ketone, a methylalkyl ketone, and a trifluoromethyl ketone, and wherein each of said substituents may itself be substituted, and wherein any of said substituents may be optionally attached by a $CH_2$ bridge, and wherein the substituent may be optionally partially or completely saturated or unsaturated when it is not represented by said halogen;

wherein (i) and (j) may optionally be attached to Y via a $CH_2$ bridge;

$R_3$ comprises one of (a) a hydrogen (H), (b) a halogen, (c) an alkyl having from one to ten carbon atoms and having a straight or a branched configuration, and wherein the alkyl is partially or completely saturated; (d) an $NH_2$, (e) an $NHR_7$, (f) an $NR_7R_8$, (g) an OH, (h) an OR, (i) an SH, and (j) an SR, and wherein R comprises one of $R_1$, and wherein $R_7$ and $R_8$ may be the same or different and comprise one of $R_1$;

$R_4$ comprises one of (a) $R_1$, (b) a halogen, (c) a mono-, di-, tri- or tetra-substituted alkyl, and (d) an alkyloxy, and wherein $R_1$ is H or a lower alkyl and $R_2$ is H or a lower alkyl then $R_4$ comprises one of (a) a $NR_6R_7$, (b) a $SR_6$, (c) a $OR_6$, and (d) a $CHR_6R_7$, wherein $R_6$ and $R_7$ may be the same or different and comprise one of $R_1$ and $R_2$;

$R_5$ comprises one of $R_1$;

$R_6$ comprises one of $R_1$;

X comprises one of (a) $NR_4$, (b) an oxygen (O), and (c) a $R_7CR_4$; and

Y comprises one of (a) a nitrogen (N), (b) an oxygen (O), (c) a sulfur (S), and (d) a $CR_6$, wherein $R_6$ comprises one of $R_1$ and $R_3$, and wherein when Y comprises O or S then $R_2$ is absent. Preferably, the compound of Formula III as described herein, comprises pharmaceutically acceptable salts, prodrugs, solvates, or hydrates thereof.

In another embodiment of the present invention, the compound of Formula III, as described herein, is provided, wherein $R_5$, $R_6$, and $R_3$ are the same moiety. Preferably, a further embodiment comprises wherein the compounds are pharmaceutically acceptable salts, prodrugs, solvates, or hydrates thereof.

In another embodiment of the present invention, the compound of Formula III, as described herein, is provided, wherein $R_7$, $R_4$, $R_6$, and $R_5$ are each a moiety comprising one of $R_1$. Preferably, a further embodiment comprises wherein the compounds are pharmaceutically acceptable salts, prodrugs, solvates, or hydrates thereof.

In another aspect of the present invention, there is provided a compound of Formula IV:

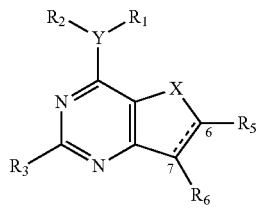

IV and 6,7-saturated and unsaturated wherein the five membered ring may be saturated or unsaturated with respect to bond 6-7;

$R_1$ and $R_2$ may be the same or different and comprises one of (a) a hydrogen (H), (b) an alkyl having from one to ten carbon atoms and having a straight or branched configuration, and wherein the alkyl is partially or completely saturated, or a substituted alkyl having from one to ten carbon atoms, (c) a cycloalkyl having from three to ten carbon atoms, or a substituted cycloalkyl having from three to ten carbon atoms, (d) an alkylcycloalkyl, or a substituted alkylcycloalkyl, (e) an aryl, or a substituted aryl, (f) an alkylaryl, or a substituted alkylaryl (g) a heteroaryl, or a substituted heteroaryl, (h) an alkylheteroaryl, or a substituted alkylheteroaryl, (i) an aromatic, or a substituted aromatic, and (j) a heteroaromatic, or a substituted heteroaromatic, and wherein each substituent of any said substituted group is the same or different and is selected from the group consisting of a straight or branched alkyl, alkenyl, or alkynyl, a cyclic or alicyclic group having from one to six carbon atoms, a heterocyclic group having from one to six carbon atoms, an alkoxy group, an aryloxy group, an alkyloxyaryloxy group, an aryl group, an amine, a halogen, a phenol, a naphthalene, a piperidine, a pyrrole, a ketone, a methylalkyl ketone, and a trifluoromethyl ketone, and wherein each of said substituents may itself be substituted, and wherein any of said substituents may be optionally attached by a CH$_2$ bridge, and wherein the substituent may be optionally partially or completely saturated or unsaturated when it is not represented by said halogen;

wherein (i) and (j) may optionally be attached to Y via a CH$_2$ bridge;

R$_3$ comprises one of (a) a hydrogen (H), (b) a halogen, (c) an alkyl having from one to ten carbon atoms and having a straight or a branched configuration, and wherein the alkyl is partially or completely saturated; (d) an NH$_2$, (e) an NHR$_7$, (f) an NR$_7$R$_8$, (g) an OH, (h) an OR, (i) an SH, and (j) an SR, and wherein R comprises one of R$_1$, and wherein R$_7$ and R$_8$ may be the same or different and comprise one of R$_1$;

R$_4$ comprises one of (a) R$_1$, (b) a halogen, (c) a mono-, di-, tri- or tetra-substituted alkyl, and (d) an alkyloxy, and wherein R$_1$ is H or a lower alkyl and R$_2$ is H or a lower alkyl then R$_4$ comprises one of (a) a NR$_6$R$_7$, (b) a SR$_6$, (c) a OR$_6$, and (d) a CHR$_6$R$_7$, wherein R$_6$ and R$_7$ may be the same or different and comprise one of R$_1$ and R$_2$;

R$_5$ comprises one of R$_1$;

R$_6$ comprises one of R$_1$;

X comprises one of (a) a NR$_4$, (b) an oxygen (O), and (c) R$_7$CR$_4$; and

Y comprises one of (a) a nitrogen (N), (b) an oxygen (O), (c) a sulfur (S), and (d) a CR$_6$, wherein R$_6$ comprises one of R$_1$ and R$_3$, and wherein when Y comprises O or S then R$_2$ is absent (i.e is zero). Preferably, the compound of Formula IV, as described herein, comprises a pharmaceutically acceptable salt, prodrug, solvate, or hydrate thereof.

In another embodiment of this invention, the compound having Formula IV, as described herein, further comprises wherein R$_5$, R$_6$, and R$_3$ are the same moiety. Preferably, in another embodiment, the Formula IV wherein R$_5$, R$_6$, and R$_3$ are the same moiety, comprises a pharmaceutically acceptable salt, prodrug, solvate, or hydrate thereof.

In another embodiment of this invention, the compound of Formula IV, as described herein, is provided comprising wherein R$_6$ and R$_5$ are the same moiety and comprise one of R$_1$. Preferably, in another embodiment of this invention, the compound of the Formula IV wherein R$_6$ and R$_5$ are the same moiety, comprises a pharmaceutically acceptable salt, prodrug, solvate, or hydrate thereof.

In another embodiment of this invention, a method of treating a patient having cancer is provided comprising administering to the patient a therapeutically effective amount of a compound of Formula III, as described herein, or a pharmaceutically acceptable salt, prodrug, solvate, or hydrate thereof.

In another embodiment of this invention, a method of treating a patient having cancer is provided comprising administering to the patient a therapeutically effective amount of a compound of Formula IV, as described herein, or a pharmaceutically acceptable salt, prodrug, solvate, or hydrate thereof.

In yet another embodiment of this invention, a method for inhibiting the mitosis of one or more cancerous cells is provided comprising subjecting one or more live cancerous cell to a mitotic inhibitory amount of a compound of Formula III, as described herein, or a pharmaceutically acceptable salt, prodrug, solvate, or hydrate of the compound of Formula IIII, for effecting the inhibition of mitosis of the cancerous cell(s).

Another embodiment of this invention provides a method for inhibiting the mitosis of one or more cancerous cells comprising subjecting at least one live cancerous cell to a mitotic inhibitory amount of a compound of Formula IV, as described herein, or a pharmaceutically acceptable salt, prodrug, solvate, or hydrate of a compound of Formula IV, for effecting the inhibition of mitosis of the cancerous cell(s).

In a more preferred embodiment of this invention, a compound of Formula III:

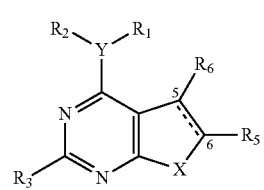

and 5,6-saturated and unsaturated
with respect to the five membered ring;

R$_1$ and R$_2$ may be the same or different and each is one of (a) a hydrogen (H), (b) an alkyl having from one to ten carbon atoms and having a straight or branched configuration, and wherein the alkyl is partially or completely saturated, or a substituted alkyl having from one to ten carbon atoms, (c) a cycloalkyl having from three to ten carbon atoms, or a substituted cycloalkyl having from three to ten carbon atoms, (d) an alkylcycloalkyl, or a substituted alkylcycloalkyl, (e) an aryl, or a substituted aryl, (f) an alkylaryl, or a substituted alkylaryl (g) a heteroaryl, or a substituted heteroaryl, (h) an alkylheteroaryl, or a substituted alkylheteroaryl, (i) an aromatic, or a substituted aromatic, and (j) a heteroaromatic, or a substituted heteroaromatic, and wherein each substituent of any said substituted group is the same or different and is selected from the group consisting of a straight or branched alkyl, alkenyl, or alkynyl, a cyclic or alicyclic group having from one to six carbon atoms, a heterocyclic group having from one to six carbon atoms, an alkoxy group, an aryloxy group, an alkyloxyaryloxy group, an aryl group, an amine, a halogen, a phenol, a naphthalene, a piperidine, a pyrrole, a ketone, a methylalkyl ketone, and a trifluoromethyl ketone, and wherein each of said substituents may itself be substituted, and wherein any of said substituents may be optionally attached by a CH$_2$ bridge, and wherein the substituent may be optionally partially or completely saturated or unsaturated when it is not represented by said halogen;

wherein (i) and (j) may optionally be attached to Y via a CH$_2$ bridge;

wherein R$_1$ and R$_2$ are not each hydrogen (H) when Y is N;

R$_3$ is one of (a) a hydrogen (H), (b) a halogen, (c) an alkyl having from one to ten carbon atoms and having a straight or a branched configuration, and wherein the alkyl is partially or completely saturated; (d) an NH$_2$, (e) an NHR$_7$, (f) an NR$_7$R$_8$, (g) an OH, (h) an OR, (i) an SH, and (j) an SR, and wherein R is one of R$_1$, and wherein R$_7$ and R$_8$ may be the same or different and is one of R$_1$;

R$_5$ is one of R$_1$, except when R$_6$ is a hydrogen (H), heteroaryl, or phenyl, wherein the phenyl and heteroaryl are optionally substituted with 1-2 moieties independently selected from the group consisting of halogen, (C$_1$-C$_4$)alkyl, (C$_1$-C$_4$)fluoroalkyl, (C$_1$-C$_4$)alkoxy, (C$_1$-C$_4$)alkylamine, and (C$_1$-C$_4$)dialkylamine, then R$_5$ is not (i) a hydrogen (H), or (ii) a phenyl group substituted at any position with a substituent selected from the group consisting of (a) a hydrogen, (b) a halogen, (c) CN, (d) OH, (e) $NH_2$, (f) $(C_1$-$C_4)$alkyl, (g) $(C_3$-$C_6)$cycloalkyl, (h) $(C_1$-$C_4)$fluoroalkyl, (i) $(C_1$-$C_4)$alkoxy, (j) $(C_1$-$C_4)$alkylamine, (k) $(C_1$-$C_4)$dialkylamine, (l) C(O)OH, (m) C(O)—$NH_2$, (n) C(O)—$(C_1$-$C_4)$ alkyl, (O)C(O)—$(C_1$-$C_4)$fluoroalkyl, (p) C(O)—$(C_1$-$C_4)$ alkylamine, and (q) C(O)—$(C_1$-$C_4)$alkoxy;

$R_6$ is one of $R_1$;

X is a carbon (C) or a $CR_4$; and

Y is one of (a) a nitrogen (N), (b) an oxygen (O), (c) a sulfur (S), and (d) a $CR_6$, wherein $R_6$ is one of $R_1$ and $R_3$ except when Y is $CR_6$ then said $R_6$ is not H when $R_1$ and $R_2$ are each H, and wherein when Y is O or S then $R_2$ is absent or is zero. Further, this invention provides for the compound of Formula III comprising pharmaceutically acceptable salts, hydrates, and solvates thereof. More preferably, this invention provides for a compound of Formula III, as described herein, wherein $R_1$ is either a hydrogen or said alkyl having from one to ten carbon atoms and $R_2$ is a substituted naphthyl, or wherein $R_1$ is a substituted naphthyl and $R_2$ is either a hydrogen or said alkyl having from one to ten carbon atoms. Most preferably, this invention provides the compound of Formula III wherein the substituted naphthyl is a methoxynaphthyl group and wherein the 5,6 bond is a single bond.

Another embodiment of this invention provides a compound comprising Formula IV:

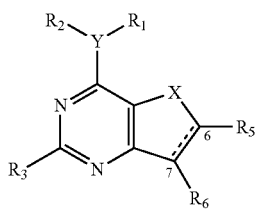

IV and 6,7-saturated and unsaturated wherein $R_1$ and $R_2$ may be the same or different and comprises one of (a) a hydrogen (H), (b) an alkyl having from one to ten carbon atoms and having a straight or branched configuration, and wherein the alkyl is partially or completely saturated, or a substituted alkyl having from one to ten carbon atoms, (c) a cycloalkyl having from three to ten carbon atoms, or a substituted cycloalkyl having from three to ten carbon atoms, (d) an alkylcycloalkyl, or a substituted alkylcycloalkyl, (e) an aryl, or a substituted aryl, (f) an alkylaryl, or a substituted alkylaryl (g) a heteroaryl, or a substituted heteroaryl, (h) an alkylheteroaryl, or a substituted alkylheteroaryl, (i) an aromatic, or a substituted aromatic, and (j) a heteroaromatic, or a substituted heteroaromatic, and wherein each substituent of any said substituted group is the same or different and is selected from the group consisting of a straight or branched alkyl, alkenyl, or alkynyl, a cyclic or alicyclic group having from one to six carbon atoms, a heterocyclic group having from one to six carbon atoms, an alkoxy group, an aryloxy group, an alkyloxyaryloxy group, an aryl group, an amine, a halogen, a phenol, a naphthalene, a piperidine, a pyrrole, a ketone, a methylalkyl ketone, and a trifluoromethyl ketone, and wherein each of said substituents may itself be substituted, and wherein any of said substituents may be optionally attached by a $CH_2$ bridge, and wherein the substituent may be optionally partially or completely saturated or unsaturated when it is not represented by said halogen;

wherein (i) and (j) may optionally be attached to Y via a $CH_2$ bridge;

$R_3$ comprises one of (a) a hydrogen (H), (b) a halogen, (c) an alkyl having from one to ten carbon atoms and having a straight or a branched configuration, and wherein the alkyl is partially or completely saturated; (d) an $NH_2$, (e) an $NHR_7$, (f) an $NR_7R_8$, (g) an OH, (h) an OR, (i) an SH, and (j) an SR, and wherein R comprises one of $R_1$, and wherein $R_7$ and $R_8$ may be the same or different and comprise one of $R_1$;

$R_4$ comprises one of (a) $R_1$, (b) a halogen, (c) a mono-, di-, tri- or tetra-substituted alkyl, and (d) an alkyloxy, and wherein $R_1$ is H or a lower alkyl and $R_2$ is H or a lower alkyl then $R_4$ comprises one of (a) a $NR_6R_7$, (b) a $SR_6$, (c) a $OR_6$, and (d) a $CHR_6R_7$, wherein $R_6$ and $R_7$ may be the same or different and comprise one of $R_1$ and $R_2$;

$R_5$ comprises one of $R_1$;

$R_6$ comprises one of $R_1$;

X is a carbon (C) or a $CR_4$; and

Y comprises one of (a) a nitrogen (N), (b) an oxygen (O), (c) a sulfur (S), and (d) a $CR_6$, wherein $R_6$ comprises one of $R_1$ and $R_3$. Further, this invention provides for a compound of Formula IV comprising pharmaceutically acceptable salts, solvates, and hydrates thereof. More preferably, this invention provides for the compound of Formula IV, as described herein, wherein $R_1$ is either a hydrogen or said alkyl having from one to ten carbon atoms and $R_2$ is a substituted naphthyl, or wherein $R_1$ is a substituted naphthyl and $R_2$ is either a hydrogen or said alkyl having from one to ten carbon atoms. Most preferably, this invention provides for a compound of Formula IV, as described herein, wherein said substituted naphthyl is a methoxynaphthyl.

BRIEF DESCRIPTION OF THE DRAWINGS

A full understanding of the invention can be gained from the following description of the preferred embodiments when read in conjunction with the accompanying drawings in which:

FIGS. 1a, 1b, and 1c show the effects of various compounds of the present invention on a cancer cell line's cell cycle distribution.

FIG. 2 shows a microtubule depolymerization immunofluorescence assay of A10 rat smooth muscle tumor cell line following treatment with compounds of the present invention, namely, Sample IDs AAG1, AAG7, and AAG16.

FIG. 3 shows the chemical structures of six compounds of the present invention, namely, Sample IDs AAG1, AAG7, AAG12, AAG16, AAG20, and AAG26.

FIG. 4 shows the biological effects of the compounds of the present invention.

FIGS. 5a and 5b shows the results of the National Cancer Institute's 55 preclinical in vitro tumor screening panel evaluating a compound of the present invention, namely, Sample ID AAG1.

DESCRIPTION OF THE PREFERRED EMBODIMENTS

Figure 6A:
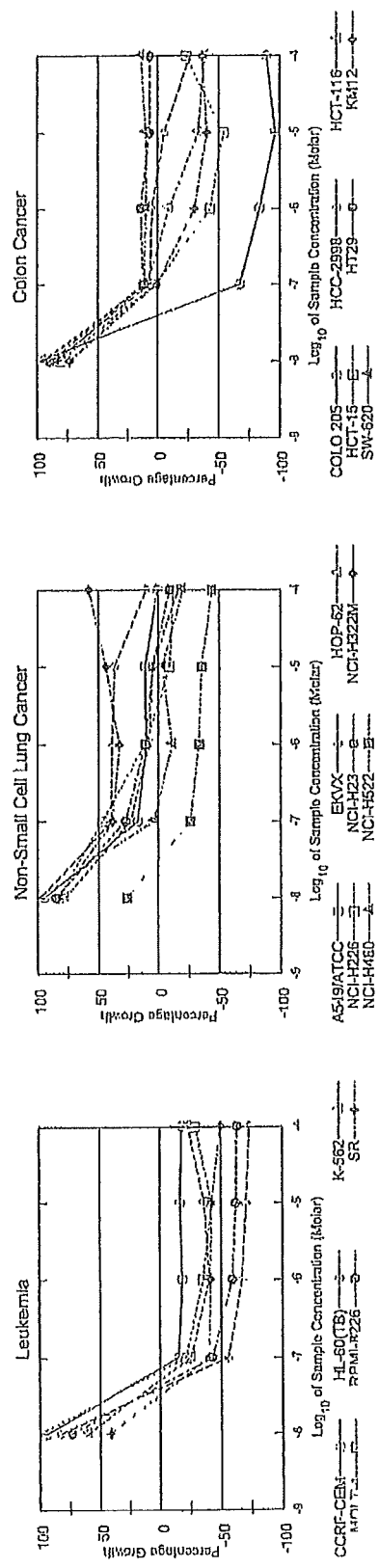
FIGS. 6a, 6b and 6c show individual dose response curves of percentage growth for each of the cancer cell lines set forth in FIG. 5.

The present invention provides bicyclic compounds having antimitotic activity, anti-multidrug resistance activity (for example, Pgp inhibition), and antitumor activity, and which inhibit paclitaxel sensitive and resistant tumor cells in a single molecule and methods of use thereof.

The present invention provides a compound of the Formula III:

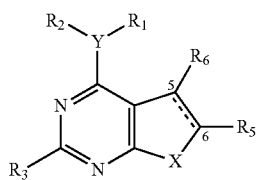

III and 5,6-saturated and unsaturated
wherein the five membered ring may be saturated or unsaturated with respect to bond 5-6;

$R_1$ and $R_2$ may be the same or different and comprises one of (a) a hydrogen (H), (b) an alkyl having from one to ten carbon atoms and having a straight or branched configuration, and wherein the alkyl is partially or completely saturated, or a substituted alkyl having from one to ten carbon atoms, (c) a cycloalkyl having from three to ten carbon atoms, or a substituted cycloalkyl having from three to ten carbon atoms, (d) an alkylcycloalkyl, or a substituted alkylcycloalkyl, (e) an aryl, or a substituted aryl, (f) an alkylaryl, or a substituted alkylaryl (g) a heteroaryl, or a substituted heteroaryl, (h) an alkylheteroaryl, or a substituted alkylheteroaryl, (i) an aromatic, or a substituted aromatic, and (j) a heteroaromatic, or a substituted heteroaromatic, and wherein each substituent of any said substituted group is the same or different and is selected from the group consisting of a straight or branched alkyl, alkenyl, or alkynyl, a cyclic or alicyclic group having from one to six carbon atoms, a heterocyclic group having from one to six carbon atoms, an alkoxy group, an aryloxy group, an alkyloxyaryloxy group, an aryl group, an amine, a halogen, a phenol, a naphthalene, a piperidine, a pyrrole, a ketone, a methylalkyl ketone, and a trifluoromethyl ketone, and wherein each of said substituents may itself be substituted, and wherein any of said substituents may be optionally attached by a $CH_2$ bridge, and wherein the substituent may be optionally partially or completely saturated or unsaturated when it is not represented by said halogen;

wherein (i) and (j) may optionally be attached to Y via a $CH_2$ bridge;

$R_3$ comprises one of (a) a hydrogen (H), (b) a halogen, (c) an alkyl having from one to ten carbon atoms and having a straight or a branched configuration, and wherein the alkyl is partially or completely saturated; (d) an $NH_2$, (e) an $NHR_7$, (f) an $NR_7R_8$, (g) an OH, (h) an OR, (i) an SH, and (j) an SR, and wherein R comprises one of $R_1$, and wherein $R_7$ and $R_8$ may be the same or different and comprise one of $R_1$;

$R_4$ comprises one of (a) $R_1$, (b) a halogen, (c) a mono-, di-, tri- or tetra-substituted alkyl, and (d) an alkyloxy, and wherein $R_1$ is H or a lower alkyl and $R_2$ is H or a lower alkyl then $R_4$ comprises one of (a) a $NR_6R_7$, (b) a $SR_6$, (c) a $OR_6$, and (d) a $CHR_6R_7$, wherein $R_6$ and $R_7$ may be the same or different and comprise one of $R_1$ and $R_2$;

$R_5$ comprises one of $R_1$;

$R_6$ comprises one of $R_1$;

X comprises one of (a) $NR_4$, (b) an oxygen (O), and (c) $R_7CR_4$; and

Y comprises one of (a) a nitrogen (N), (b) an oxygen (O), (c) a sulfur (S), and (d) a $CR_6$, wherein $R_6$ comprises one of $R_1$ and $R_3$, and wherein when Y comprises O or S then $R_2$ is absent (i.e. is zero).

In another embodiment of this invention the compound having Formula III, as described herein, further comprises wherein $R_5$, $R_6$, and $R_3$ are the same moiety.

In yet another embodiment of this invention the compound of Formula III, as described herein, further comprises wherein $R_7$, $R_4$, $R_6$, and $R_5$ are each a moiety comprising $R_1$.

Preferably, the compounds of Formula III, as described herein, are pharmaceutically acceptable salts, prodrugs, solvates, or hydrates thereof.

Another embodiment of this invention provides a compound of Formula IV:

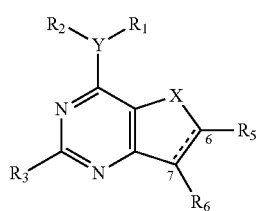

IV and 6,7-saturated and unsaturated
wherein the five membered ring may be saturated or unsaturated with respect to bond 6-7;

$R_1$ and $R_2$ may be the same or different and comprises one of (a) a hydrogen (H), (b) an alkyl having from one to ten carbon atoms and having a straight or branched configuration, and wherein the alkyl is partially or completely saturated, or a substituted alkyl having from one to ten carbon atoms, (c) a cycloalkyl having from three to ten carbon atoms, or a substituted cycloalkyl having from three to ten carbon atoms, (d) an alkylcycloalkyl, or a substituted alkylcycloalkyl, (e) an aryl, or a substituted aryl, (f) an alkylaryl, or a substituted alkylaryl (g) a heteroaryl, or a substituted heteroaryl, (h) an alkylheteroaryl, or a substituted alkylheteroaryl, (i) an aromatic, or a substituted aromatic, and (j) a heteroaromatic, or a substituted heteroaromatic, and wherein each substituent of any said substituted group is the same or different and is selected from the group consisting of a straight or branched alkyl, alkenyl, or alkynyl, a cyclic or alicyclic group having from one to six carbon atoms, a heterocyclic group having from one to six carbon atoms, an alkoxy group, an aryloxy group, an alkyloxyaryloxy group, an aryl group, an amine, a halogen, a phenol, a naphthalene, a piperidine, a pyrrole, a ketone, a methylalkyl ketone, and a trifluoromethyl ketone, and wherein each of said substituents may itself be substituted, and wherein any of said substituents may be optionally attached by a $CH_2$ bridge, and wherein the substituent may be optionally partially or completely saturated or unsaturated when it is not represented by said halogen;

wherein (i) and (j) may optionally be attached to Y via a $CH_2$ bridge;

$R_3$ comprises one of (a) a hydrogen (H), (b) a halogen, (c) an alkyl having from one to ten carbon atoms and having a straight or a branched configuration, and wherein the alkyl is partially or completely saturated; (d) an $NH_2$, (e) an $NHR_7$, (f) an $NR_7R_8$, (g) an OH, (h) an OR, (i) an SH, and (j) an SR, and wherein R comprises one of $R_1$, and wherein $R_7$ and $R_8$ may be the same or different and comprise one of $R_1$;

$R_4$ comprises one of (a) $R_1$, (b) a halogen, (c) a mono-, di-, tri- or tetra-substituted alkyl, and (d) an alkyloxy, and wherein $R_1$ is H or a lower alkyl and $R_2$ is H or a lower alkyl then $R_4$ comprises one of (a) a $NR_6R_7$, (b) a $SR_6$, (c) a $OR_6$, and (d) a $CHR_6R_7$, wherein $R_6$ and $R_7$ may be the same or different and comprise one of $R_1$ and $R_2$;

$R_5$ comprises one of $R_1$;

$R_6$ comprises one of $R_1$;

X comprises one of (a) $NR_4$, (b) an oxygen (O), and (c) $R_7CR_4$; and

Y comprises one of (a) a nitrogen (N), (b) an oxygen (O), (c) a sulfur (S), and (d) a $CR_6$, wherein $R_6$ comprises one of $R_1$ and $R_3$, and wherein when Y comprises O or S then $R_2$ is absent (i.e. is zero).

In another embodiment of this invention the compound having Formula IV, as described herein, is provided comprising wherein R5, R6, and R3 are the same moiety.

In yet another embodiment of this invention the compound having Formula IV, as described herein, is provided comprising wherein $R_6$, and $R_5$ are the same moiety and comprise one of $R_1$.

Other embodiments of the present invention provide pharmaceutically acceptable salts, prodrugs, solvates, and hydrates of the compounds of Formulae III and IV. Preferably, the compounds of the present invention represented by Formulae III and IV may be made into acid salts that are water soluble. Most preferably, these water soluble salts of Formulae III and IV may be formulated into an oral dosage forms providing orally administered active antitumor agents. In the past, antimitotic agents have been plagued with water solubility problems, such as for example but not limited to Taxol® and combrestastatin, and a variety of solubilizing agents have been employed to improve their water solubility. The present salts of Formulae III and IV overcome such water solubility problems and are generally completely water soluble.

In another embodiment of this invention, a method of treating a patient having cancer is provided comprising administering to the patient a therapeutically effective amount of a compound of Formula III, as described herein, or a pharmaceutical acceptable salt, prodrug, solvate, or hydrate of the compound of Formula III:

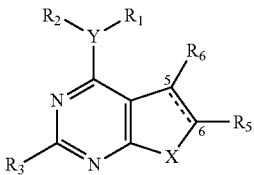

and 5,6-saturated and unsaturated wherein the five membered ring may be saturated or unsaturated with respect to bond 5-6;

$R_1$ and $R_2$ may be the same or different and comprises one of (a) a hydrogen (H), (b) an alkyl having from one to ten carbon atoms and having a straight or branched configuration, and wherein the alkyl is partially or completely saturated, or a substituted alkyl having from one to ten carbon atoms, (c) a cycloalkyl having from three to ten carbon atoms, or a substituted cycloalkyl having from three to ten carbon atoms, (d) an alkylcycloalkyl, or a substituted alkylcycloalkyl, (e) an aryl, or a substituted aryl, (f) an alkylaryl, or a substituted alkylaryl (g) a heteroaryl, or a substituted heteroaryl, (h) an alkylheteroaryl, or a substituted alkylheteroaryl, (i) an aromatic, or a substituted aromatic, and (j) a heteroaromatic, or a substituted heteroaromatic, and wherein each substituent of any said substituted group is the same or different and is selected from the group consisting of a straight or branched alkyl, alkenyl, or alkynyl, a cyclic or alicyclic group having from one to six carbon atoms, a heterocyclic group having from one to six carbon atoms, an alkoxy group, an aryloxy group, an alkyloxyaryloxy group, an aryl group, an amine, a halogen, a phenol, a naphthalene, a piperidine, a pyrrole, a ketone, a methylalkyl ketone, and a trifluoromethyl ketone, and wherein each of said substituents may itself be substituted, and wherein any of said substituents may be optionally attached by a $CH_2$ bridge, and wherein the substituent may be optionally partially or completely saturated or unsaturated when it is not represented by said halogen;

wherein (i) and (j) may optionally be attached to Y via a $CH_2$ bridge;

$R_3$ comprises one of (a) a hydrogen (H), (b) a halogen, (c) an alkyl having from one to ten carbon atoms and having a straight or a branched configuration, and wherein the alkyl is partially or completely saturated; (d) an $NH_2$, (e) an $NHR_7$, (f) an $NR_7R_8$, (g) an OH, (h) an OR, (i) an SH, and (j) an SR, and wherein R comprises one of $R_1$, and wherein $R_7$ and $R_8$ may be the same or different and comprise one of $R_1$;

$R_4$ comprises one of (a) $R_1$, (b) a halogen, (c) a mono-, di-, tri- or tetra-substituted alkyl, and (d) an alkyloxy, and wherein $R_1$ is H or a lower alkyl and $R_2$ is H or a lower alkyl then $R_4$ comprises one of (a) a $NR_6R_7$, (b) a $SR_6$, (c) a $OR_6$, and (d) a $CHR_6R_7$, wherein $R_6$ and $R_7$ may be the same or different and comprise one of $R_1$ and $R_2$;

$R_5$ comprises one of $R_1$;

$R_6$ comprises one of $R_1$;

X comprises one of (a) $NR_4$, (b) an oxygen (O), and (c) $R_7CR_4$; and

Y comprises one of (a) a nitrogen (N), (b) an oxygen (O), (c) a sulfur (S), and (d) a $CR_6$, wherein $R_6$ comprises one of $R_1$ and $R_3$, and wherein when Y comprises O or S then $R_2$ is absent (i.e. is zero). In another embodiment of this invention, this method comprises providing the compound having Formula III, as described herein, wherein $R_5$, $R_6$, and $R_3$ are the same moiety, or wherein the compound of Formula III, as described herein, comprises wherein $R_7$, $R_4$, $R_6$, and $R_5$ are each a moiety comprising $R_1$.

As used herein, the term "patient" means members of the animal kingdom, including, but not limited to, human beings. As used herein, the term "having cancer" means that the patient has been diagnosed with cancer.

As used herein, the term "therapeutically effective amount" refers to that amount of any of the present compounds required to bring about a desired effect in a patient. The desired effect will vary depending on the illness being treated. For example, the desired effect may be reducing tumor size, destroying cancerous cells, and/or preventing metastasis, any one of which may be the desired therapeutic response. On its most basic level, a therapeutically effective amount is that amount needed to inhibit the mitosis of a cancerous cell or to facilitate the reversal of multidrug resistance, particularly, for example due to P-glycoprotein, (ie. an effective mitotic inhibitory amount). Any amount of mitotic inhibition or reversal of multidrug resistance will yield a benefit to a patient and is therefore within the scope of the invention.

In another embodiment of this invention, a method of treating a patient having cancer is provided comprising administering to the patient a therapeutically effective amount of a compound of Formula IV, or a pharmaceutical acceptable salt, prodrug, solvate, or hydrate of the compound of Formula IV:

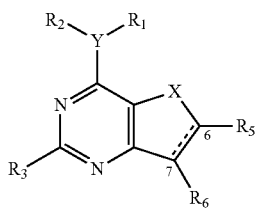

IV and 6,7-saturated and unsaturated wherein the five membered ring may be saturated or unsaturated with respect to bond 6-7;

$R_1$ and $R_2$ may be the same or different and comprises one of (a) a hydrogen (H), (b) an alkyl having from one to ten carbon atoms and having a straight or branched configuration, and wherein the alkyl is partially or completely saturated, or a substituted alkyl having from one to ten carbon atoms, (c) a cycloalkyl having from three to ten carbon atoms, or a substituted cycloalkyl having from three to ten carbon atoms, (d) an alkylcycloalkyl, or a substituted alkylcycloalkyl, (e) an aryl, or a substituted aryl, (f) an alkylaryl, or a substituted alkylaryl (g) a heteroaryl, or a substituted heteroaryl, (h) an alkylheteroaryl, or a substituted alkylheteroaryl, (i) an aromatic, or a substituted aromatic, and (j) a heteroaromatic, or a substituted heteroaromatic, and wherein each substituent of any said substituted group is the same or different and is selected from the group consisting of a straight or branched alkyl, alkenyl, or alkynyl, a cyclic or alicyclic group having from one to six carbon atoms, a heterocyclic group having from one to six carbon atoms, an alkoxy group, an aryloxy group, an alkyloxyaryloxy group, an aryl group, an amine, a halogen, a phenol, a naphthalene, a piperidine, a pyrrole, a ketone, a methylalkyl ketone, and a trifluoromethyl ketone, and wherein each of said substituents may itself be substituted, and wherein any of said substituents may be optionally attached by a $CH_2$ bridge, and wherein the substituent may be optionally partially or completely saturated or unsaturated when it is not represented by said halogen;

wherein (i) and (j) may optionally be attached to Y via a $CH_2$ bridge;

$R_3$ comprises one of (a) a hydrogen (H), (b) a halogen, (c) an alkyl having from one to ten carbon atoms and having a straight or a branched configuration, and wherein the alkyl is partially or completely saturated; (d) an $NH_2$, (e) an $NHR_7$, (f) an $NR_7R_8$, (g) an OH, (h) an $OR$, (i) an SH, and (j) an SR, and wherein R comprises one of $R_1$, and wherein $R_7$ and $R_8$ may be the same or different and comprise one of $R_1$;

$R_4$ comprises one of (a) $R_1$, (b) a halogen, (c) a mono-, di-, tri- or tetra-substituted alkyl, and (d) an alkyloxy, and wherein $R_1$ is H or a lower alkyl and $R_2$ is H or a lower alkyl then $R_4$ comprises one of (a) a $NR_6R_7$, (b) a $SR_6$, (c) a $OR_6$, and (d) a $CHR_6R_7$, wherein $R_6$ and $R_7$ may be the same or different and comprise one of $R_1$ and $R_2$;

$R_5$ comprises one of $R_1$;

$R_6$ comprises one of $R_1$;

X comprises one of (a) $NR_4$, (b) an oxygen (O), and (c) $R_7CR_4$; and

Y comprises one of (a) a nitrogen (N), (b) an oxygen (O), (c) a sulfur (S), and (d) a $CR_6$, wherein $R_6$ comprises one of $R_1$ and $R_3$, and wherein when Y comprises O or S then $R_2$ is absent (i.e. is zero). Other embodiments of the present invention provide for this method including providing the compound having Formula IV, as described herein, comprising wherein $R_5$, $R_6$, and $R_3$ are the same moiety, or wherein $R_6$, and $R_5$ are the same moiety and comprise one of $R_1$.

Compounds of the present invention covered under Formula III and IV may also be administered with one or more additional treatment agents, i.e., a chemotherapeutic agent. Suitable candidates for the additional chemotherapeutic agent include for example but are not limited to, paclitaxel, docetaxel, vinca alkaloids, colchicines, colcemid, cisplatin, and nocadazol. The presence of the compound of the present invention shall enhance the effectiveness of the chemotherapeutic agent by facilitating the reversal of multidrug resistance, particularly due to Pgp, and at least partially restoring the sensitivity of tumors to antimitotic agents.

In yet another embodiment of this invention, a method for inhibiting the mitosis of one or more cancerous cells is provided comprising subjecting one or more live cancerous cells to an effective inhibitory amount of a compound of Formula III, or a salt, prodrug, solvate, or hydrate of a compound of Formula III:

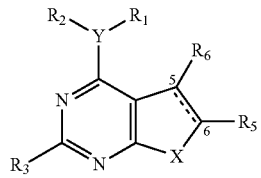

III and 5,6-saturated and unsaturated wherein the five membered ring may be saturated or unsaturated with respect to bond 5-6;

$R_1$ and $R_2$ may be the same or different and comprises one of (a) a hydrogen (H), (b) an alkyl having from one to ten carbon atoms and having a straight or branched configuration, and wherein the alkyl is partially or completely saturated, or a substituted alkyl having from one to ten carbon atoms, (c) a cycloalkyl having from three to ten carbon atoms, or a substituted cycloalkyl having from three to ten carbon atoms, (d) an alkylcycloalkyl, or a substituted alkylcycloalkyl, (e) an aryl, or a substituted aryl, (f) an alkylaryl, or a substituted alkylaryl (g) a heteroaryl, or a substituted heteroaryl, (h) an alkylheteroaryl, or a substituted alkylheteroaryl, (i) an aromatic, or a substituted aromatic, and (j) a heteroaromatic, or a substituted heteroaromatic, and wherein each substituent of any said substituted group is the same or different and is selected from the group consisting of a straight or branched alkyl, alkenyl, or alkynyl, a cyclic or alicyclic group having from one to six carbon atoms, a heterocyclic group having from one to six carbon atoms, an alkoxy group, an aryloxy group, an alkyloxyaryloxy group, an aryl group, an amine, a halogen, a phenol, a naphthalene, a piperidine, a pyrrole, a ketone, a methylalkyl ketone, and a trifluoromethyl ketone, and wherein each of said substituents may itself be substituted, and wherein any of said substituents may be optionally attached by a $CH_2$ bridge, and wherein the substituent may be optionally partially or completely saturated or unsaturated when it is not represented by said halogen;

wherein (i) and (j) may optionally be attached to Y via a $CH_2$ bridge;

$R_3$ comprises one of (a) a hydrogen (H), (b) a halogen, (c) an alkyl having from one to ten carbon atoms and having a straight or a branched configuration, and wherein the alkyl is partially or completely saturated; (d) an $NH_2$, (e) an $NHR_7$, (f) an $NR_7R_8$, (g) an OH, (h) an OR, (i) an SH, and (j) an SR, and wherein R comprises one of $R_1$, and wherein $R_7$ and $R_8$ may be the same or different and comprise one of $R_1$;

$R_4$ comprises one of (a) $R_1$, (b) a halogen, (c) a mono-, di-, tri- or tetra-substituted alkyl, and (d) an alkyloxy, and wherein $R_1$ is H or a lower alkyl and $R_2$ is H or a lower alkyl then $R_4$ comprises one of (a) a $NR_6R_7$, (b) a $SR_6$, (c) a $OR_6$, and (d) a $CHR_6R_7$, wherein $R_6$ and $R_7$ may be the same or different and comprise one of $R_1$ and $R_2$;

$R_5$ comprises one of $R_1$;

$R_6$ comprises one of $R_1$;

X comprises one of (a) $NR_4$, (b) an oxygen (O), and (c) $R_7CR_4$; and Y comprises one of (a) a nitrogen (N), (b) an oxygen (O), (c) a sulfur (S), and (d) a $CR_6$, wherein $R_6$ comprises one of $R_1$ and $R_3$, and wherein when Y comprises O or S then $R_2$ is absent (i.e. is zero), for effecting the inhibition of mitosis of the cancerous cells.

Another embodiment of this invention provides a method for inhibiting the mitosis of one or more cancerous cells comprising subjecting live cancerous cells to an effective mitotic inhibitory amount of a compound of Formula IV, or a salt, prodrug, solvate or hydrate of a compound of Formula IV:

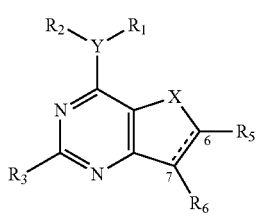

IV and 6,7-saturated and unsaturated wherein the five membered ring may be saturated or unsaturated with respect to bond 6-7;

$R_1$ and $R_2$ may be the same or different and comprises one of (a) a hydrogen (H), (b) an alkyl having from one to ten carbon atoms and having a straight or branched configuration, and wherein the alkyl is partially or completely saturated, or a substituted alkyl having from one to ten carbon atoms, (c) a cycloalkyl having from three to ten carbon atoms, or a substituted cycloalkyl having from three to ten carbon atoms, (d) an alkylcycloalkyl, or a substituted alkylcycloalkyl, (e) an aryl, or a substituted aryl, (f) an alkylaryl, or a substituted alkylaryl (g) a heteroaryl, or a substituted heteroaryl, (h) an alkylheteroaryl, or a substituted alkylheteroaryl, (i) an aromatic, or a substituted aromatic, and (j) a heteroaromatic, or a substituted heteroaromatic, and wherein each substituent of any said substituted group is the same or different and is selected from the group consisting of a straight or branched alkyl, alkenyl, or alkynyl, a cyclic or alicyclic group having from one to six carbon atoms, a heterocyclic group having from one to six carbon atoms, an alkoxy group, an aryloxy group, an alkyloxyaryloxy group, an aryl group, an amine, a halogen, a phenol, a naphthalene, a piperidine, a pyrrole, a ketone, a methylalkyl ketone, and a trifluoromethyl ketone, and wherein each of said substituents may itself be substituted, and wherein any of said substituents may be optionally attached by a $CH_2$ bridge, and wherein the substituent may be optionally partially or completely saturated or unsaturated when it is not represented by said halogen;

wherein (i) and (j) may optionally be attached to Y via a $CH_2$ bridge;

$R_3$ comprises one of (a) a hydrogen (H), (b) a halogen, (c) an alkyl having from one to ten carbon atoms and having a straight or a branched configuration, and wherein the alkyl is partially or completely saturated; (d) an $NH_2$, (e) an $NHR_7$, (f) an $NR_7R_8$, (g) an OH, (h) an OR, (i) an SH, and (j) an SR, and wherein R comprises one of $R_1$, and wherein $R_7$ and $R_8$ may be the same or different and comprise one of $R_1$;

$R_4$ comprises one of (a) $R_1$, (b) a halogen, (c) a mono-, di-, tri- or tetra-substituted alkyl, and (d) an alkyloxy, and wherein $R_1$ is H or a lower alkyl and $R_2$ is H or a lower alkyl then $R_4$ comprises one of (a) a $NR_6R_7$, (b) a $SR_6$, (c) a $OR_6$, and (d) a $CHR_6R_7$, wherein $R_6$ and $R_7$ may be the same or different and comprise one of $R_1$ and $R_2$;

$R_5$ comprises one of $R_1$;

$R_6$ comprises one of $R_1$;

X comprises one of (a) a $NR_4$, (b) an oxygen (O), and (c) $R_7CR_4$; and

Y comprises one of (a) a nitrogen (N), (b) an oxygen (O), (c) a sulfur (S), and (d) a $CR_6$, wherein $R_6$ comprises one of $R_1$ and $R_3$, and wherein when Y comprises O or S then $R_2$ is absent (i.e is zero), for effecting the inhibition of mitosis of the cancerous cells.

As used herein, the term "lower alkyl" group refers to those lower alkyl groups having one to about ten carbon atoms, such as for example methyl, ethyl, propyl, butyl, pentyl, hexyl, cyclopropyl, cyclobutyl, cyclohexyl, cyclopropylmethyl or cyclobutylmethyl groups. Alkyl groups sharing one to about six carbon atoms are preferred. These lower alkyl groups are straight chain, branched chain or cyclic (alicyclic hydrocarbon) arrangements. The carbon atoms of these straight chain, branched chain or cyclic arranged alkyl groups may have one or more substituents for the hydrogens attached to the carbon atoms.

As used herein, the term "heteroalkyl" refers to alkyl chains from one to about 3 atoms where one or more of the carbons has been replaced with nitrogen, oxygen or sulfur, Thus "heteroalkyl" groups will include, for example, C—C—N, C—S, S—C, C—O, C—C—O, O—C, N—C—C, N—C≡C and other various combinations, as will be apparent to one skilled in the art. The above list is not meant to be exhaustive, and many combinations are contemplated as within the scope of the present invention.

The term "aryl" groups, as used herein, refers to compounds whose molecules have an aromatic ring structure, such as the six-carbon ring of benzene, or multiple rings which are either fused or unfused, such as condensed six-carbon rings of other aromatic derivatives. The term "aryl" is also defined to include diaryl, triaryl and polyaryl groups, which would have two, three or more rings, respectively. Thus, suitable aryl groups would include, for example, phenyl, biphenyl, naphthyl, phenanthrene, anthracene groups and aryl oxyaryl groups. This list is not meant to be exhaustive, and any aryl group, as these terms are defined above and commonly understood in the art, are within the scope of the present invention.

The term "heteroaryl" refers to aromatic ring structures having at least one atom in the ring which is not carbon, such as oxygen, nitrogen or sulfur. "Heteroaryls" as used herein also refers to aromatic ring structures that are part of larger ring structures, such as two or three member ring systems, which may be fused or unfused, in which one of the rings is as described above. Thus, "heteroaryl" refers to ring systems in which one or more rings contain a heteroatom and one or more rings do not. It will be understood that this list is not meant to be exhaustive, and that any heteroaryl group, as these terms are defined above and commonly understood in the art, are within the scope of the present invention. The heteroaryl ring systems may be fused ring systems or unfused. Examples of heteroaryl ring systems include, for example but are are not limited to, pyridine, quinoline, isoquinoline, pyrrole, thiophenes, furans, imidazoles, and the like, as well as fused ring structures having rings of different sizes, such as benzofurans, indoles, purines, and the like.

Also included within the scope of the present invention are alicyclic groups, as that term is understood in the art, and heterocyclic groups. As used herein, the term "heterocyclic group" refers to non-aromatic cyclic substituents in which one or more members of the ring is not carbon, for example oxygen, sulfur or nitrogen.

The terms "alkylaryl" (or "alkaryl") or "alkylheteroaryl" as used herein refer to groups having an alkyl moiety attached to an aryl or heteroaryl ring. The alkyl moiety is preferably a straight, branched or cyclic alkyl group having one to about six carbon atoms. This alkyl moiety may also contain oxygen, nitrogen or sulfur, and therefore may be an alkoxy group. The aryl or heteroaryl moiety of the alkylaryl group is a substituted or unsubstituted aryl or heteroaryl group, as these terms are described above. As used herein, the terms "alkylaryl" or "alkylheteroaryl" will also be used to refer to arylalkyl groups or heteroarylalkyl groups, as those terms are understood in the art, and denotes attachment of such a substituent at either the alkyl or the aryl portion of the group. Thus, for example, a benzyl group would be embraced by the term "alkylaryl".

Any of the cyclic substituents described above, such as the aryl, heteroaryl, alkylaryl, alkylheteroaryl, alicyclic, or heterocyclic groups are optionally substituted with one or more substituents as listed above. In the case of more than one substituent, the substituents are independently selected. "Alkoxy groups" and "alkyl groups" include straight or branched chains having up to about ten members. "Halogen" refers to chlorine, bromine, iodine and fluorine. "Aryl and heteroaryl groups" are as described above. When a carboxylic acid is a substituent, it will be appreciated that the moiety represents an acid such as benzoic acid.

As used herein, the terms "aroyl" or "heteroaroyl", such as when used within the term p-aroyl-L-glutamate, refers to benzoyl, napthoyl, thiophenoyl, furophenoyl, pyrroyl, and any other "aroyl" or "heteroaroyl" as these terms would be understood by one skilled in the art. "Aroyl" and "heteroaroyl" are generally defined in the art as an aromatic or heteroaromatic compound having a carbonyl moiety. As used herein, the term "glutamate" will be understood as representing both the ester form (glutamate) and the acid form (glutamic acid).

It will appreciated by those skilled in the art that a general formula depicting compounds having side chains with adjacent carbons having a double bond will result in both cis and trans isomers as possible structures. Both the cis and trans isomers, and mixtures thereof, of any such compound within the broad general formula described in Formulas III and IV are contemplated as being within the scope of the present invention.

A preferred form of Formula IV is shown in FIG. 3, Sample ID AAG12.

In a more preferred embodiment of this invention, a compound of Formula III:

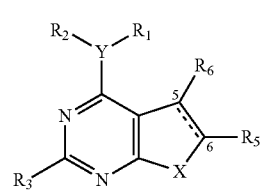

and 5,6-saturated and unsaturated
with respect to the five membered ring;

$R_1$ and $R_2$ may be the same or different and each is one of (a) a hydrogen (H), (b) an alkyl having from one to ten carbon atoms and having a straight or branched configuration, and wherein the alkyl is partially or completely saturated, or a substituted alkyl having from one to ten carbon atoms, (c) a cycloalkyl having from three to ten carbon atoms, or a substituted cycloalkyl having from three to ten carbon atoms, (d) an alkylcycloalkyl, or a substituted alkylcycloalkyl, (e) an aryl, or a substituted aryl, (f) an alkylaryl, or a substituted alkylaryl (g) a heteroaryl, or a substituted heteroaryl, (h) an alkylheteroaryl, or a substituted alkylheteroaryl, (i) an aromatic, or a substituted aromatic, and (j) a heteroaromatic, or a substituted heteroaromatic, and wherein each substituent of any said substituted group is the same or different and is selected from the group consisting of a straight or branched alkyl, alkenyl, or alkynyl, a cyclic or alicyclic group having from one to six carbon atoms, a heterocyclic group having from one to six carbon atoms, an alkoxy group, an aryloxy group, an alkyloxyaryloxy group, an aryl group, an amine, a halogen, a phenol, a naphthalene, a piperidine, a pyrrole, a ketone, a methylalkyl ketone, and a trifluoromethyl ketone, and wherein each of said substituents may itself be substituted, and wherein any of said substituents may be optionally attached by a $CH_2$ bridge, and wherein the substituent may be optionally partially or completely saturated or unsaturated when it is not represented by said halogen;

wherein (i) and (j) may optionally be attached to Y via a CH$_2$ bridge;

wherein R$_1$ and R$_2$ are not each hydrogen (H) when Y is N;

R$_3$ is one of (a) a hydrogen (H), (b) a halogen, (c) an alkyl having from one to ten carbon atoms and having a straight or a branched configuration, and wherein the alkyl is partially or completely saturated; (d) an NH$_2$, (e) an NHR$_7$, (f) an NR$_7$R$_8$, (g) an OH, (h) an OR, (i) an SH, and (j) an SR, and wherein R is one of R$_1$, and wherein R$_7$ and R$_8$ may be the same or different and is one of R$_1$;

R$_5$ is one of R$_1$, except when R$_6$ is a hydrogen (H), heteroaryl, or phenyl, wherein the phenyl and heteroaryl are optionally substituted with 1-2 moieties independently selected from the group consisting of halogen, (C$_1$-C$_4$)alkyl, (C$_1$-C$_4$)fluoroalkyl, (C$_1$-C$_4$)alkoxy, (C$_1$-C$_4$)alkylamine, and (C$_1$-C$_4$)dialkylamine, then R$_5$ is not (i) a hydrogen (H), or (ii) a phenyl group substituted at any position with a substituent selected from the group consisting of (a) a hydrogen, (b) a halogen, (c) CN, (d) OH, (e) NH$_2$, (f) (C$_1$-C$_4$)alkyl, (g) (C$_3$-C$_6$)cycloalkyl, (h) (C$_1$-C$_4$)fluoroalkyl, (i) (C$_1$-C$_4$)alkoxy, (j) (C$_1$-C$_4$)alkylamine, (k) (C$_1$-C$_4$)dialkylamine, (l) C(O)OH, (m) C(O)—NH$_2$, (n) C(O)—(C$_1$-C$_4$)alkyl, (O)C(O)—(C$_1$-C$_4$)fluoroalkyl, (p) C(O)—(C$_1$-C$_4$)alkylamine, and (q) C(O)—(C$_1$-C$_4$)alkoxy;

R$_6$ is one of R$_1$;

X is a carbon (C) or a CR$_4$; and

Y is one of (a) a nitrogen (N), (b) an oxygen (O), (c) a sulfur (S), and (d) a CR$_6$, wherein R$_6$ is one of R$_1$ and R$_3$ except when Y is CR$_6$ then said R$_6$ is not H when R$_1$ and R$_2$ are each H, and wherein when Y is O or S then R$_2$ is absent or is zero. Further, this invention provides for the compound of Formula III comprising pharmaceutically acceptable salts, hydrates, and solvates thereof. More preferably, this invention provides for a compound of Formula III, as described herein, wherein R$_1$ is either a hydrogen or said alkyl having from one to ten carbon atoms and R$_2$ is a substituted naphthyl, or wherein R$_1$ is a substituted naphthyl and R$_2$ is either a hydrogen or said alkyl having from one to ten carbon atoms. Most preferably, this invention provides the compound of Formula III wherein the substituted naphthyl is a methoxynaphthyl group and wherein the 5,6 bond is a single bond.

Another embodiment of this invention provides a compound comprising Formula IV:

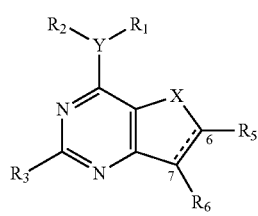

IV and 6,7-saturated and unsaturated wherein R$_1$ and R$_2$ may be the same or different and comprises one of (a) a hydrogen (H), (b) an alkyl having from one to ten carbon atoms and having a straight or branched configuration, and wherein the alkyl is partially or completely saturated, or a substituted alkyl having from one to ten carbon atoms, (c) a cycloalkyl having from three to ten carbon atoms, or a substituted cycloalkyl having from three to ten carbon atoms, (d) an alkylcycloalkyl, or a substituted alkylcycloalkyl, (e) an aryl, or a substituted aryl, (f) an alkylaryl, or a substituted alkylaryl (g) a heteroaryl, or a substituted heteroaryl, (h) an alkylheteroaryl, or a substituted alkylheteroaryl, (i) an aromatic, or a substituted aromatic, and (j) a heteroaromatic, or a substituted heteroaromatic, and wherein each substituent of any said substituted group is the same or different and is selected from the group consisting of a straight or branched alkyl, alkenyl, or alkynyl, a cyclic or alicyclic group having from one to six carbon atoms, a heterocyclic group having from one to six carbon atoms, an alkoxy group, an aryloxy group, an alkyloxyaryloxy group, an aryl group, an amine, a halogen, a phenol, a naphthalene, a piperidine, a pyrrole, a ketone, a methylalkyl ketone, and a trifluoromethyl ketone, and wherein each of said substituents may itself be substituted, and wherein any of said substituents may be optionally attached by a CH$_2$ bridge, and wherein the substituent may be optionally partially or completely saturated or unsaturated when it is not represented by said halogen;

wherein (i) and (j) may optionally be attached to Y via a CH$_2$ bridge;

R$_3$ comprises one of (a) a hydrogen (H), (b) a halogen, (c) an alkyl having from one to ten carbon atoms and having a straight or a branched configuration, and wherein the alkyl is partially or completely saturated; (d) an NH$_2$, (e) an NHR$_7$, (f) an NR$_7$R$_8$, (g) an OH, (h) an OR, (i) an SH, and (j) an SR, and wherein R comprises one of R$_1$, and wherein R$_7$ and R$_8$ may be the same or different and comprise one of R$_1$;

R$_4$ comprises one of (a) R$_1$, (b) a halogen, (c) a mono-, di-, tri- or tetra-substituted alkyl, and (d) an alkyloxy, and wherein R$_1$ is H or a lower alkyl and R$_2$ is H or a lower alkyl then R$_4$ comprises one of (a) a NR$_6$R$_7$, (b) a SR$_6$, (c) a OR$_6$, and (d) a CHR$_6$R$_7$, wherein R$_6$ and R$_7$ may be the same or different and comprise one of R$_1$ and R$_2$;

R$_5$ comprises one of R$_1$;

R$_6$ comprises one of R$_1$;

X is a carbon (C) or a CR$_4$; and

Y comprises one of (a) a nitrogen (N), (b) an oxygen (O), (c) a sulfur (S), and (d) a CR$_6$, wherein R$_6$ comprises one of R$_1$ and R$_3$. Further, this invention provides for a compound of Formula IV comprising pharmaceutically acceptable salts, solvates, and hydrates thereof. More preferably, this invention provides for the compound of Formula IV, as described herein, wherein R$_1$ is either a hydrogen or said alkyl having from one to ten carbon atoms and R$_2$ is a substituted naphthyl, or wherein R$_1$ is a substituted naphthyl and R$_2$ is either a hydrogen or said alkyl having from one to ten carbon atoms. Most preferably, this invention provides for a compound of Formula IV, as described herein, wherein said substituted naphthyl is a methoxynaphthyl.

Proliferative diseases and/or disorders that may be treated according to the methods of the present invention include, without limitation, leukemia, non-small cell lung cancer, colon cancer, central nervous system (CNS) cancer, melanoma, ovarian cancer, renal cancer, prostate cancer, and breast cancer.

It is especially advantageous to formulate parenteral compositions in dosage unit form for ease of administration and uniformity of dosage. Dosage unit form as used herein refers to physically discrete units suited as unitary dosages for the patients being treated, each unit containing a predetermined quantity or effective amount of a tricyclic compound of the present invention to produce the desired effect in association with a pharmaceutical carrier. The specification for the dosage unit forms of the invention are dictated by and directly dependent on the particular compound and the particular effect, or therapeutic response, that is desired to be achieved.

Compounds containing Formula III or Formula IV, or pharmaceutically acceptable salts, prodrugs, solvates, or hydrates thereof, can be administered to a patient (an animal or human) via various routes including parenterally, orally or intraperitoneally. Parenteral administration includes the following routes that are outside the alimentary canal (digestive tract): intravenous; intramuscular; interstitial, intraarterial; subcutaneous; intraocular; intracranial; intraventricular; intrasynovial; transepithelial, including transdermal, pulmonary via inhalation, ophthalmic, sublingual and buccal; topical, including dermal, ocular, rectal, or nasal inhalation via insufflation or nebulization. Specific modes of administration shall depend on the indication. The selection of the specific route of administration and the dose regimen is to be adjusted or titrated by the clinician according to methods known to the clinician in order to obtain the optimal clinical response. The amount of compound to be administered is that amount which is therapeutically effective. The dosage to be administered to a patient shall depend on the characteristics of the patient being treated, including for example, but not limited to, the patient's age, weight, health, and types and frequency of concurrent treatment, if any, of any other chemotherapeutic agent(s), all of which is determined by the clinician as one skilled in the art.

Compounds containing Formula III or Formula IV, or a pharmaceutically acceptable salt, prodrug, solvate or hydrate thereof, that are orally administered can be enclosed in hard or soft shell gelatin capsules, or compressed into tablets. Compounds also can be incorporated with an excipient and used in the form of ingestible tablets, buccal tablets, troches, capsules, sachets, lozenges, elixirs, suspensions, syrups, wafers and the like. Compounds containing Formula III or Formula IV can be in the form of a powder or granule, a solution or suspension in an aqueous liquid or non-aqueous liquid, or in an oil-in-water emulsion.

The tablets, troches, pills, capsules and the like also can contain, for example, a binder, such as gum tragacanth, acacia, corn starch; gelating excipients, such as dicalcium phosphate; a disintegrating agent, such as corn starch, potato starch, alginic acid and the like; a lubricant, such as magnesium stearate; a sweetening agent, such as sucrose, lactose or saccharin; or a flavoring agent. When the dosage unit form is a capsule, it can contain, in addition to the materials described above, a liquid carrier. Various other materials can be present as coatings or to otherwise modify the physical form of the dosage unit. For example, tablets, pills, or capsules can be coated with shellac, sugar or both. A syrup or elixir can contain the active compound, sucrose as a sweetening agent, methyl and propylparabens as preservatives, a dye and flavoring. Any material used in preparing any dosage unit form should be pharmaceutically pure and substantially non-toxic. Additionally, the compounds of Formula III or Formula IV, or a pharmaceutically acceptable salt, prodrug, solvate or hydrate of said Formulae, can be incorporated into sustained-release preparations and formulations.

The compounds of Formula III or Formula IV, or a pharmaceutically acceptable salt, prodrug, solvate or hydrate thereof, can be administered to the central nervous system, parenterally or intraperitoneally. Solutions of the compound as a free base or a pharmaceutically acceptable salt can be prepared in water mixed with a suitable surfactant, such as hydroxypropylcellulose. Dispersions also can be prepared in glycerol, liquid polyethylene glycols and mixtures thereof, and in oils. Under ordinary conditions of storage and use, these preparations can contain a preservative and/or antioxidants to prevent the growth of microorganisms or chemical degeneration.

The pharmaceutical forms suitable for injectable use include, without limitation, sterile aqueous solutions or dispersions and sterile powders for the extemporaneous preparation of sterile injectable solutions or dispersions. In all cases, the form must be sterile and must be fluid to the extent that easy syringability exists. It can be stable under the conditions of manufacture and storage and must be preserved against the contaminating action of microorganisms, such as bacteria and fungi.

Compounds of the present invention may be contained within, mixed with, or associated with, a suitable (acceptable) pharmaceutical carrier for administration to a patient according to the particular route of administration desired. Suitable or acceptable pharmaceutical carriers refer to any pharmaceutical carrier that will solubilize the compounds of the present invention and that will not give rise to incompatability problems, and includes any and all solvents, dispersion media, coatings, antibacterial and antifungal agents, isotonic agents, absorption delaying agents, and the like. The use of such suitable or acceptable pharmaceutical carriers are well known by those skilled in the art. Preferred carriers include sterile water, physiologic saline, and five percent dextrose in water. Examples of other suitable or acceptable pharmaceutical carriers include, but are not limited to, ethanol, polyol (such as propylene glycol and liquid polyethylene glycol), suitable mixtures thereof, or vegetable oils. The proper fluidity can be maintained, for example, by the use of a coating, such as lecithin, by the maintenance of the required particle size (in the case of a dispersion) and by the use of surfactants. The prevention of the action of microorganisms can be brought about by various antibacterial and anti-fungal agents, for example, parabens, chlorobutanol, phenol, sorbic acid, thimerosal, and the like. In many cases, it will be preferable to include isotonic agents, for example, sugars or sodium chloride.

Sterile injectable solutions are prepared by incorporating the compound of Formula III or Formula IV in the required amount in the appropriate solvent with various of the other ingredients enumerated above, as required, followed by filtered sterilization. Generally, dispersions are prepared by incorporating the sterilized compound of Formula III or Formula IV into a sterile vehicle that contains the basic dispersion medium and any of the other ingredients from those enumerated above. In the case of sterile powders for the preparation of sterile injectable solutions, the preferred methods of preparation are vacuum drying and freeze drying.

Pharmaceutical compositions which are suitable for administration to the nose and buccal cavity include, without limitation, self-propelling and spray formulations, such as aerosol, atomizers and nebulizers.

The therapeutic compounds of Formula III and Formula IV, as described herein, can be administered to a patient alone or in combination with pharmaceutically acceptable carriers or as pharmaceutically acceptable salts, solvates or hydrates thereof, the proportion of which is determined by the solubility and chemical nature of the compound, chosen route of administration to the patient and standard pharmaceutical practice.

The present invention is more particularly described in the following non-limiting examples, which are intended to be illustrative only, as numerous modifications and variations therein will be apparent to those skilled in the art.

EXAMPLES

FIG. 1 shows flow cytometric analysis to assess the effect of various bicyclic compounds of the present invention on the cell cycle phase distributions of MDA MB 435 human breast cancer. The percentage of cells in the $G_2/M$ phases were increased approximately two-fold by treatment of the cells for twenty four hours with each of the bicyclic compounds AAG1, AAG12, AAG16, and AAG20, with AAG1 and AAG16 being most potent based upon the 30 nM and 10 nM doses, respectively.

FIG. 2 shows the microtubule depolymerization immunofluorescence assay of an A-10 rat smooth muscle cell line following treatment with various compounds of the present invention, namely, AAG1, AAG7, and AAG16. A-10 rat smooth muscle cells were used since they grow as flat monolayers that are amenable to imaging. The A-10 cells were treated for twenty four (24) hours (h) with EtOH (control), 250 nM (nanomolar) AAG1, 500 nM AAG7, or 40 nM AAG16, respectively. Microtubules were then visualized by indirect immunofluorescence staining with beta-tubulin antibodies. The control cells shown in FIG. 2 displayed extensive microtubule systems with perimeter organizing centers. Treatment with AAG1, AAG7, and AAG16 caused losses of microtubules in the cells. This immunofluorescence assay shows that the bicyclic compounds of the present invention were effective in depolymerizing the tubulin protein microtubule of A-10 cells. Each of the compounds AAG1, AAG7, and AAG16 has potent nanomolar tubulin inhibitory activity. Compounds of the present invention having the structural Formulas III and IV, as set forth herein, inhibit the microtubule dynamics. The inhibition of microtubule dynamics hinders microtubule formation and results in mitotic arrest and initiation of apoptosis or programmed cell death.

The biological effects of various bicyclic compounds of the present invention, namely AAG1, AAG7, AAG12, AAG16, AAG20, and AAG26, as compared to known antimitotic agents Taxol® (Bristol-Myers Squibb Company) and combrestastatin A4, commercially available from Cayman Chemicals, Michigan, USA, are presented in FIG. 4. Antimitotic compounds AAG1, AAG7, AAG12, AAG16, AAG20, and AAG26, Taxol®, and combrestastatin A4, were evaluated for cytotoxity towards the panel of human cell lines MDA MB 435 (human breast cancer), SKOV3 (human ovarian cancer), and SKOV3M6/6 (Pgp infected human ovarian cancer). FIG. 4 shows the $IC_{50}$ of each of these antimitotic compounds towards each cancer cell line. The $IC_{50}$ is the inhibitory concentration required to effectuate fifty percent inhibition of cell growth. FIG. 4 shows that the compounds of the present invention, AAG1, AAG7, AAG12, AAG16, AAG20, and AAG26, have cytotoxic activity toward each of the human cancer cell lines tested. Although Taxol® and combrestastatin A4 were more potent than compounds AAG1, AAG7, AAG12, AAG16, AAG20, and AAG26 in the MDA MB 435 and the SKOV3 sensitive cell lines, Taxol® was subject to tumor resistance due to the overexpression of P-glycoprotein (Pgp) in the ovarian cancer cell line SKOV3M6/6. FIG. 4 shows the $IC_{50}$ values of 171 nanoM (nM) for AAG1 and 4.4 microM (µM) for Taxol® toward the Pgp infected human ovarian cancer cell line SKOV3M6/6. FIG. 4 shows the calculated relative resistance value of 4.7 for compound AAG1 and a relative resistance value of 2013 for Taxol®. FIG. 4 shows the $IC_{50}$ values of 8.4 nM and 3.2 nM for AAG16 and AAG26, respectively, and 4.4 microM for Taxol® toward the Pgp infected human ovarian cancer cell line. Thus, the results confirm that overexpression of Pgp did not effect cell sensitivity to compounds of the present invention AAG3 of the present invention.

FIGS. 5a and 5b show the results of testing compound AAG1 of the present invention using National cancer Institute (NCI) 55 human tumor lines. The cells lines, which represent leukemia, non-small cell lung cancer, colon cancer, central nervous system cancer, melanoma, ovarian cancer, renal cancer, prostate cancer, and breast cancer, are listed in FIG. 5. Testing was in accordance with the NCI Developmental Therapeutics Program (DTP) In Vitro Cell Line Screening Project (IVCLSP). Methodology for testing under IVCLSP is provided at http://dtp.nci.gov/branches/btb/ivclsp.html.

FIG. 5 shows the tumor cell inhibitory activity, measured by $GI_{50}$ values ($10^{-8}$ M) for AAG1. $GI_{50}$ is the concentration of chemical required to reduce the growth of treated cells to half that of untreated cells (i.e. control). $GI_{50}$ represents the concentration of chemical required to effectuate fifty percent inhibition of cell growth. AAG1 exhibited $GI_{50}$ values of single digit $10^{-8}$ molar levels against all 55 tumor cell lines.

An NCI COMPARE analysis was performed for AAG1 to elucidate a possible mechanism of action by comparing responses of the 55 cell lines to known microtubule-targeting agents. For microtubule specific compounds, the cell type selectivity profile in tumor growth inhibitory (TGI) levels is highly indicative of the compound's mechanism of action. A TGI Correlation value that is equal to or greater than 0.6 is generally considered by those skilled in the art to be a good correlation value for classification as a microtubule targeting agent. The results of the NCI COMPARE analysis for compound AAG1 of the present invention is set forth in Table 1.

TABLE 1

| TGI endpoint TARGET SET: STANDARD_AGENTS_TGI SEED: S747157 -4M TGI 2 days AVGDATA SEED TYPE: NSC_FIVE_DOSE | | | |
| --- | --- | --- | --- |
| Rank | Vector | Correlation | Cell line |
| 1 | vincristine sulfate S67574 -3M TGI 2 days AVGDATA | 0.600 | 49 |
| 2 | maytansine S 153858 -4M TGI 2 days AVGDATA | 0.494 | 49 |
| 3 | vinblastine sulfate S49842 -5.6M TGI 2 days AVGDATA | 0.458 | 49 |
| 4 | homoharringtonine S141633 -4.6M TGI 2 days AVGDATA | 0.455 | 47 |

The NCI COMPARE analysis was performed for AAG1 to elucidate a possible mechanism of action of AAG1 by the similarity response of the cell lines to known compounds. The three compounds that showed the best correlation with AAG1 are all well-known microtubule targeting agents. For microtubule specific compounds, the cell type selectivity profile in TGI level (correlation) is highly indicative of the compounds mechanism of action. Thus AAG1 is a microtubule inhibitor. This COMPARE analysis also indicates that AAG1 acts most like vincristine sulfate (correlation 0.6), which is a well known anticancer agent widely used in the clinic and strongly suggests that AAG1 would be highly active in vivo. The tumor inhibitory data from the NCI preclinical tumor screen also strongly suggest in vivo activity for AAG1.

Figure 6B:
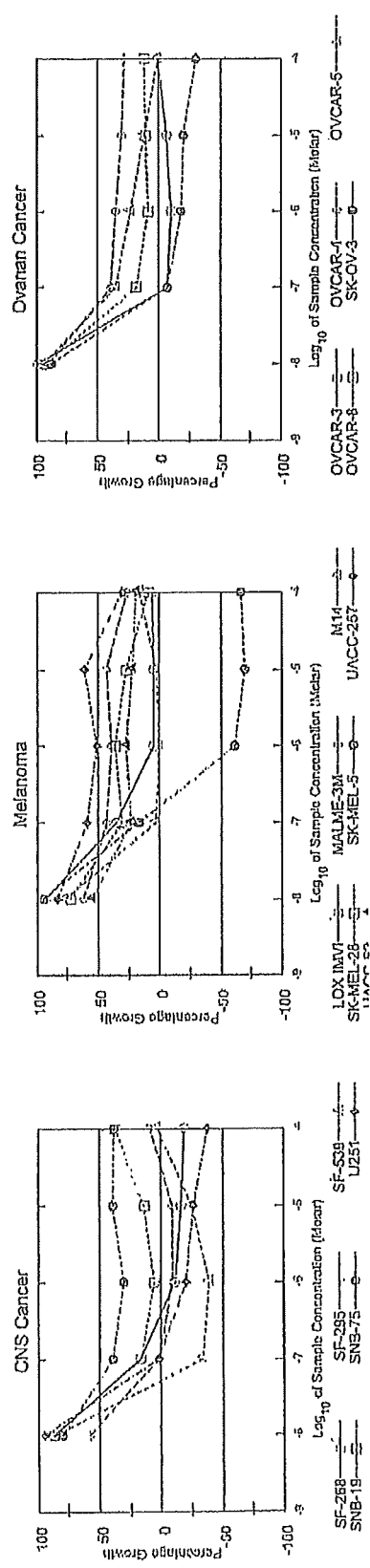
Figure 6C:
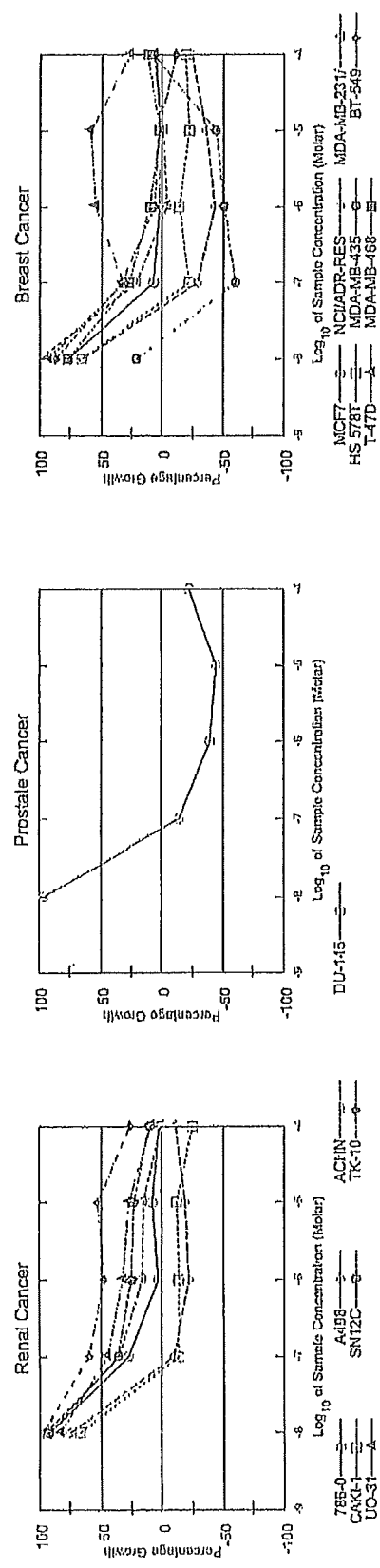

FIGS. 6a, 6b, and 6c show individual dose response curves of percentage growth for each of the cancer cell lines set forth in FIGS. 5a and 5b.

Figure 7:
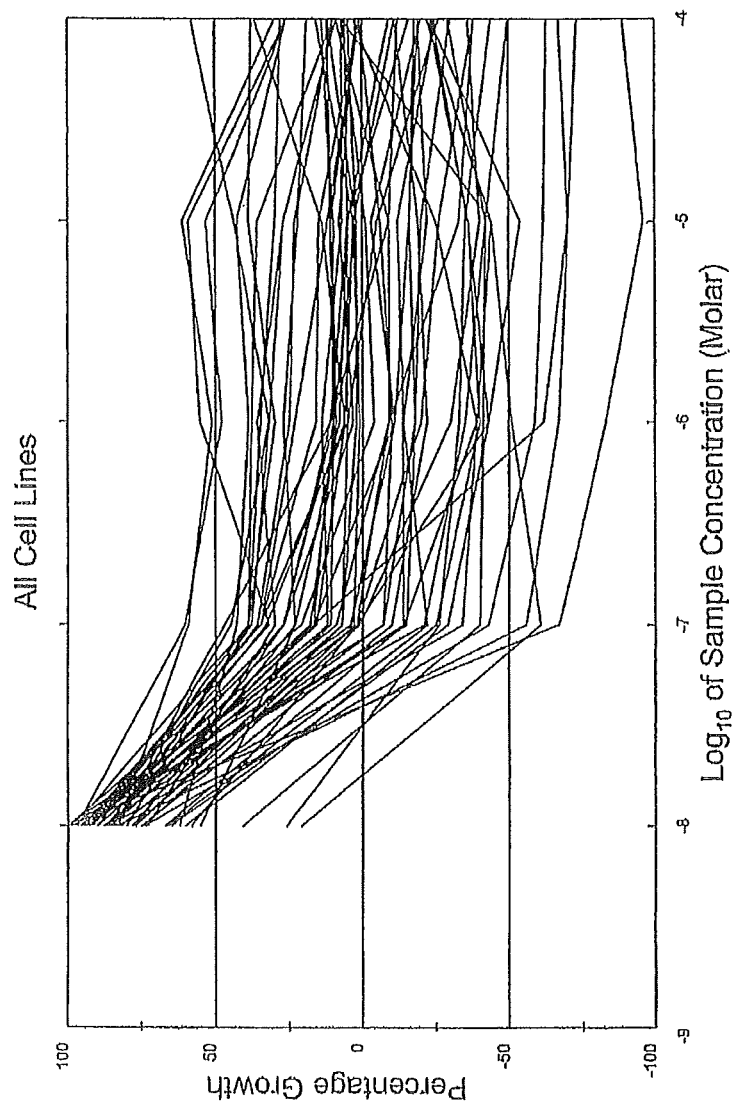
FIG. 7 shows a dose response curve of percentage growth for all of the cell lines shown in FIG. 5.

FIG. 7 shows a dose response curve of percentage growth for all of the cell lines shown in FIGS. 5a and 5b.

Figure 8:
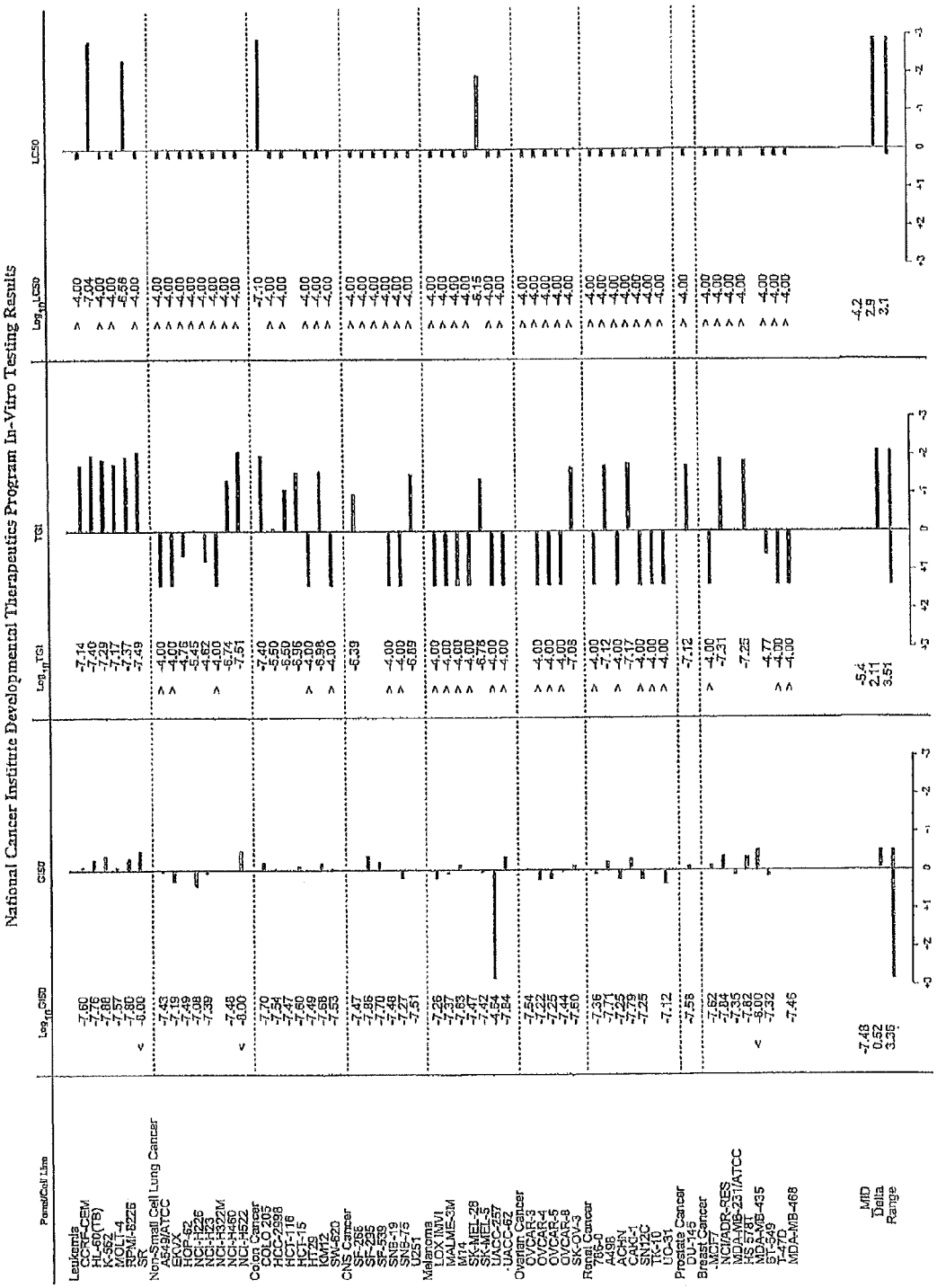
FIG. 8 shows mean graphs for each of the cancer types and corresponding cell lines shown in FIG. 5.

FIG. 8 shows mean graphs for each of the cancer types and corresponding cell lines shown in FIGS. 5a and 5b.

SYNTHESIS OF BICYCLIC COMPOUNDS

Experimental Section

Analytical samples were dried in vacuo (0.2 mm Hg) in a CHEM-DRY drying apparatus over $P_2O_5$ at 80° C. Melting points were determined on a MEL-TEMP II melting point apparatus with FLUKE 51K/J electronic thermometer and are uncorrected. Nuclear magnetic resonance spectra for proton ($^1$H NMR) were recorded on a Bruker WH-400 (400 MHz) spectrometer. The chemical shift values are expressed in ppm (parts per million) relative to tetramethylsilane as an internal standard: s, singlet; d, doublet; t, triplet; q, quartet; m, multiplet; br, broad singlet. Thin-layer chromatography (TLC) was performed on Whatman Sil G/UV254 silica gel plates with a fluorescent indicator, and the spots were visualized under 254 and 366 nm illumination. Proportions of solvents used for TLC are by volume. Column chromatography was performed on a 230-400 mesh silica gel (Fisher, Somerville, N.J.) column. Elemental analyses were performed by Atlantic Microlab, Inc., Norcross, Ga. Element compositions are within ±0.4% of the calculated values. Fractional moles of water or organic solvents frequently found in some analytical samples of antifolates could not be prevented in spite of 24-48 h of drying in vacuo and were confirmed where possible by their presence in the $^1$H NMR spectra. All solvents and chemicals were purchased from Aldrich Chemical Co. or Fisher Scientific and were used as received.

Synthesis of AAG1

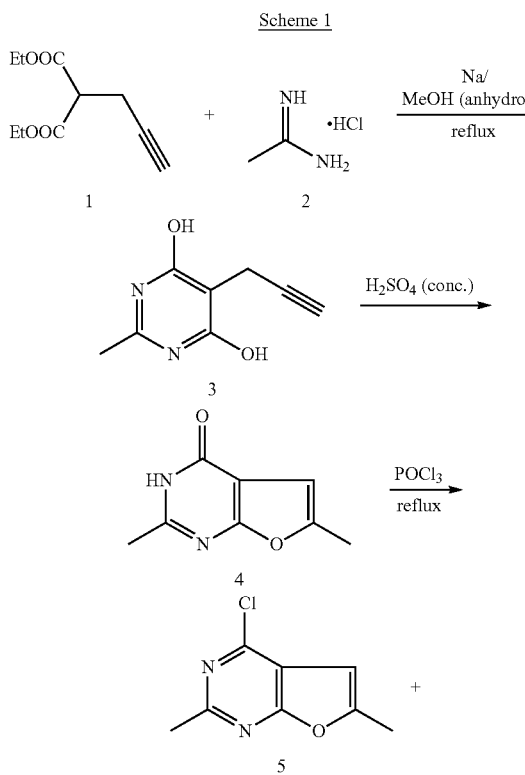

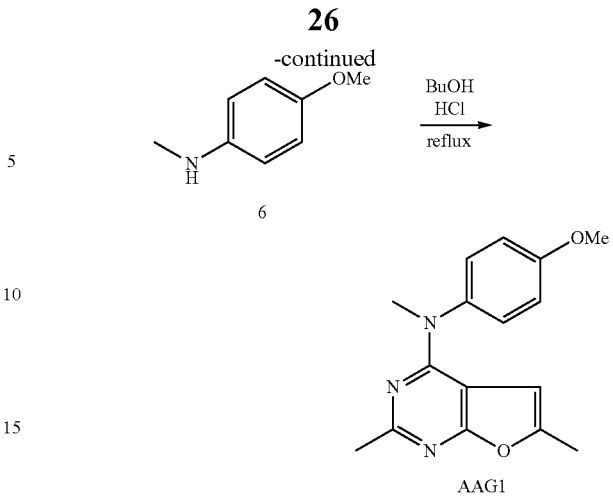

Chemistry:

Dimethyl propargylmalonate 1 reacted with acetamidine hydrochloride 2 and sodium metal in MeOH (anhydrous) at reflux to cyclize the pyrimidine ring and give 3. The use of anhydrous solvent was critical for the success of this reaction. Under cyclization conditions in $H_2SO_4$ (conc.), compound 3 was converted to the furo[2,3-d]pyrimidine 4, which gave the 4-chloro analogue 5 with $POCl_3$. Compound 5 reacted with N-methyl aniline 6 and a trace amount of HCl in BuOH to give AAG1.

Experimental Section for Scheme 1

2-Methyl-5-prop-2-yn-1-ylpyrimidine-4,6-diol (3)

To a 250 mL flask was added 1 (3.96 g, 20 mmol), 2 (1.85 g, 20 mmol) and 50 mL anhydrous MeOH. After 800 mg (20 mmol) Na was added to the solution, yellow precipitate was observed. The resulting mixture was refluxed overnight. The yellow precipitate was collected by filtration and then dissolved in 10 mL $H_2O$. The pH of the resulting solution was adjusted to 6.5 by adding 2 N HCl to afford a yellow precipitate, which was collected by filtration and dried over $P_2O_5$ to afford 1.21 g (37%) of 3: TLC $R_f$ 0.11 ($CHCl_3$/MeOH 6:1); mp>300° C.; $^1$H NMR (DMSO-$d_6$) δ 2.23 (s, 3H), 3.05 (s, 2H), 3.32 (s, 1H), 11.92 (s, 2H).

2,6-Dimethylfuro[2,3-d]pyrimidin-4(3H)-one (4)

To a 50 mL flask was added 3 (1.64 g, 10 mmol) and 15 mL $H_2SO_4$ (conc.). The solution was stirred overnight and poured in to 100 mL distilled water and extracted by 3×30 mL $CHCl_3$. The organic layer was pooled and concentrated to afford 1.36 (83%) of 4 as a yellow powder: TLC $R_f$ 0.35 ($CHCl_3$/MeOH 6:1); mp>300° C.; $^1$H NMR (DMSO-$d_6$) δ 2.42 (s, 3H), 2.44 (s, 3H), 6.63 (s, 1H), 12.50 (s, 1H).

4-Chloro-2,6-dimethylfuro[2,3-d]pyrimidine (5)

To a 50 mL flask was added 4 (1.64 g, 10 mmol) and 10 mL $POCl_3$. The resulting mixture was refluxed for 2 h, and the solvent was removed under reduced pressure to afford a dark residue. To this was added 30 mL of $CHCl_3$ and 3 g of silica gel. The solvent was evaporated to afford a plug. Column chromatography of the plug with hexane: acetyl acetate=20:1 as eluent afford 1.55 g (85%) of 5 as a yellow solid: TLC $R_f$ 0.26 (Hexane/EtOAC 15:1); mp 47.6-48.1° C.; $^1$H NMR (DMSO-$d_6$) δ 2.48 (s, 3H), 2.63 (s, 3H), 6.77 (s, 1H).

N-(4-methoxyphenyl)-N,2,6-trimethylfuro[2,3-d]pyrimidin-4-amine (AAG1)

To a 50 mL flask was added 5 (91 mg, 0.5 mmol), 6 (77 mg, 0.55 mmol) and 5 mL BuOH. To this solution was added 2 drops of concentrate HCl solution and the mixture was refluxed. TLC indicated the disappearance of starting material 5, the solvent was removed under reduced pressure. To the residue obtained was added silica gel and MeOH and the solvent removed to make a plug. This plug was separated by column chromatography to give 106 g (75%) of AGG1 as a white powder: TLC $R_f$ 0.36 (Hexane/EtOAC 3:1); mp 108-109° C.; $^1$H NMR (DMSO-$d_6$) δ 2.14 (s, 3H), 2.45 (s, 3H), 3.43 (s, 3H), 3.81 (s, 3H), 4.55 (s, 1H), 7.04 (d, 2H, J=2.8 Hz), 7.25 (d, 2H, J=2.8 Hz). Anal. ($C_{16}H_{17}N_3O_2$) m/z (ESI) 284.1387 [M+1]$^+$.

Synthesis of AAG 7

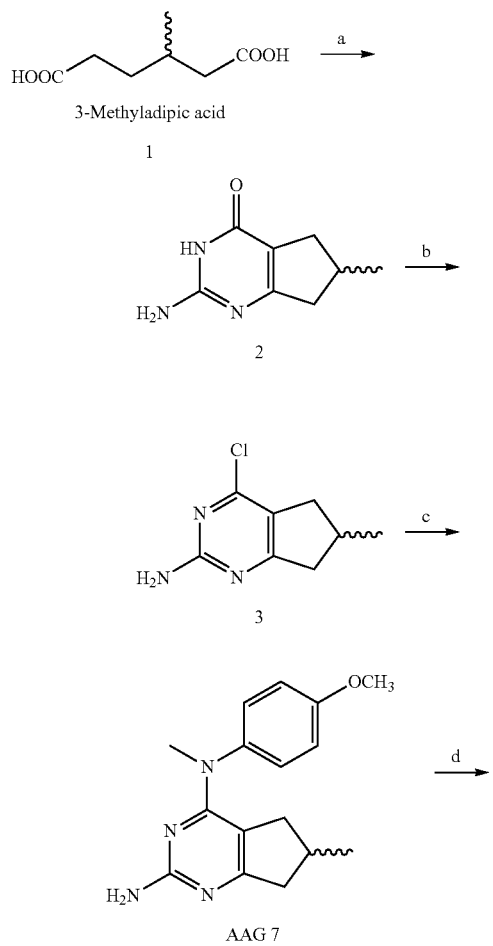

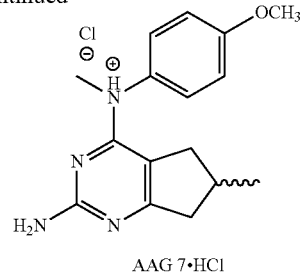

AAG 7·HCl

Conditions: (a) 1) Ethanol, conc. sulfuric acid, reflux, 8 h; 2) Na, toluene, reflux, 3 h; 3) guanidine carbonate, t-BuOH, t-BuOK; (b) POCl$_3$, reflux, 3 h; c) N-methyl-4-methoxyaniline, i-PrOH, 2-3 drops HCl; d) anhydrous HCl gas, ether Chemistry Compound AAG 7 was synthesized from the commercial available 3-methyladipic acid 1 (Scheme 2). At reflux in concentrated sulfuric acid in ethanol and cyclization in the presence of sodium in toluene, 1 further reacted with guanidine carbonate to afford 2 (34%). Chlorination of 2 to form 3 (34%) was performed by heating with POCl$_3$ for 3 h. Nucleophilic substitution of 3 with N-methyl-4-methoxyl aniline in iso-propanol gave compound 4 (55%) as a white solid. Compound AAG 7. HCl was precipitated as a white solid when AAG 7 was dissolved in anhydrous ether followed by bubbling with anhydrous hydrochloric acid gas (65%).

Experimental Section for Scheme 2

2-Amino-6-methyl-3,5,6,7-tetrahydro-4H-cyclopenta[d]pyrimidin-4-one (2)

3-Methyladipic acid (1.60 g, 10 mmol) was heated under reflux in ethanol/conc. sulfuric acid solution (35 mL, v/v=2.5/1) for 8 h. The solution was neutralized with ammonium hydroxide to pH=7, then diluted with ethyl acetate (100 mL) and washed with water. The organic phase was dried with anhydrous sodium sulfate and evaporated to afford a light yellow liquid which was used in the next step without further purification. The resulting liquid was diluted in anhydrous toluene (100 mL) and sodium (0.23 g) was added to the solution in part. The mixture was heated under reflux for 3 h and cooled, neutralized with 1N hydrochloric acid solution and washed with water. After drying with anhydrous sodium sulfate, the organic phase was evaporated to afford a light brown liquid. The liquid was used in the next step without further purification. The light brown liquid was diluted with t-BuOH. Guanidine carbonate (2.70 g, 15 mmol) and potassium tert-butoxide (1.68 g, 15 mmol) were added, and the mixture was heated under reflux overnight. The reaction mixture was cooled, and a precipitate was filtered. The residue was washed with warm methanol twice (30 mL×1, 15 mL×1). The filtrate and washings were combined and evaporated under reduced pressure, and the residue was purified by column chromatography using chloroform/methanol (100/1) as eluent to afford 230 mg of 3 (19% yield total for 3 steps) as white solid. TLC $R_f$ 0.36 (CHCl$_3$/CH$_3$OH, 10:1); mp: 319-321° C. $^1$H NMR (DMSO-$d_6$): δ 1.10-1.12 (d, 3H, CH$_3$), δ 1.35-1.46, 1.99-2.20, 2.38-2.72, 2.92-2.98 (m, 5H, CH$_2$CHCH$_2$), δ 6.32 (br, 2H, NH$_2$, exch), δ 10.47 (br, 1H, OH, exch). Anal. (C$_8$H$_{11}$N$_3$O. 0.1 CH$_3$OH)C, H, N: calcd, 57.77, 6.82, 24.95. found, 57.92, 6.78, 24.93.

4-Chloro-6-methyl-6,7-dihydro-5H-cyclopenta[d]pyrimidin-2-amine (3)

Compound 2 (297 mg, 1.8 mmol) and phosphorus oxychloride (15 mL) were heated to reflux for 3 h. The reaction mixture was cooled and evaporated at reduced pressure, and the residue was diluted with chloroform (50 mL) and neutralized with ammonium hydroxide slowly in an ice bath. The organic portion was washed with water (3×30 mL). Solvents were evaporated at reduced pressure, and the residue was purified by column chromatography using chloroform/hexane (4/1) as eluent to afford 112 mg (34%) of 3 as a white-off solid. TLC $R_f$ 0.48 (CHCl$_3$/CH$_3$OH, 10:1); mp: 181.5-182.9° C. $^1$H NMR (DMSO-d$_6$): δ 1.16-1.18 (d, 3H, CH$_3$), δ 1.55-1.65, 2.15-2.38, 2.49-2.62, 2.83-2.92 (m, 5H, CH$_2$CHCH$_2$), δ 6.83 (br, 2H, NH$_2$, exch). Anal. (C$_8$H$_{10}$ClN$_3$) C, H, N, Cl: calcd, 52.32, 5.49, 22.88, 19.31. found, 52.33, 5.62, 22.63, 19.09.

N$^4$-(4-Methoxyphenyl)-N$^4$,6-dimethyl-6,7-dihydro-5H-cyclopenta[d]pyrimidine-2,4-diamine (AAG 7)

Compound 3 (94 mg, 0.51 mmol) and N-methyl-4-methoxylaniline (84 mg, 0.61 mmol) were dissolved in iso-propanol (5 mL). 37% Hydrochloric acid (2 drops) were added to the solution. The mixture was heated to reflux for 3 h. Then the reaction was cooled and evaporated at reduced pressure. The residue was diluted with chloroform, neutralized with ammonium hydroxide in an ice bath, and then washed with water (2×30 mL). Solvents were evaporated and after drying with anhydrous sodium sulfate and evaporation, the residue was purified by column chromatography using chloroform as eluent to afford 80 mg of AAG 7 (55%) as a white solid. TLC $R_f$ 0.26 (CHCl$_3$/CH$_3$OH, 10:1). mp: 146.2-147.5° C. $^1$H NMR (DMSO-d$_6$): δ 0.79-0.81 (d, 3H, CH$_3$), 81.27-1.35, 1.75-1.89, 2.01-2.10, 2.54-2.63 (m, 5H, CH$_2$CHCH$_2$), δ 3.25 (s, 3H, NCH$_3$), δ 3.75 (s, 3H, OCH$_3$), δ 5.90 (br, 2H, NH$_2$, exch), δ 6.90-6.92, 7.09-7.11 (dd, 4H, ph-H). Anal. (C$_{16}$H$_{20}$N$_4$O)C, H, N: calcd, 67.58, 7.09, 19.70. found, 67.45, 7.16, 19.48.

2-Amino-N-(4-methoxyphenyl)-N,6-dimethyl-6,7-dihydro-5H-cyclopenta[d]pyrimidin-4-aminium chloride (AAG 7. HCl)

Compound AAG 7 (150 mg from column) was dissolved in anhydrous ether (25 mL) and anhydrous hydrochloric acid gas was bubbled in till no more solid precipitated out. After filtration, the target compound was obtained as a white solid (110 mg, 65%). mp: 232.8-233.4° C. $^1$H NMR (DMSO-d$_6$): δ 0.82-0.84 (d, 3H, CH$_3$), δ 1.23-1.31, 1.78-1.81, 2.20-2.30, 2.83-2.89 (m, 5H, CH$_2$CHCH$_2$), δ 3.40 (s, 3H, NCH$_3$), δ 3.79 (s, 3H, OCH$_3$), δ 6.99-7.01, 7.29-7.31 (dd, 4H, ph-H), δ 7.70 (br, 2H, NH$_2$, exch), δ 12.93 (br, 1H, HCl, exch). Anal. (C$_{16}$H$_{21}$N$_4$OCl. 0.6CH$_3$OH)C, H, N, Cl: calcd, 58.63, 6.94, 16.48, 10.43. found, 58.58, 6.70, 16.59, 10.41.

Synthesis of AAG11 and AAG12

Scheme 3

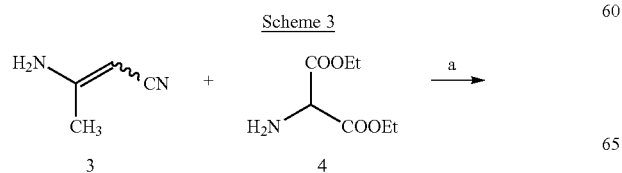

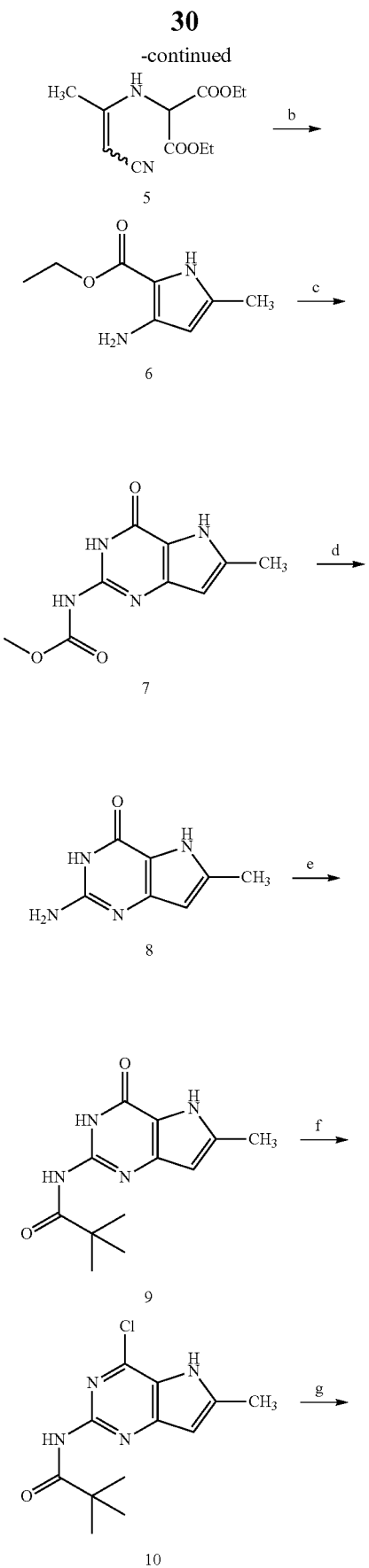

-continued

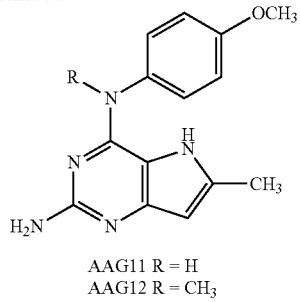

AAG11 R = H
AAG12 R = CH$_3$ $^a$Reagents and conditions: (a) MeOH, rt, 5 h; (b) NaOEt, EtOH, 60° C., 6 h; (c) (1) 1,3-bis(methoxycarbonyl)-2-methyl-thiopseudourea, AcOH, MeOH, rt, 12 h; (2) NaOMe, MeOH, rt, 2 h; (d) 1N NaOH, 55° C, 3 h; (e) PivCl, DMAP, TEA, dichloroethane, 50° C., 12 h; (f) POCl$_3$, reflux, 3 h; (g) (1) Phenylamines, i-PrOH, 2-3 drops of concd HCl, reflux, 30 min, (2) 15% KOH, 1,4-dioxane, reflux, 10 h.

Experimental Section for Scheme 3

Diethyl {[(E/Z)-2-cyano-1-methylvinyl]amino}malonate (5)

To a suspension of E/Z mixture of 3-aminobut-2-enenitrile 3 (3 g, 35.1 mmol) in MeOH (60 mL) was added diethyl aminomalonate hydrochloride 4 (7.9 g, 36.8 mmol). The resulting mixture was stirred at room temperature for 5 h. TLC showed the disappearance of the starting materials and the formation of one major spot at R$_f$ 0.26 (ethyl acetate/n-hexane, 1:2). The reaction solvent was diluted with ethyl acetate (50 mL), washed with brine (30 mL×2), dried over MgSO$_4$. To the organic solvent 15 g silica gel was added and the mixture was evaporated to dryness under reduced pressure. This silica gel plug was loaded on a dry silica gel column (2×15 cm) and flash chromatographed initially with n-hexane (200 mL), then sequentially with 500 mL 5% ethyl acetate in n-hexane, 500 mL 10% ethyl acetate in n-hexane, 500 mL 15% ethyl acetate in n-hexane. Fractions containing the desired product (TLC) were pooled and evaporated to afford 6.74 g (80%) of 5 as an off-white solid: mp 50-52° C.; $^1$H NMR (DMSO-d$_6$) δ 1.18-1.23 (t, 3H, J=6.9 Hz), 2.05 (s, 6H), E isomer 3.94 (s, 1H), 4.18-4.24 (m, 4H), 4.96 (d, 1H, J=7.8 Hz), Z isomer 5.32 (s, 1H), 7.51-7.56 (d, 2H, J=7.8 Hz). Anal. (C$_{11}$H$_{16}$N$_2$O$_4$) C, H, N.

Ethyl 3-amino-5-methyl-1H-pyrrole-2-carboxylate (6)

A solution of NaOEt in EtOH (0.5 M, 120 mL) was added slowly to a stirred solution of 5 (1 g, 4 mmol) in 20 mL EtOH. The reaction mixture was stirred for 6 h at 60° C. and cooled to room temperature; the solvent was evaporated under reduced pressure. The crude product was purified by column chromatography on silica gel with 10% ethyl acetate/n-hexane as the eluent to yield 6 (0.45 g, 65%) as an off-white solid: mp 85-87° C.; R$_f$ 0.36 (ethyl acetate/n-hexane, 1:1); $^1$H NMR (DMSO-d$_6$) δ 1.24 (t, 3H, J=6.4 Hz), 2.03 (s, 3H), 4.12 (q, 2H, J=6.4 Hz), 4.91 (s, 2H), 5.26 (s, 1H), 10.21 (s, 1H). Anal. (C$_8$H$_{12}$N$_2$O$_2$) C, H, N.

Methyl (6-methyl-4-oxo-4,5-dihydro-3H-pyrrolo[3,2-d]pyrimidin-2-yl)carbamate (7)

The pyrrole 6 (2.68 g, 16 mmol) was dissolved in MeOH (40 mL), and 1,3-bis(methoxycarbonyl)-2-methyl-2-thiopseudourea (3.74 g, 18 mmol) was added followed by AcOH (4.6 mL). The mixture was stirred at room temperature overnight and became a thick paste. To the reaction mixture NaOMe in MeOH (25%) 45 mL was added, and stirring was continued at room temperature for 2 h. The mixture was neutralized with AcOH and the solid collected by filtration and washed well with water. After drying, 7 (2.44 g, 69%) was obtained as an off-white powder: mp 234-236° C.; TLC R$_f$ 0.22 (MeOH/CHCl$_3$, 1:5); $^1$H NMR (DMSO-d$_6$) δ 2.28 (s, 3H, CH$_3$), 3.73 (s, 3H, OCH$_3$), 5.95 (s, 1H), 10.90 (s, 1H), 11.10 (s, 1H), 11.76 (s, 1H). Anal. (C$_9$H$_{10}$N$_4$O$_3$·0.79C$_6$H$_6$·0.55C$_7$H$_8$O$_3$S)C, H, N.

2-Amino-6-methyl-3,5-dihydro-4H-pyrrolo[3,2-d]pyrimidin-4-one (8)

To a 200 mL round bottomed flask was added 7 (1 g, 4.5 mmol) suspended in 1N NaOH (35 mL). The reaction mixture was heated at 55° C. for 3 h. The resulting solution was cooled in an ice bath and neutralized with AcOH. The precipitated solid was collected by filtration, washed with brine, and dried in vacuo to afford 0.67 g (92%) of 8 as a white solid: mp 252-254° C.; TLC R$_f$ 0.15 (MeOH/CHCl$_3$, 1:5); $^1$H NMR (DMSO-d$_6$) δ 2.20 (s, 3H), 5.65 (s, 1H), 5.65 (s, 2H), 10.21 (s, 1H), 11.15 (s, 1H). Anal. (C$_7$H$_8$N$_4$O·0.73H$_2$O)C, H, N.

2,2-Dimethyl-N-(6-methyl-4-oxo-4,5-dihydro-3H-pyrrolo[3,2-d]pyrimidin-2-yl)propanamide (9)

To a 250-mL round-bottomed flask was added 8 (1.37 g, 8 mmol) suspended in 40 mL of dichloroethane; then trimethylacetyl chloride (1.99 mL, 16 mmol), DMAP (0.13 g, 1 mmol) and triethylamine (2.68 mL) were added. The mixture was stirred overnight at 50° C. The resulting mixture was cooled, diluted with dichloromethane (50 mL), washed with brine (40 mL×2), dried over Na$_2$SO$_4$ and concentrated in vacuo. To this solution were added methylene chloride (30 mL) and silica gel (5 g) and the solvent evaporated. The silica gel plug obtained was loaded onto a silica gel column and eluted with 9:1 ethyl acetate/n-hexane The fractions containing the product (TLC) were pooled and the solvent was evaporated to afford 1.33 g (67%) of 9 as a white solid: TLC R$_f$ 0.47 (MeOH/CHCl$_3$, 1:10); mp 156-157° C.; $^1$H NMR (DMSO-d$_6$) δ 1.19 (s, 9H), 2.29 (s, 3H), 5.97 (s, 1H), 10.72 (s, 1H), 11.78 (s, 1H), 11.87 (s, 1H). Anal. (C$_{12}$H$_{16}$N$_4$O$_2$"0.15CH$_3$COCH$_3$) C, H, N.

N-(4-chloro-6-methyl-5H-pyrrolo[3,2-d]pyrimidin-2-yl)-2,2-dimethylpropanamide (10)

To a 100-mL round-bottomed flask was added 9 (1.16 g, 4.67 mmol) suspended in 30 mL phosphorus oxychloride. The reaction mixture was heated at reflux with stirring in an anhydrous atmosphere for 3 h. The dark orange solution was allowed to cool to room temperature and concentrated in vacuo. Water (20 mL) was then added to the residue at 0° C. with vigorous stirring to give an exothermic reaction. Concentrated aqueous ammonium hydroxide was added to pH 5 to give a precipitate, which was collected by filtration, washed with water (3×5 mL), and dried in vacuo. The crude product was purified by silica gel column chromatography with 2% MeOH/CHCl$_3$. Recrystallization from MeOH afforded 1.07 g (86%) of 10 as a white solid: TLC R$_f$ 0.35 (MeOH/CHCl$_3$, 1:10); mp 162-163° C.; $^1$H NMR (DMSO-d$_6$) δ 1.19 (s, 9H), 2.47 (s, 3H), 6.33 (s, 1H), 9.85 (s, 1H), 12.07 (s, 1H). Anal. (C$_{12}$H$_{15}$ClN$_4$O)C, H, N, Cl.

N-(4-methoxy-phenyl)-6-methyl-5H-pyrrolo[3,2-d]pyrimidine-2,4-diamine (AAG11)

To a 100-mL round-bottomed flask, flushed with nitrogen, were added 10 (0.2 g, 0.7 mmol), 4-methoxy-phenylamine (0.12 g, 1.05 mmol), i-PrOH (20 mL), and 2-3 drops of concd HCl. The reaction mixture was heated at reflux with stirring for 45 min until the starting material 10 disappeared (TLC). The reaction solution was allowed to cool to room temperature; the solvent was removed under reduced pressure, 1,4-dioxane (10 mL) and 10 mL of 15% KOH aqueous solution were added. The resulting mixture was heated at reflux overnight. After cooling the reaction solution was neutralized with 1 N HCl, and then evaporated in vacuo to dryness and the residue was purified by column chromatography on silica gel with 2% MeOH in CHCl$_3$ as the eluent. Fractions containing the product (TLC) were combined and evaporated to afford 0.1 g (53%) of AAG11 as a brown solid: mp 201-202° C.; R$_f$ 0.42 (MeOH/CHCl$_3$, 1:5); $^1$H NMR (DMSO-d$_6$) δ 2.34 (s, 3H), 3.78 (s, 3H), 5.33 (s, 2H), 5.75 (s, 1H), 6.86 (d, 2H, J=6.3 Hz), 7.72 (d, 2H, J=6.3 Hz), 8.45 (s, 1H), 8.52 (s, 1H). Anal. (C$_{14}$H$_{15}$N$_5$O·0.71CHCl$_3$·0.81HCl) C, H, N.

N-(4-methoxy-phenyl)-6-methyl-5H-pyrrolo[3,2-d]pyrimidine-2,4-diamine (AAG12)

(synthesized as described for AAG11): yield 47%; TLC R$_f$ 0.48 (MeOH/CHCl$_3$, 1:5); mp 161-163° C.; $^1$H NMR (DMSO-d$_6$) δ 2.12 (s, 3H), 3.37 (s, 3H), 3.78 (s, 3H), 5.31 (s, 2H), 5.70 (s, 1H), 6.96 (d, 2H, J=5.4 Hz), 7.15 (d, 2H, J=5.4 Hz), 8.16 (s, 1H). Anal. (C$_{15}$H$_{17}$N$_5$O"0.78H$_2$O)C, H, N.

Synthesis for AAG16

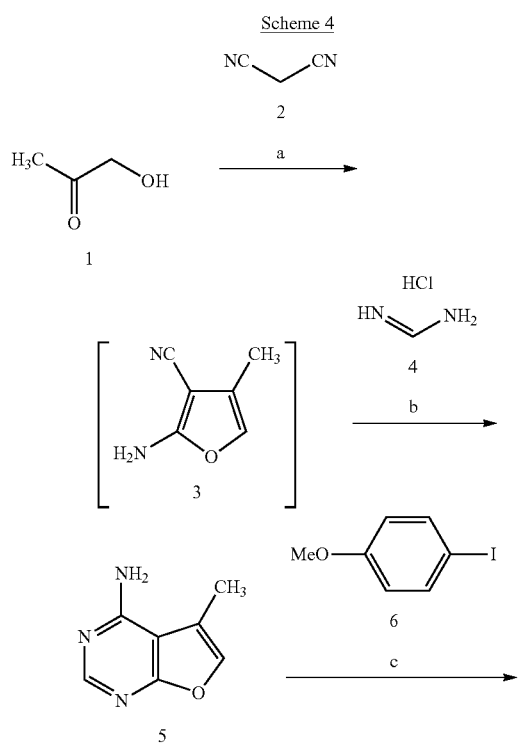

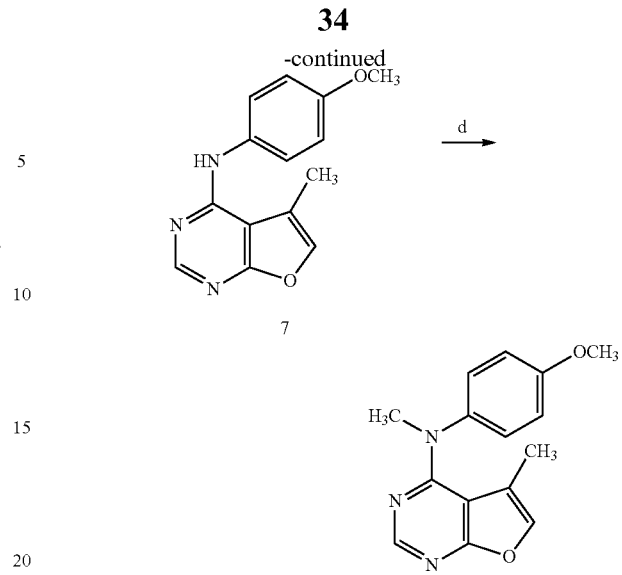

Reagents and conditions: (a) Malononitrile, NEt$_3$, MeOH, RT, 12 h; (b) Formamidine HCl, NaOEt, EtOH, reflux, 8 h; (c) 4-Iodoanisole, CuI, L-Proline, K$_2$CO$_3$, DMF, 110° C., 24 h; (d) NaH, Dimethylsulfide, DMF, 0° C.-RT 8 h Synthesis of AAG16 is shown in Scheme 6 above. Compound 3 was obtained as per reported method by stirring 1 with 2 at room temperature in the presence of triethylamine and was used without purification for further steps. Compound 3 was reacted with free base of formamidine hydrochloride 4 (obtained by stirring at room temperature with sodium ethoxide) in ethanol at reflux to obtain furo[2,3-d]pyrimidine 5. Interestingly no rearrangement to pyrrolo[2,3-d]pyrimidine as before was observed. The product 5 was confirmed using $^1$HMNR and elemental analysis. The amino group of 5 was coupled with 6 using copper (I) iodide and L-proline as a chelating ligand in the presence of potassium carbonate in DMF to afford 7. Compound 7 was N-methylated by treating it with sodium hydride followed by dimethyl sulfate to obtain AAG16.

Experimental Section for Scheme 4

5-methylfuro[2,3-d]pyrimidin-4-amine (5)

Sodium metal (2.3 g; 0.1M) was added cautiously to stirred anhydrous Ethanol (5.8 mL, 0.1M) over 10 min at room temperature. After stirring the resulting slurry for additional 5 min, 4 (8.05 gm, 0.1M) was added. The slurry was stirred at room temperature for 30 min after which solution of 3 (13 g crude; ≈0.1M) in anhydrous ethanol (200 mL) was added. The mixture was heated at reflux for 8 h. After cooling the reaction mixture to room temperature, silica gel (25 g) was added and solvents evaporated under reduced pressure to obtain a plug. Purification was done by flash chromatography using 1% methanol in chloroform. The fractions corresponding to the product spot were pooled and evaporated under reduced pressure to obtain 5 (5.3 g, 35%) as lustrous pink crystals. TLC R$_f$ 0.29 (CHCl$_3$: MeOH, 10:1); mp 240.2-242.5° C.; $^1$H NMR (300 MHz) (DMSO-d$_6$): δ 2.28 (s, 3H, CH$_3$); 7.018 (br, 2H, NH$_2$, exch), 7.528 (s, 1H, C6-CH), 8.12 (s, 1H, C2-CH). Anal. Calcd for C$_7$H$_7$N$_3$O: C, 56.37; H, 4.73; N, 28.17. Found: C, 56.48; H, 4.74; N, 28.17.

N-(4-methoxyphenyl)-5-methylfuro[2,3-d]pyrimidin-4-amine (7)

A 50 mL round bottom flask with a stir bar was charged with copper iodide (66.5 mg, 0.35 mmol), anhydrous potassium carbonate (480 mg, 3.5 mmol), L-proline (80 mg, 0.7 mmol), 5 (150 mg, 1 mmol) and 6 (350 mg, 3.5 mmol). The flask was connected to vacuum for 3 min followed by the addition of anhydrous DMF (15 mL) using syringe. The flask was purged with argon for 5 min and then heated in an oil bath maintained at 110° C. On heating the suspension became bluish grey which lasted for about 2 h. The reaction was stirred for additional 22 h at 110° C. at the end of which the mixture was allowed to cool to room temperature. Ethyl acetate (25 mL) was added and the mixture was poured into water (100 mL). The product was extracted with ethyl acetate (100 mL×2). The combined organic extracts were washed with brine (100 mL) and dried (anhydrous sodium sulfate) and concentrated under reduced pressure. Silica gel (500 mg) was added and solvent evaporated to obtain a plug. Purification by column chromatography using hexanes and ethyl acetate (10:1 to 2:1) afforded 7 (140 mg, 56%) as light brown solid. TLC $R_f$ 0.77 (CHCl$_3$: MeOH, 10:1); mp 99-101.6° C.; $^1$HNMR (400 MHz) (DMSO-d$_6$): δ 2.383-2.386 (d, 3H, CH$_3$, J=1.2 Hz); 3.747 (s, 3H, OCH$_3$), 6.919-6.941 (d, 2H, C$_6$H$_4$, J=8.8 Hz), 7.466-7.488 (d, 2H, C$_6$H$_4$, J=8.8 Hz), 7.65-7.653 (d, 1H, C6-CH, J=1.2 Hz), 8.234 (s, 1H, C2-CH), 8.381 (s, 1H, 4-NH, exch). Anal. Calcd for C$_{14}$H$_{13}$N$_3$O$_2$: C, 65.87; H, 5.13; N, 16.46. Found: C, 65.94; H, 5.13; N, 16.42.

N-(4-methoxyphenyl)-N,5-dimethylfuro[2,3-d]pyrimidin-4-amine (AAG16)

To a 25 mL round bottom flask was weighed 7 (51 mg, 0.2 mmol) and was added DMF (2 mL) to afford a solution. The flask was purged with argon for five min followed by cooling down to 0° C. using ice bath. Sodium hydride (14.4 mg, 0.6 mmol) was added to the solution at 0° C. The solution was stirred for 30 min at 0° C. under argon atmosphere. Dimethyl sulfate (75.7 mg; ≈57 μl, 0.6 mmol) was injected to the reaction mixture and the flask was warmed to room temperature. The mixture was stirred at room temperature for another 3 h at the end of which 1 N Hydrochloric acid (5 mL) was added carefully to quench the reaction followed by water (20 mL) to afford a precipitate. Product was extracted using ethyl acetate (10 mL×2). Combined organic extracts were washed with brine (10 mL) dried (anhydrous sodium sulfate) and concentrated under reduced pressure. Silica gel (200 mg) was added and solvent evaporated to afford a plug. Column chromatography by elution with hexanes:ethyl acetate (5:1) afforded AAG16 (20 mg; 37%) as light brown semisolid; which was triturated with hexanes to afford light brown solid. TLC $R_f$ 0.79 (CHCl$_3$: MeOH, 10:1); mp 84-85.6° C.; $^1$HNMR (400 MHz) (DMSO-d$_6$): δ 1.036-1.039 (d, 3H, CH$_3$, J=1.2 Hz); 3.423 (s, 3H, NCH$_3$), 3.752 (s, 3H, OCH$_3$), 6.944-6.967 (d, 2H, C$_6$H$_4$, J=9.2 Hz), 7.176-7.199 (d, 2H, C$_6$H$_4$, J=9.2 Hz), 7.505-7.508 (d, 1H, C6-CH, J=1.2 Hz), 8.234 (s, 1H, C2-CH). Anal. Calcd for C$_{15}$H$_{15}$N$_3$O$_2$.0.28 C$_6$H$_{14}$.0.05HCl: C, 67.84; H, 6.48; N, 14.22. Found: C, 67.89; H, 6.18; N, 14.06.

Synthesis of AAG20

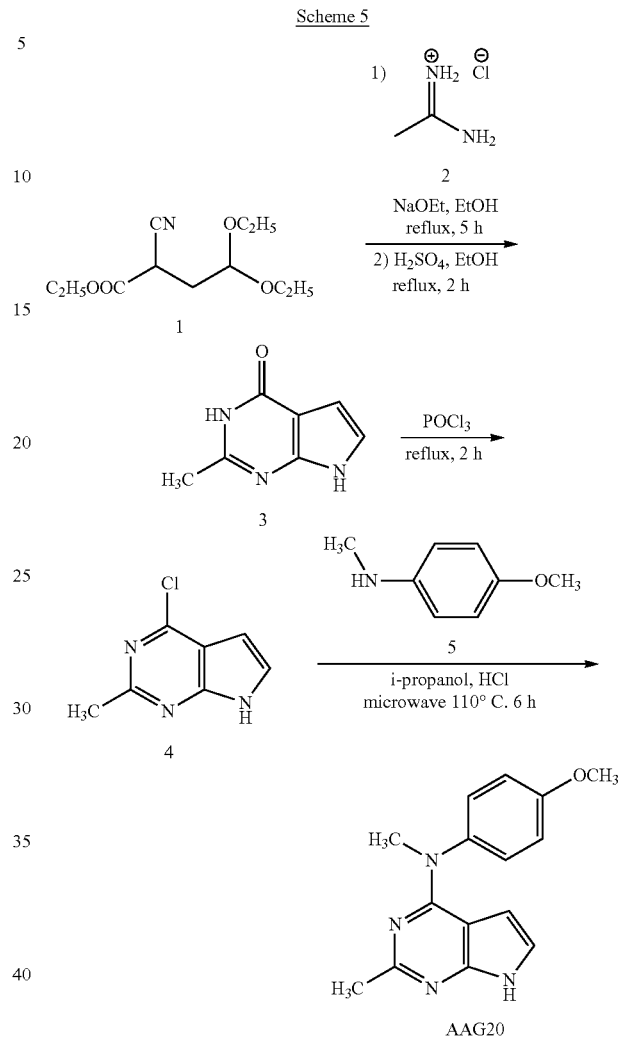

Scheme 5

Experimental Section for Scheme 5

2-Methyl-4-hydroxypyrrolo[2,3-d]pyrimidine (3)

Acetamidine hydrochloride (2, 0.05 mol, 4.7 g) was added to the 0.1M sodium ethoxide solution (75 ml) and kept stirring under room temperature for 0.5 h. After removing the formed sodium chloride by filtration, the filtrate was added the ethyl α-cyano-γ,γ-diethoxybutyrate (1, 0.05 mol, 11.5 g) and the solution was heated under reflux for 5 h. After the removal of most solvent under vacuum, acetic acid was added to adjust the pH to 7.0 and 10.8 g precipitation as white powder. Ethanol (110 ml) with concentrated sulfuric acid (2 ml) was added to the collected powder and was refluxed for 2 h. By the end of the reaction an equal volume of water was added and kept at 4° C. overnight. The pyrrolopyrimidine 3 precipitated as white powder (2.1 g) was used for next step without further purification.

4-chloro-2-methyl-7H-pyrrolo[2,3-d]pyrimidine (4)

The pyrrolopyrimidine 3 (0.01 mol, 1.50 g) was treated with excess POCl$_3$ (20 ml) under reflux for 2 h. Then the remaining POCl$_3$ was removed under vacuum followed by chromatography purification to afford 7 as a white powder (1.42 g) with a yield of 85%. TLC $R_f$=0.62 (CH$_3$OH:CHCl$_3$=1:5). $^1$H NMR (DMSO-d6): δ 2.61 (s, 3H, 2-CH$_3$), 6.52-6.53 (dd, 1H, 5-H), 7.56-7.58 (dd, 1H, 6-H), 12.30 (s, 1H, 7-H).

N-(4-methoxyphenyl)-N,2-dimethyl-7H-pyrrolo[2,3-d]pyrimidin-4-amine (AAG20)

Compound 4 (0.005 mol, 0.835 g) was added to a solution of 4-methoxy-N-methylaniline (5, 0.006 mol, 0.822 g) in i-propanol (10 ml) with drops of conc. HCl. The resulting solution was transferred to a microwave vial (20 ml) and irradiated at 110° C. After 6 h, the reaction was completed and AAG20 was obtained after the chromatographic purification as a white solid (1.01 g) with 80% yield. TLC $R_f$=0.85 (CH$_3$OH:CHCl$_3$=1:5). $^1$H NMR (DMSO-d6): δ 2.65 (s, 3H, 2-CH$_3$), 3.62 (s, 3H, N—CH$_3$), 3.84 (s, 3H, OCH$_3$), 6.99 (bs, 4H, C$_6$H$_4$), 7.11-7.13 (d, 1H, 5-H), 7.39-7.41 (d, 1H, 6-H), 12.44 (s, 1H, 7-H, D$_2$O exchanged). Anal. Calcd. (C$_{15}$H$_{16}$N$_4$O. 0.3688 CHCl$_3$.), C, 59.10; H, 5.28; N, 17.94. Found C, 58.98; H, 5.65; N, 18.16.

Synthesis of AAG 26

Scheme 6

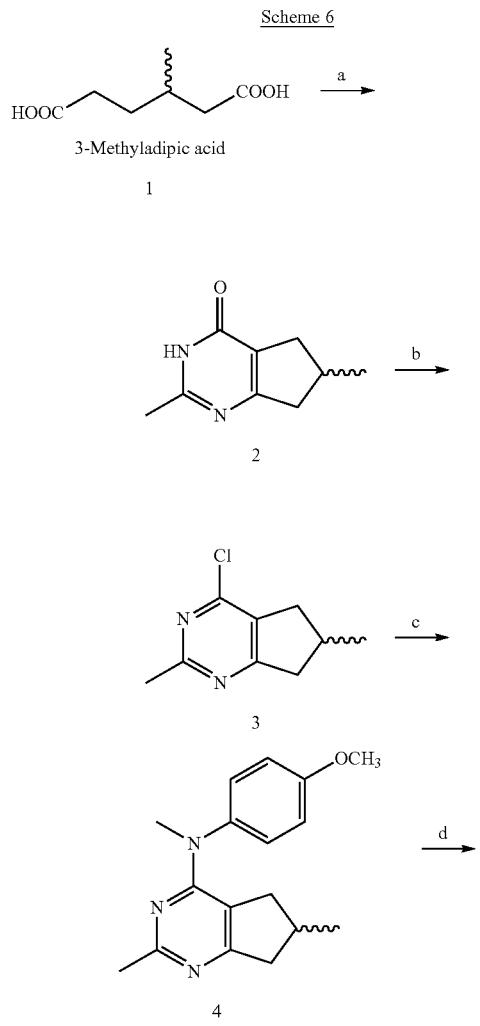

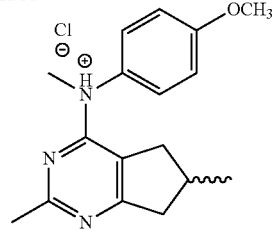

AAG 26

Conditions: (a) 1) Ethanol, conc. Sulfuric acid, reflux, 8 h; 2) Na, toluene, reflux, 3 h; 3) acetamidine hydrochloride, t-BuOH, t-BuOK; (b) POCl$_3$, reflux, 3 h; (c) N-methyl-4-methoxyaniline, i-PrOH, 2-3 drops HCl; d) anhydrous HCl gas, ether Chemistry Compound AAG 26 was synthesized from the commercial available 3-methyladipic acid 1 (Scheme 6). At reflux in concentrated sulfuric acid in ethanol and cyclization in the presence of sodium in toluene, 1 further reacted with acetamidine hydrochloride to afford 2 (30%). Chlorination (69%) of 2 with POCl$_3$ for 3 h afforded 3. Nucleophilic substitution of 3 with N-methyl-4-methoxyl aniline in isopropanol afforded 4, which was further diluted with anhydrous ether and anhydrous hydrochloric acid gas was bubbled in to afford AAG 26 as a white solid (50% for two steps).

Experimental Section for Scheme 6

2,6-Dimethyl-3,5,6,7-tetrahydro-4H-cyclopenta[d]pyrimidin-4-one (2)

3-Methyladipic acid 1 (1.60 g, 10 mmol) was heated under reflux in ethanol/conc. sulfuric acid solution (35 mL, v/v=2.5/1) for 8 h. The solution was neutralized with ammonium hydroxide to pH=7, then diluted with ethyl acetate (100 mL) and washed with water. The organic phase was dried with anhydrous sodium sulfate and evaporated to afford a light yellow liquid which was used in the next step without further purification. The resulting liquid was diluted in anhydrous toluene (100 mL) and sodium (0.23 g) was added to the solution in part. The mixture was heated under reflux for 3 h and cooled, neutralized with 1N hydrochloric acid solution and washed with water. After drying with anhydrous sodium sulfate, the organic phase was evaporated to afford a light brown liquid. The liquid was used in the next step without further purification. The light brown liquid was diluted with t-BuOH. Acetamidine (1.13 g, 12 mmol) and potassium tert-butoxide (1.34 g, 12 mmol) were added, and the mixture was heated under reflux overnight. The reaction mixture was cooled and the precipitate was filtered. The residue was washed with warm methanol twice (30 mL×1, 15 mL×1). The filtrate and washings were combined and evaporated under reduced pressure, and the residue was purified by column chromatography using chloroform/methanol (100/1) as eluent to afford 345 mg (21% yield total for 3 steps) as a white solid. TLC $R_f$ 0.30 (CHCl$_3$/CH$_3$OH, 10:1); mp: 173.9-175.4° C. $^1$H NMR (DMSO-d$_6$): δ 1.05-1.07 (d, 3H, CH$_3$), δ 2.24 (s, 3H, CH$_3$), δ 2.13-2.34, 2.73-2.90 (m, 5H, CH$_2$CHCH$_2$), δ 12.16 (br, 1H, OH, exch). Anal. (C$_9$H$_{12}$N$_2$O)C, H, N: calcd, 65.83, 7.37, 17.06. found, 65.85, 7.36, 17.12.

N-(4-Methoxyphenyl)-N,2,6-trimethyl-6,7-dihydro-5H-cyclopenta[d]pyrimidin-4-aminium chloride (AAG 26)

Compound 2 (0.25 g, 1.5 mmol) and phosphorus oxychloride (10 mL) were heated to reflux for 3 h. The reaction mixture was cooled down and evaporated at reduced pressure, and the residue was diluted with chloroform (50 mL) and neutralized with ammonium hydroxide slowly in an ice bath. The organic portion was washed with water (3×30 mL). Solvents were evaporated at reduced pressure, and the residue was purified by column chromatography using chloroform/hexane (4/1) as eluent to afford 139 mg of 3 as a colorless liquid (69%). Compound 3 (185 mg, 1.01 mmol) and N-methyl-4-methoxylaniline (167 mg, 1.22 mmol) were dissolved in iso-propanol (5 mL). 37% Hydrochloric acid (2 drops) was added in the solution. The mixture was heated to reflux for 3 h. Then the reaction was cooled and evaporated at reduced pressure. The residue was diluted with chloroform, neutralized with ammonium hydroxide, and then washed with water (2×30 mL). Solvents were evaporated and after drying with anhydrous sodium sulfate and evaporation, the residue was purified by column chromatography using chloroform as eluent to afford 4 as a light yellow liquid. TLC $R_f$ 0.24 ($CHCl_3/CH_3OH$, 10:1). The liquid was diluted with anhydrous ether (10 mL) and anhydrous hydrochloric acid gas was bubbled in till no more solid precipitated out. After filtration, the target compound AAG 26 was obtained as a white solid (163 mg, 50% for two steps). mp: 196-198° C. $^1H$ NMR (DMSO-$d_6$): δ 0.85-0.86 (d, 3H, $CH_3$), δ 1.37-1.47, 1.89-1.99, 2.43-2.44, 2.98-3.05 (m, 5H, $CH_2CHCH_2$), δ 2.60 (s, 3H, 2-$CH_3$), δ 3.51 (s, 3H, $NCH_3$), δ 3.80 (s, 3H, $OCH_3$), δ 7.01-7.03, 7.33-7.35 (dd, 4H, ph-H), δ 14.88 (br, 1H, HCl, exch). Anal. ($C_{17}H_{22}N_3OCl$) C, H, N, Cl: calcd, 63.84, 6.93, 13.14, 11.08. found, 63.75, 6.88, 13.05, 10.98.

Preferred Substituted Cyclopenta Pryrimidine Compounds

Introduction

Figure 9:
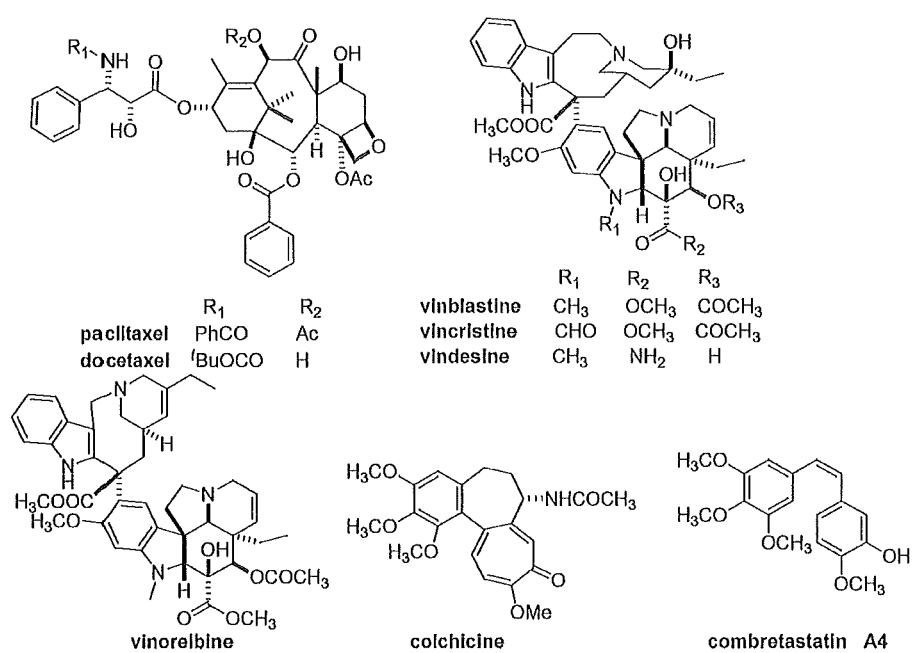
FIG. 9 shows structures of know microtubule targeting agents.

Tubulin binding agents (see FIG. 9 for known microtubule targeting agents) belong to an important class of antitumor agents and are widely used in the clinic for cancer chemotherapy. Most microtubule targeting agents can be divided into three classes based on their interactions within the taxane, vinca, or colchicine site on tubulin. Drugs that bind within the taxoid site include paclitaxel (Taxol), docetaxel (Taxotere), and the epothilones. Paclitaxel and other taxoids (and the epothilones) bind to β-tubulin in the interior of the microtubule. Unlike the other two classes of antimicrotubule agents, the taxoids stimulate tubulin polymerization and are designated as microtubule stabilizers. They are useful in the treatment of breast, lung, ovarian, head and neck and prostate cancers. The second class of microtubule disrupting agents are the vinca alkaloids and these include vincristine, vinblastine, vindesine and vinorelbine. The vinca alkaloids bind between two αβ-tubulin diemers at a site that is distinct from the taxane site. The vinca alkaloids are important in the treatment of leukemias, lymphomas, non-small cell lung cancer and childhood cancers. A diverse collection of small molecules, including colchicine and the combretastatins, bind to the colchicine site on β-tubulin at its interface with α-tubulin, a site distinct from the vinca site. Similar to the vinca alkaloids, colchicine site agents inhibit tubulin polymerization. Colchicine itself is not used as an antitumor agent but is useful in the treatment of gout and familial Mediterranean fever. Although there are no clinically approved anticancer agents that bind within the colchicine site, several agents including 2-methoxyestradiol, combretastatin A-4 (CA-4) phosphorylated prodrug combretastatin A-4 phosphate (CA-4P) (fosbretabulin), the combretastain CA-1P prodrug (OXi4503), BNC105P, ABT-751 and plinabulin (NPT-2358) have been evaluated in clinical trials. While CA-4P, CA-1P and others continue to be evaluated in clinical trials, to date no colchicine site agent has advanced to Phase III studies or FDA approval for anticancer indications, demonstrating the need of developing additional colchicine site agents for potential clinical evaluations.

Preferred Methoxynaphthyl Substituted Cyclopenta Pyrimidine Compounds:

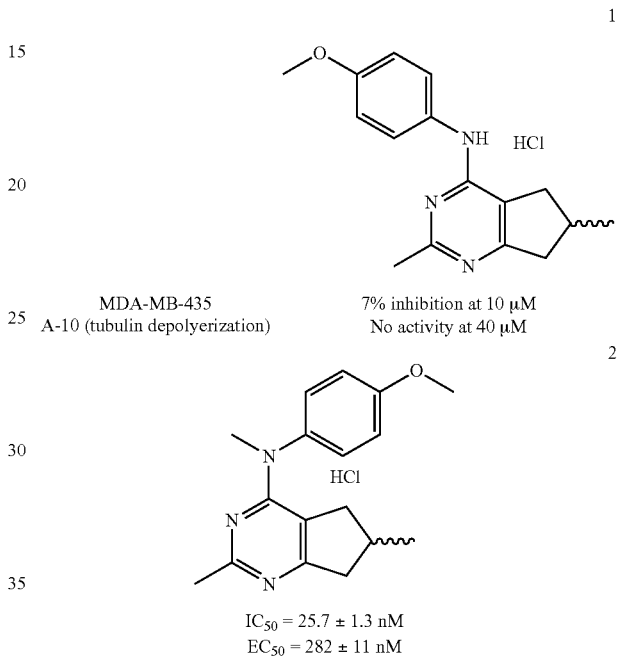

Compounds 1, 2 are cyclopenta pyrimidine compounds. Their antitubulin activities are set forth above. Compound 2 is a high potency antitubulin agent ($IC_{50}$=25.7 nM), while the N-demethyl compound 1 is almost inactive. The structural differences between Compounds 1 and 2 lead to several pharmacological ramifications. Among them, the conformation of aniline rings maybe a pivotal factor that results in the affinity difference. In order to validate this, we set forth a preferred representative series of N-methyl-N-methoxynaphthyl cyclopenta[d]pyrimidin-4-amine (4) based on the high potent antibulin agent 3 ($IC_{50}$=7.0 nM). All these preferred representative methoxynaphthyl substituted bicyclic compounds of this invention have the same function groups and molecular weight, similar Log D.

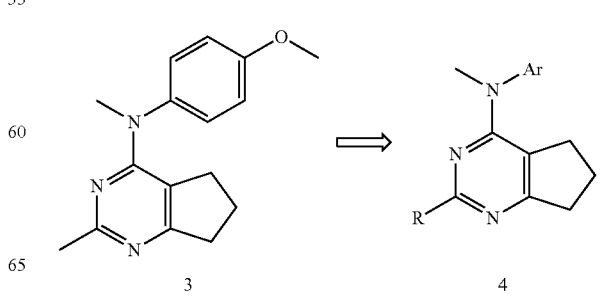

-continued

R = H, CH₃
Ar =

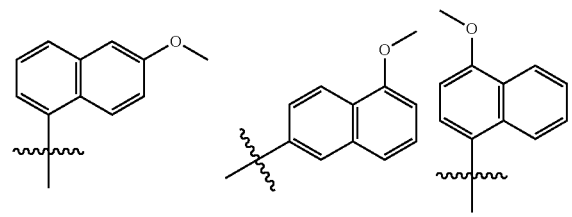

Chemistry:

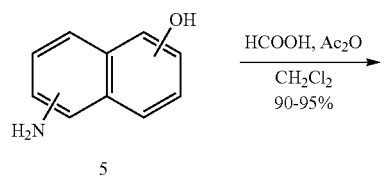
5

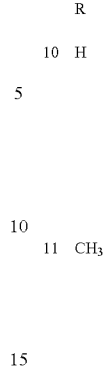 HCOOH, Ac₂O
CH₂Cl₂
90-95%

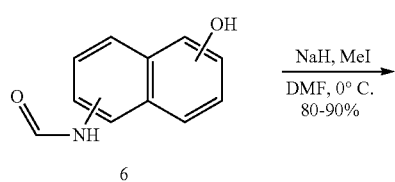
6

NaH, MeI
DMF, 0° C.
80-90%

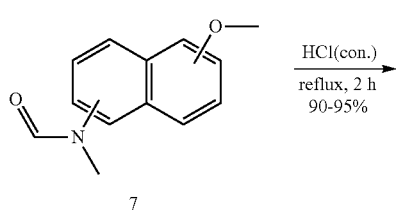
7

HCl(con.)
reflux, 2 h
90-95%

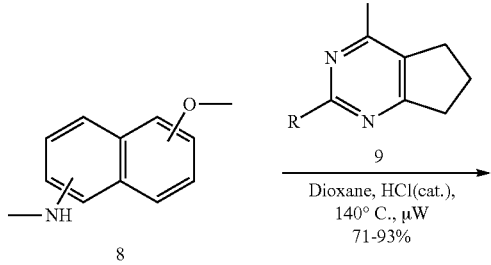
8

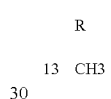
9

Dioxane, HCl(cat.),
140° C., μW
71-93%

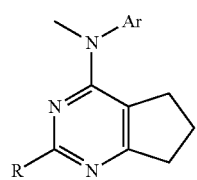

| | R | Ar |
|---|---|---|
| 10 | H | 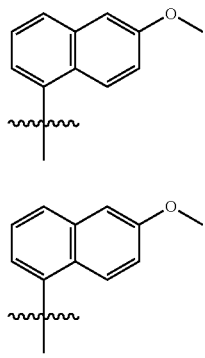 |
| 11 | CH₃ | 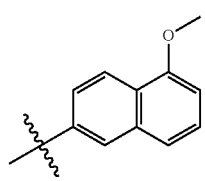 |
| 12 | H | 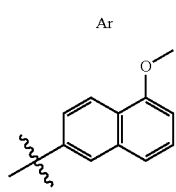 |

| | R | Ar |
|---|---|---|
| 13 | CH₃ | 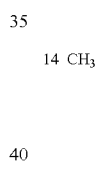 |
| 14 | CH₃ | 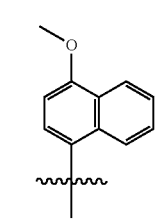 |

Synthesis Scheme of more preferred methoxynaphthyl substituted cyclopenta pyrimidine compounds 10-14 of this invention:

Formyl protection of the amine in hydroxyaminonaphthalenes 5 with formic acid and acetic anhydride afforded N-formyl hydroxynaphthylamine 6 in 90-95% yield. Dimethylation of 6 using NaH and methyl iodide in DMF at 0° C. gave N-methyl-N-formyl methoxynaphthylamine 7 in 80-90% yield. Deformylation of 7 in refluxing concentrated HCl afforded N-methyl methoxylnaphthylamine 8 in 90-95% yield. Nucleophilic displacement of 4-chlorocyclopenta[d]pyrimidine 9 by secondary amine in compounds 8 afforded target more preferred methoxynaphthyl substituted cyclopenta pyrimidine compounds 10-14 of this invention.

Biological Evaluation of Preferred Methoxynaphthyl Substituted Cyclopenta Pyrimidine Compounds 10-14 of this Invention:

TABLE 2

IC$_{50}$ values for inhibition of proliferation of MDA-MB-435
cells and effect on microtubule polymerization.

| Compd. | IC$_{50}$ ± SD (MDA-MB-435) Tumor cells (nM) | EC$_{50}$ in A-10 cells (Tubulin depolymerization inhibitory acitivity) (nM) |
|---|---|---|
| 3 | 7.0 ± 0.7 | 25.9 ± 3.7 |
| 10 | ND | >10000 |
| 11 | ND | >10000 |
| 12 | 33.7 ± 3.4 | 184 ± 4.8 |
| 13 | 10.2 ± 0.46 | |
| 14 | 234 ± 20 | 500 ± 2.1 |
| CA4 | 3.4 ± .6 | 13.0 |

Compounds 3, 10-14 were tested for antiproliferative effects against the drug sensitive MDA-MB-435 tumor cell line in culture using the sulforhodamine B assay reported for the way as standard antitubulin agent CA4. The microtubule disrupting effects of these compounds were observed in a cell-based phenotypic screen. The data (Table 2) indicate that 13 has the comparable antiproliferative effects as CA4 with an IC$_{50}$ of 10 nM. However, the reverse orientation of methoxy and methylamino on the naphthyl, compound 11, has no microtubule depolymerization inhibitory activity up to 10 000 nM. Compound 14 is less potent than 13, but more potent than 11.

TABLE 3

Inhibition of tubulin assembly and colchicine binding by CA-4,
for more preferred substituted cyclopenta pyrimidine
compounds 10-14 of this invention:

| | Inhibition of tubulin assembly IC$_{50}$ (μM) ± SD | Inhibition of colchicine binding % Inhibition ± SD | |
|---|---|---|---|
| Compd. | | 5 μM inhibitor | 1 μM inhibitor |
| 10 | >20 (minimal act) | | |
| 11 | >20 (partial act) | | |
| 12 | 1.2 ± 0.04 | 93 ± 0.6 | 77 ± 1 |
| 13 | 0.98 ± 0.04 | 98 ± 0.3 | 86 ± 0.7 |
| 14 | 1.4 ± 0.007 | 72 ± 0.6 | |
| CA4 | 1.1 ± 0.1 | 99 ± 0.6 | 90 ± 0.2 |

The effects of designed compounds 10-14 on the polymerization of purified tubulin were evaluated. This allows for the study of the direct interaction of the compounds with their intracellular target. The ability of these compounds to bind to the colchicine site on tubulin was evaluated by measuring inhibition of [$^3$H]colchicine binding to tubulin. The data (Table 3) show that compound 13 is an effective and potent inhibitor of tubulin assembly. It is clear that at 1 and 5 μM concentrations, 13 inhibited the binding of [$^3$H] colchicine, somewhat more potently than CA4. It is therefore likely that 13 binds in the colchicine site. Contrary to 13, 11 only shows partial inhibitory activity on tubulin assembly at 20 μM concentration.

TABLE 4

Circumvent clinically relevant models of drug resistance
of more preferred substituted cyclopenta pyrimidine
compounds 10-14 of this invention:

| | IC$_{50}$ ± SD (nM) | | |
|---|---|---|---|
| Compd. | Wild type HeLa | β-III Overexpressing HeLa | Rr |
| 10 | ND | ND | |
| 11 | >10,000 | >10000 | |
| 12 | 15 ± 0 | 14 ± 1 | 1.07 |
| 13 | 4.0 ± 1 | 4.0 ± 1 | 1.0 |
| 14 | 85 ± 5 | 180 ± 40 | 0.47 |
| CA4 | 1.8 ± 0.4 | 2.5 ± 0.7 | 0.72 |
| Paclitaxel | 5.3 ± 2 | 16 ± 1 | 0.33 |
| Docetaxel | 4.0 ± 2 | 13 ± 4 | 0.31 |

One mechanism of drug resistance that can lead to chemotherapy failure with tubulin targeting agents is the expression of the βIII isotype of tubulin. An isogenic HeLa cell line pair was used to evaluate the effects of βIII tubulin expression on the activities of 10-14 in comparison with paclitaxel, Docetaxel and CA4. 13, and CA4 had Rr of 1.0, 0.72, respectively (Table 4), in this cell line pair, suggesting that, like 13, they overcome drug resistance mediated by βIII tubulin compared with Paclitaxel and Docetaxel, which had a Rr of 0.33 and 0.31. These results suggest that 13 would circumvent tumor resistance because of the overexpression of βIII tubulin.

Figure 10:
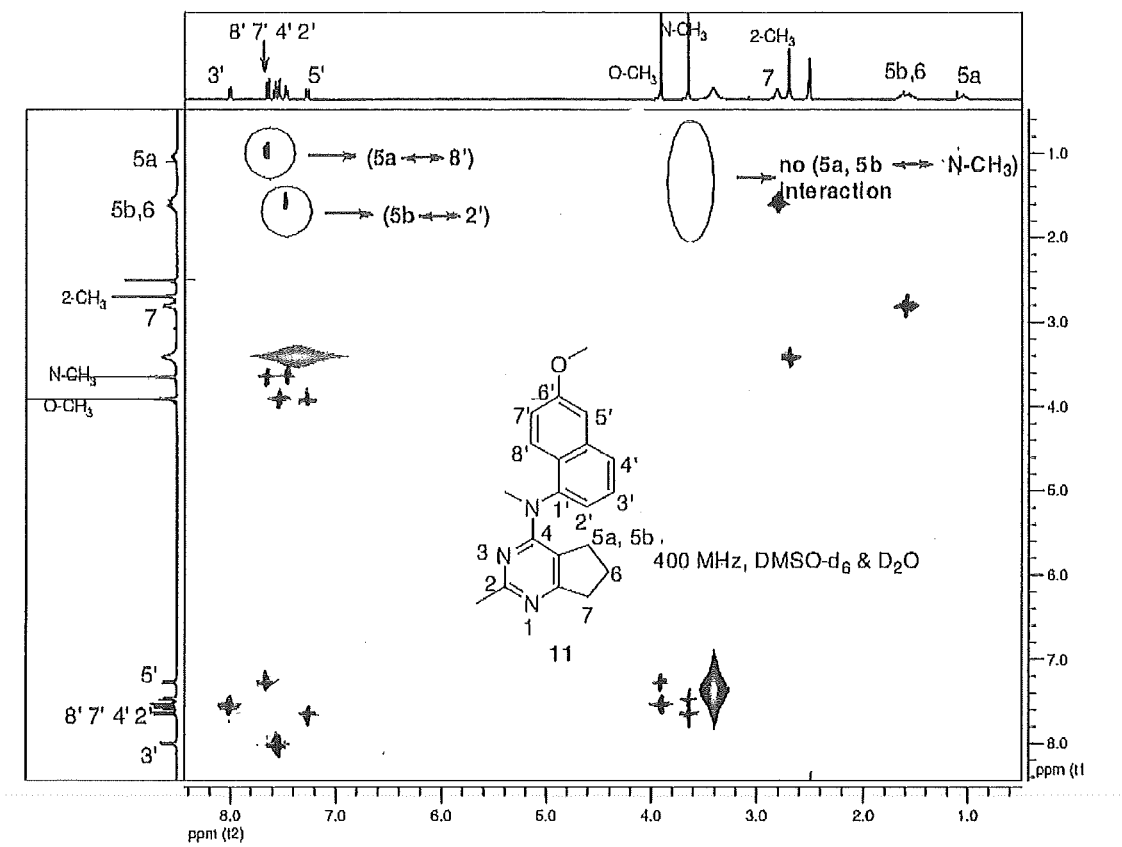
FIG. 10 shows the results and interpretation of a NOESY study of a more preferred methoxynaphthyl substituted cyclopenta pyrimidine compound 11 of the present invention.
Figure 11:
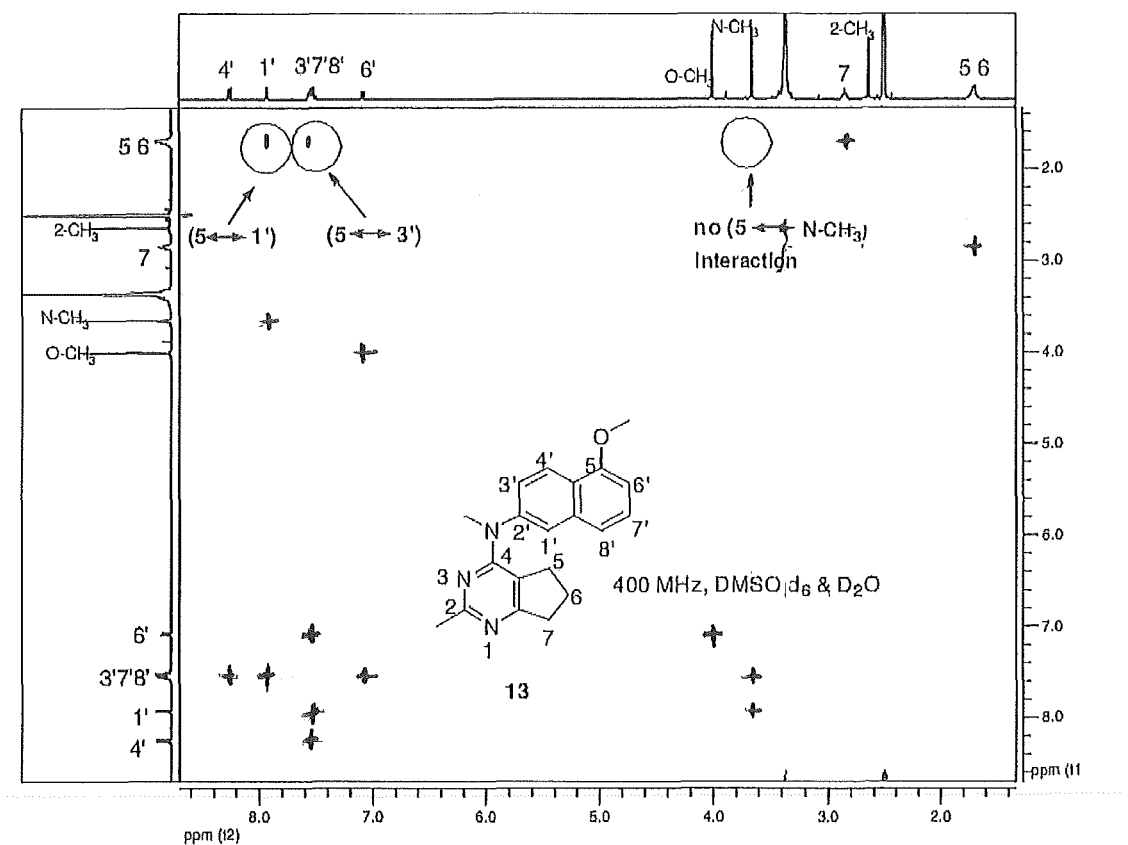
FIG. 11 shows the results and interpretation of a NOESY study of a more preferred methoxynaphthyl substituted cyclopenta pyrimidine compound 13 of the present invention.
Figure 12:
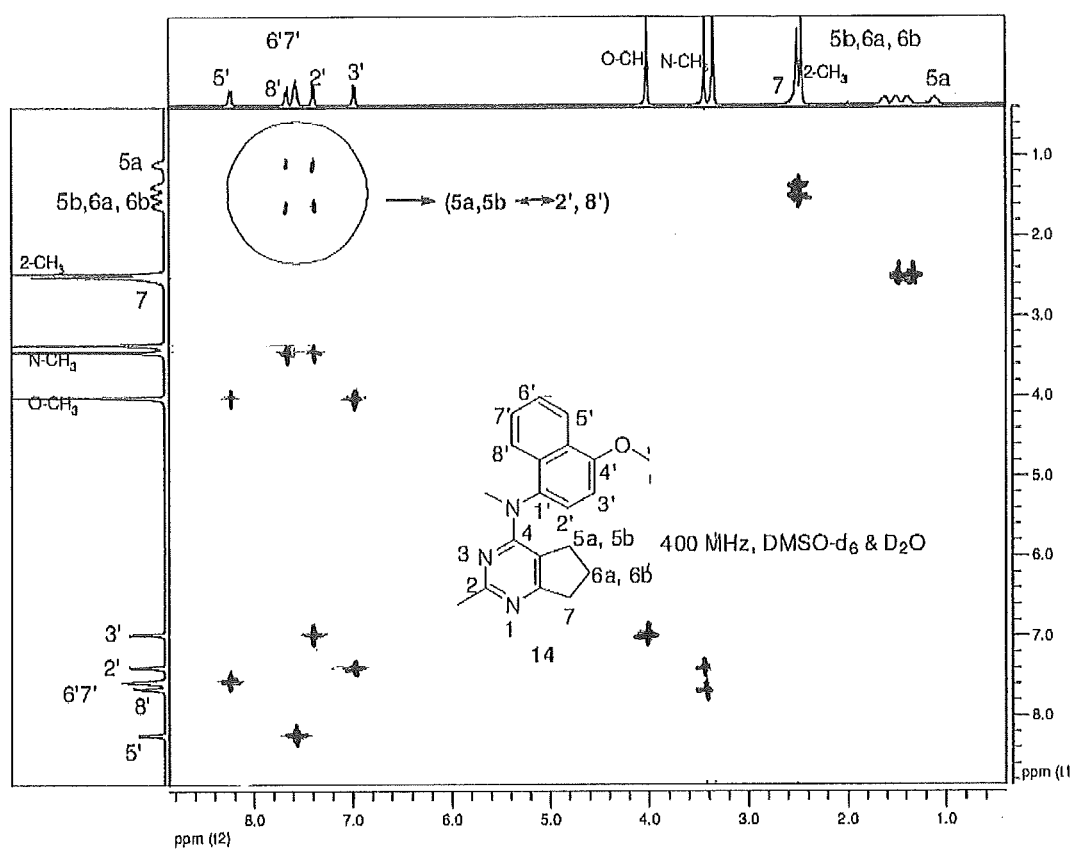
FIG. 12 shows the results and interpretation of a NOESY study of a more preferred methoxynaphthyl substituted cyclopenta pyrimidine compound 14 of the present invention.

Conformation Study:

FIGS. 10, 11, and 12 show the results of the NOESY study of the more preferred substituted cyclopenta pyrimidine compounds 11, 13 and 14 of this invention, respectively, and spectrum interpretation.

The 1-D $^1$HNMR and 2-D $^1$HNMR (NOESY) spectrum study, in DMSO-d$_6$ and D$_2$O, was carried out to explore the stable conformation of the more preferred substituted cyclopenta pyrimidine compounds 11, 13 and 14 of this invention. In 1-D $^1$HNMR, the chemical shift of 5-position protons in all three compounds shifts to upfield (less than 2 ppm), which indicates that the 5-position protons of cyclopenta[d] pyrimidine reside at shielding cone of the naphthyl ring. In 13, the chemical shift of two 5-position protons is identical, which illustrates these two protons reside at the exact same environment. In 11 and 14, the two 5-position protons have different chemical shift, which suggest one atropisomer has higher population than the other atropisomer. Due to 8'-H, the rotation ability of naphthyl ring around cyclopenta[d] pyrimidine ring in compounds 11 and 14 is somewhat restrained.

NOESY is a useful tool to illustrate the space relationship of protons that have distance between 1.8-4.3 angstrum. The 2-D $^1$HNMR (NOESY) spectrum of 13, both of 5-position protons in NOE effect range to both 1' and 3' protons on the naphthyl ring, while the distance of 5-position protons and N-methyl protons is beyond the NOE effect range. This data suggest that napthyl ring is hanging above the cyclopenta ring, and the atropisomers, if exist, are fast interchangeable due to the freely rotatable σ-bonds (C$_1$—N and N—C$_2$'). In compound 11, one of 5-position proton (5a) residues in the NOE effect range of 8' proton, but not 2' proton. The other 5-position proton (5b) residues in the NOE effect range of 2' proton, but not 8' proton. This data suggest that 11 adopts one atropisomer over the other thanks to the absent of free rotation of naphthyl ring toward the cyclopenta[d]pyrimidine ring, in the NMR took place environment (room temperature, DMSO & D$_2$O solution). In compound 14, the two atropisomers is partially convertible. It is clear the naphthyl rings of 11, 13 and 14 place different orientation towards cyclopenta[d]pyrimidine rings, although all the naphthyl rings hang above the cyclopenta side.

Figure 13:
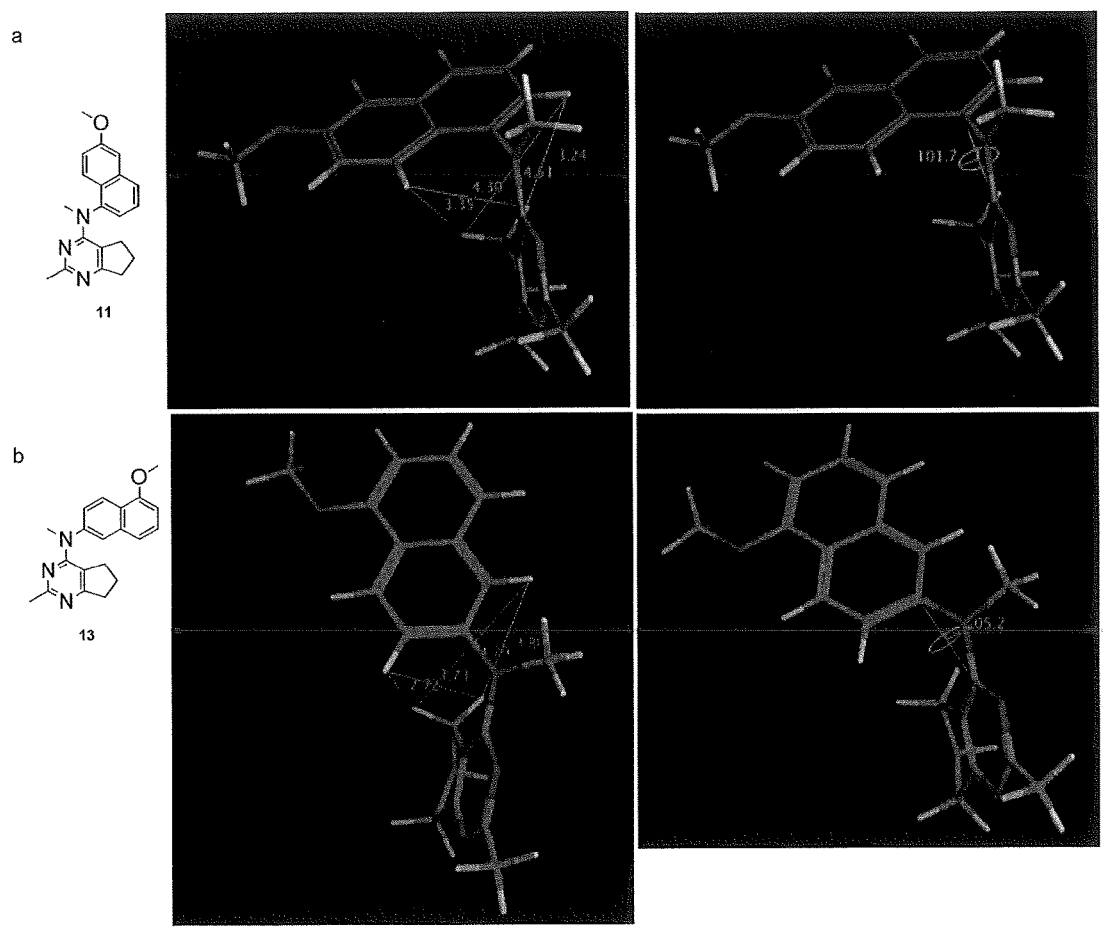
FIGS. 13 a and b show MOE (2012) simulation of the low energy conformer of the more preferred methoxynaphtyl substituted cyclopenta pyrimidine compounds 11 and 13 of the present invention.

FIGS. 13a and b show MOE (2012) simulation of the low energy conformer of the more preferred substituted cyclopenta pyrimidine compounds 11 and 13 of this invention, respectively. Only the atropisomer that methoxynaphthyl group point to the left side were showed and the atropisomer with methoxynapthyl group point to the right side does not present. FIG. 13a: Up-left: the distances of 5-position protons and 2' and 8' protons of 11 in low energy conformer. Distances are: 5a-2' (4.30 Å); 5a-8' (3.35 Å); 5b-2' (3.24 Å); 5b-8' (4.51 Å), which are generally matching with the NOESY results. Up-right: the orthogonal angle of this conformer is 101.7°. FIG. 13b: Low-left: the distances of 5-position protons and 1' and 3' protons of 13 in low energy conformer. Distances are: 5a-1' (3.73 Å); 5a-3' (2.72 Å); 5b-1' (3.80 Å); 5b-8'(4.70 Å), which are matching with the NOESY results. Low-right: the orthogonal angle of this conformer is 105.2°.

In order to establish the orthogonal angle of low energy conformer, the atropisomer (FIG. 13) with methoxynaphthyl point to the left of the more preferred substituted cyclopenta pyrimidine compounds 11 and 13 were chosen to run an energy minimization (MOE, 2012). In 11, distances of 5-position protons and 2' and 8' protons are: 5a-2' (4.30 Å); 5a-8' (3.35 Å); 5b-2' (3.24 Å); 5b-8' (4.51 Å), which are generally matching with the NOESY results. The orthogonal angle of naphthyl ring to cyclopenta[d]pyrimidine ring is 101.7°. In 13, distances of 5-position protons and 1' and 3' protons are: 5a-1' (3.73 Å); 5a-3' (2.72 Å); 5b-1' (3.80 Å); 5b-8'(4.70 Å), which again are matching with the NOESY results. The orthogonal angle of naphthyl ring to cyclopenta[d]pyrimidine ring is 105.2°. Further, we have carried out superimposition of 11 and 13 docked in the colchicine site of tubulin, which indicate that the naphthyl is involved in the π-stack interaction with Tyr224 and that the methoxy is involved in the H-B with ammonium of Lys254.PDB:1SA0. A docking study of compounds 11 and 13 into colchicine site of tubulin has been carried out to elucidate the relationship of the orthogonal angle with binding affinity. The result suggests that the methoxynaphthyl in 13 has stronger π-stack interaction with Tyr224 and stronger H-B with Lys254 than compound 11.

Those persons skilled in the art will appreciate that in order to study the influence of the 3-D conformation of cyclopenta[d]pyrimidine agents on the tubulin antiproliferation activity, we devised three methoxy naphthyl substituted cyclopenta[d]pyrimidine compounds with maximum structural similarity. Among them, the N,2-dimethyl-N-(6'-methoxynaphthyl-1'-amino)-cyclopenta[d]pyrimidin-4-amine (11) shows the rotation hindrance of naphthyl ring with cyclopenta[d]pyrimidine ring, and it adopts orthogonal angle of 101.7°. The N,2-dimethyl-N-(5'-methoxynaphthyl-2'-amino)-cyclopenta[d]pyrimidin-4-amine (13) shows the free rotation capability of naphthyl ring with cyclopenta[d]pyrimidine ring, and it adopts orthogonal angle of 105.2°. The orthogonal and rotational ability difference of 11 and 13 leads to the difference of binding affinity in colchicine binding site on tubulin, and completely difference antitumor activity (11 is inactive while 13 is extremely potent). We have established a method by combining 2-D $^1$HNMR (NOESY) and computer simulation to explore 3-D conformation influence on binding affinity.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:
1. A compound of Formula IV:

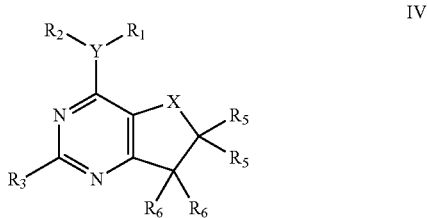

wherein R$_1$ is either a hydrogen or an alkyl having from one to ten carbon atoms and R$_2$ is a substituted naphthyl, or wherein R$_1$ is a substituted naphthyl and R$_2$ is either a hydrogen or an alkyl having from one to ten carbon atoms, and wherein each substituent of any said substituted group is the same or different and is selected from the group consisting of a straight or branched alkyl, alkenyl, or alkynyl, a cyclic or alicyclic group having from one to six carbon atoms, a heterocyclic group having from one to six carbon atoms, an alkoxy group, an aryloxy group, an alkyloxyaryloxy group, an aryl group, an amine, a halogen, a phenol, a naphthalene, a piperidine, a pyrrole, a ketone, a methylalkyl ketone, and a trifluoromethyl ketone, and wherein each of said substituents may itself be substituted, and wherein any of said substituents may be optionally attached by a —CH$_2$—bridge, and wherein the substituent may be optionally partially or completely saturated or unsaturated;

R$_3$ is one of (a) a hydrogen (H), (b) a halogen, and (c) an alkyl having from one to ten carbon atoms and having a straight or a branched configuration, and wherein the alkyl is partially or completely saturated;

R$_5$ is hydrogen;
R$_6$ is hydrogen;
X is CH$_2$; and
Y is a nitrogen (N).

2. A pharmaceutical composition comprising a therapeutically effective amount of a compound of Formula IV and salts thereof:

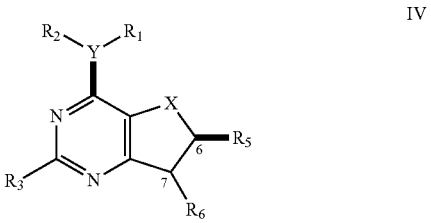

wherein R$_1$ is either a hydrogen or an alkyl having from one to ten carbon atoms and R$_2$ is a substituted naphthyl, or wherein $R_1$ is a substituted naphthyl and $R_2$ is either a hydrogen or an alkyl having from one to ten carbon atoms, and wherein each substituent of any said substituted group is the same or different and is selected from the group consisting of a straight or branched alkyl, alkenyl, or alkynyl, a cyclic or alicyclic group having from one to six carbon atoms, a heterocyclic group having from one to six carbon atoms, an alkoxy group, an aryloxy group, an alkyloxyaryloxy group, an aryl group, an amine, a halogen, a phenol, a naphthalene, a piperidine, a pyrrole, a ketone, a methylalkyl ketone, and a trifluoromethyl ketone, and wherein each of said substituents may itself be substituted, and wherein any of said substituents may be optionally attached by a —$CH_2$— bridge, and wherein the substituent may be optionally partially or completely saturated or unsaturated;

$R_3$ is one of (a) a hydrogen (H), (b) a halogen, and (c) an alkyl having from one to ten carbon atoms and having a straight or a branched configuration, and wherein the alkyl is partially or completely saturated;

$R_5$ is hydrogen;

$R_6$ is hydrogen;

X is $CH_2$; and

Y is a nitrogen (N).

3. The compound of claim 1 wherein $R_1$ is said alkyl having from one to ten carbon atoms and $R_2$ is a substituted naphthyl, or wherein $R_1$ is a substituted naphthyl and $R_2$ is said alkyl having from one to ten carbon atoms.

4. The compound of claim 3 wherein said substituted naphthyl is a methoxynaphthyl.

5. The pharmaceutical composition of claim 2 wherein said substituted naphthyl is a methoxynaphthyl.

* * * * *